(12) United States Patent
Goldberg et al.

(10) Patent No.: US 9,770,710 B2
(45) Date of Patent: Sep. 26, 2017

(54) HYDROGENATION AND DISPROPORTIONATION CATALYSIS

(71) Applicant: University of Washington through its Center for Commercialization, Seattle, WA (US)

(72) Inventors: Karen I. Goldberg, Seattle, WA (US); D. Michael Heinekey, Seattle, WA (US); James M. Mayer, Seattle, WA (US); Alexander J. M. Miller, Seattle, WA (US); Timothy P. Brewster, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/769,314

(22) PCT Filed: Feb. 20, 2014

(86) PCT No.: PCT/US2014/017465
§ 371 (c)(1),
(2) Date: Aug. 20, 2015

(87) PCT Pub. No.: WO2014/130714
PCT Pub. Date: Aug. 28, 2014

(65) Prior Publication Data
US 2016/0121318 A1 May 5, 2016

Related U.S. Application Data

(60) Provisional application No. 61/767,092, filed on Feb. 20, 2013.

(51) Int. Cl.
| | | |
|---|---|---|
| B01J 31/18 | (2006.01) | |
| C07C 29/149 | (2006.01) | |
| C07C 67/08 | (2006.01) | |
| B01J 31/22 | (2006.01) | |

(52) U.S. Cl.
CPC ......... *B01J 31/182* (2013.01); *B01J 31/183* (2013.01); *B01J 31/1815* (2013.01); *B01J 31/2295* (2013.01); *C07C 29/149* (2013.01); *C07C 67/08* (2013.01); *B01J 2231/643* (2013.01); *B01J 2531/822* (2013.01); *B01J 2531/827* (2013.01)

(58) Field of Classification Search
CPC ............... B01J 31/182; B01J 2231/643; B01J 2531/827; C07C 67/08; C07C 29/149
See application file for complete search history.

(56) References Cited

U.S. PATENT DOCUMENTS

| 4,480,115 A | 10/1984 | McGinnis |
|---|---|---|
| 7,459,590 B2 | 12/2008 | Olah et al. |
| 7,605,293 B2 | 10/2009 | Olah et al. |
| 2005/0222188 A1 | 10/2005 | Chapman |
| 2006/0235088 A1 | 10/2006 | Olah |

FOREIGN PATENT DOCUMENTS

| JP | 2004217632 A | * 8/2004 |
|---|---|---|
| WO | 2014/130714 A1 | 8/2014 |

OTHER PUBLICATIONS

Canivet, J., et al., "Water-Soluble Phenanthroline Complexes of Rhodium, Iridium and Ruthenium for the Regeneration of NADH in the Enzymatic Reduction of Ketones," European Journal of Inorganic Chemistry 2007(30):4736-4742, Oct. 2007.
International Search Report and Written Opinion mailed May 23, 2014, issued in corresponding International Application No. PCT/US2014/017465, filed Feb. 20, 2014, 12 pages.
Abura, T., et al., "Isolation and Crystal Structure of a Water-Soluble Iridium Hydride: A Robust and Highly Active Catalyst for Acid-Catalyzed Transfer Hydrogenations of Carbonyl Compounds in Acidic Media," Journal of the American Chemical Society 125(14):4149-4154, Apr. 2003.
Albert, J., et al., "Selective Oxidation of Complex, Water-Insoluble Biomass to Formic Acid Using Additives as Reaction Accelerators," Energy & Environmental Science 5(7):7956-7962, Apr. 2012.
Angamuthu, R., et al., "Electrocatalytic $CO_2$ Conversion to Oxalate by a Copper Complex," Science 327(5963):313-315, Jan. 2010.
Balaraman, E., et al., "Direct Hydrogenation of Amides to Alcohols and Amines Under Mild Conditions," Journal of the American Chemical Society 132(47):16756-16758, Dec. 2010.
Balaraman, E., et al., "Efficient Hydrogenation of Organic Carbonates, Carbamates and Formates Indicates Alternative Routes to Methanol Based on $CO_2$ and CO," Nature Chemistry 3(8):609-614, Jul. 2011.
Benson, E.E., et al., "Electrocatalytic and Homogeneous Approaches to Conversion of $CO_2$ to Liquid Fuels," Chemical Society Reviews 38(1):89-99, Jan. 2009.
Blair, S.L., and W.L. Law, "Electrocatalysis in Other Direct Liquid Fuel Cells," and specifically "Formic Acid, 1930 Wh/L; Methanol, 4820 Wh/L," in H. Liu and J. Zhang (eds.), "Electrocatalysis of Direct Methanol Fuel Cells: From Fundamentals to Applications," Wiley-VCH, Weinheim, Germany, Chap. 14, pp. 527-566, 2009.

(Continued)

*Primary Examiner* — Paul A Zucker
(74) *Attorney, Agent, or Firm* — Christensen O'Connor Johnson Kindness PLLC

(57) ABSTRACT

Improved catalytic methods are disclosed. The methods include both hydrogenation and disproportionation catalysis. While the reaction conditions for hydrogenation and disproportionation differ, the catalysts disclosed herein can be used for either process. In certain aspects, the methods utilize a catalyst: $CpM(N-N)L_n$; wherein Cp is a substituted or unsubstituted cyclopentadienyl ligand; wherein M is selected from the group consisting of Ir and Rh; wherein N—N is a substituted or unsubstituted bidentate ligand selected from the group consisting of a bipyridine ligand and a phenanthroline ligand; wherein n is 0 or 1; and wherein when n is 1 L is selected from the group consisting of an anion and a molecule of a solvent.

20 Claims, 40 Drawing Sheets

(56) References Cited

OTHER PUBLICATIONS

Boddien, A., et al., "Efficient Dehydrogenation of Formic Acid Using an Iron Catalyst," Science 333(6050):1733-1736, Sep. 2011.
Chardon-Noblat, S., et al., "Electrochemical Properties of [(C$_5$Me$_5$)Rh$^{'''(L)Cl}$]$^+$ Complexes (L=2,2'-Bipyridine or 1,10-Phenanthroline Derivatives) in Solution in Related Polypyrrolic Films. Application to Electrocatalytic Hydrogen Generation," Journal of Electroanalytical Chemistry 352(1-2):213-228, Jun. 1993.
Crabtree, R.H., "Resolving Heterogeneity Problems and Impurity Artifacts in Operationally Homogeneous Transition Metal Catalysts," Chemical Reviews 112(3):1536-1554, Mar. 2012.
Criado, J.M., et al., "Mechanism of Formic Acid Decomposition on 3d Metal Oxides," Journal of Catalysis 23(1):11-18, Oct. 1971.
Dadci, L., et al., "Tr-Arene Aqua Complexes of Cobalt, Rhodium, Iridium, and Ruthenium: Preparation, Structure, and Kinetics of Water Exchange and Water Substitution," Inorganic Chemistry 34(1):306-315, Jan. 1995.
Fierro, J.L.G., "Catalysis in C$_1$ Chemistry: Future and Prospect" Catalysis Letters 22(1):67-91, Mar. 1993.
Fukuzumi, S., et al., "Unusually Large Tunneling Effect on Highly Efficient Generation of Hydrogen and Hydrogen Isotopes in pH-Selective Decomposition of Formic Acid Catalyzed by a Heterodinuclear Iridium-Ruthenium Complex in Water," Journal of the American Chemical Society 132(5):1496-1497, Feb. 2010.
Gao, Y., et al., "The Interconversion of Formic Acid and Hydrogen/Carbon Dioxide Using a Binuclear Ruthenium Complex Catalyst," Journal of the Chemical Society, Dalton Transactions 2000(18):3212-3217, Aug. 2000.
Geilen, F.M.A., et al., "Selective Homogeneous Hydrogenation of Biogenic Carboxylic Acids With [Ru(TriPhos)H]$^+$: A Mechanistic Study," Journal of the American Chemical Society 133(36):14349-14358, Sep. 2011.
Haynes, A., et al., "Promotion of Iridium-Catalyzed Methanol Carbonylation: Mechanistic Studies of the Cativa Process," Journal of the American Chemical Society 126(9):2847-2861, Mar. 2004.
Hazari, N., et al., "Selective Homogeneous and Heterogeneous Catalytic Conversion of Methanol/Dimethyl Ether to Triptane," Accounts of Chemical Research 45(4):653-662, Apr. 2012.
Himeda, Y., "Highly Efficient Hydrogen Evolution by Decomposition of Formic Acid Using an Iridium Catalyst With 4,4'-Dihydroxy-2,2'-bipyridine," Green Chemistry 11(12):2018-2022, Oct. 2009.
Hoertz, P.G., et al., "Bidentate Dicarboxylate Capping Groups and Photosensitizers Control the Size of IrO$_2$ Nanoparticle Catalysts for Water Oxidation," Journal of Physical Chemistry B 111(24):6845-6856, Jun. 2007.
Huff, C.A., and M.S. Sanford, "Cascade Catalysis for the Homogeneous Hydrogenation of CO$_2$ to Methanol," Journal of the American Chemical Society 133(45):18122-18125, Nov. 2011.
Hull, J.F., et al., "Reversible Hydrogen Storage Using CO$_2$ and a Proton-Switchable Iridium Catalyst in Aqueous Media Under Mild Temperatures and Pressures," Nature Chemistry 4(5):383-388, Mar. 2012.
Jessop, P.G., et al., "Recent Advances in the Homogeneous Hydrogenation of Carbon Dioxide," Coordination Chemistry Reviews 248(21-24):2425-2442, Dec. 2004.
Jin, F., et al., "Hydrothermal Conversion of Carbohydrate Biomass Into Formic Acid at Mild Temperatures," Green Chemistry 10(6):612-615, Apr. 2008.
Keim, W., "C$_1$ Chemistry: Potential and Developments," Pure and Applied Chemistry 58(6):825-832, Jan. 1986.
Leitner, W., "Carbon Dioxide as a Raw Material: The Synthesis of Formic Acid and Its Derivatives From CO$_2$," Angewandte Chemie International Edition 34(20):2207-2221, Nov. 1995.
Lewis, N. S., and D.G. Nocera, "Powering the Planet: Chemical Challenges in Solar Energy Utilization," Proceedings of the National Academy of Sciences USA (PNAS) 103(43):15729-15735, Oct. 2006.
Liu, C., et al., "Photocatalytic CO$_2$ Reduction and Surface Immobilization of a Tricarbonyl Re(I) Compound Modified With Amide Groups," ACS Catalysis 3(4):655-662, Feb. 2013.
Loges, B., et al., "Catalytic Generation of Hydrogen From Formic Acid and Its Derivatives: Useful Hydrogen Storage Materials," Topics in Catalysis 53(13):902-914, Aug. 2010.
Maitlis, P.M., and V. Zanotti, "The Role of Electrophilic Species in the Fischer-Tropsch Reaction," Chemical Communications 2009(13):1619-1634, Apr. 2009.
Mars, P., et al., "The Catalytic Decomposition of Formic Acid," in D.D. Eley et al. (eds.), "Advances in Catalysis," Academic Press, 1963, vol. 14, pp. 35-113, Jan. 1963.
Marshall, A.-L., and P.J. Alaimo, "Useful Products From Complex Starting Materials: Common Chemicals From Biomass Feedstocks," Chemistry—A European Journal 16(17):4970-4980, May 2010.
Miller, A.J.M., et al., "Catalytic Disproportionation of Formic Acid to Generate Methanol," Angewandte Chemie International Edition 52(14):3981-3984, Apr. 2013.
Ogo, S., et al., "pH-Dependent Transfer Hydrogenation, Reductive Amination, and Dehalogenation of Water-Soluble Carbonyl Compounds and Alkyl Halides Promoted by Cp*Ir Complexes," Organometallics 20(23):4903-4910, Nov. 2001.
Olah, G.A., "Beyond Oil and Gas: The Methanol Economy," Angewandte Chemie International Edition 44(18):2636-2639, Apr. 2005.
Olah, G.A., et al., "Anthropogenic Chemical Carbon Cycle for a Sustainable Future," Journal of the American Chemical Society 133(33):12881-12898, Aug. 2011.
Robertson, A., et al., "The Development of Aqueous Transfer Hydrogenation Catalysts," Dalton Transactions 40(40)10304-10310, Oct. 2011.
Rozovskii, A.Y., and G.I. Lin, "Fundamentals of Methanol Synthesis and Decomposition," Topics in Catalysis 22(3)137-150, Apr. 2003.
Russell, P.G., et al., "The Electrochemical Reduction of Carbon Dioxide, Formic Acid, and Formaldehyde," Journal of the Electrochemical Society 124(9):1329-1338, Sep. 1977.
Sabatier, P., and A. Mailhe, "Chimie Organique—Sur la Décomposition Catalytique de l'Acide Formique," Comptes Rendus de Hebdomadaires des Séances de l'Académie des Sciences 152:1212-1215, May 1911.
Savéant, J.-M., "Molecular Catalysis of Electrochemical Reactions. Mechanistic Aspects," Chemical Reviews 108(7):2348-2378, Jul. 2008.
Wang, W., et al., "Recent Advances in Catalytic Hydrogenation of Carbon Dioxide," Chemical Society Reviews 40(7):3703-3727, Jul. 2011.
Wang, W.-H., et al., "Highly Efficient D$_2$ Generation by Dehydrogenation of Formic Acid in D$_2$O Through H$^+$/D$^+$ Exchange on an Iridium Catalyst: Application to the Synthesis of Deuterated Compounds by Transfer Deuterogenation," Chemistry: A European Journal 18(30):9397-9404, Jul. 2012.
Wesselbaum, S., et al., "Hydrogenation of Carbon Dioxide to Methanol by Using a Homogeneous Ruthenium-Phosphine Catalyst," Angewandte Chemie International Edition 51(30):7499-7502, Jul. 2012.
White, C., et al., "53. ($\eta^5$-Pentamethylcyclopentadienyl)rhodium and -Iridium Compounds," in R.M. Grimes (ed.), "Inorganic Syntheses," Wiley, Hoboken, NJ, Sep. 1992, vol. 29, "Transition Metal Organometallics and Ligands," pp. 228-234.
Wolpher, H., et al., "Synthesis and Electron Transfer Studies of Ruthenium-Terpyridine-Based Dyads Attached to Nanostructured TiO$_2$," Inorganic Chemistry 46(3):638-651, Feb. 2007.

\* cited by examiner

HYDROGENATION AND DISPROPORTIONATION CATALYSIS

CROSS-REFERENCE TO RELATED APPLICATION

This application claims the benefit of U.S. Patent Application No. 61/767,092, filed Feb. 20, 2013, the disclosure of which is hereby incorporated by reference in its entirety.

STATEMENT OF GOVERNMENT LICENSE RIGHTS

This invention was made with government support under Grant Nos. CHE-0650456 and CHE-1205189, both awarded by National Science Foundation (NSF). The government has certain rights in the invention.

BACKGROUND

Reduction of carboxylic acids to alcohols is a fundamental transformation in organic chemistry. Traditionally, this reaction has been carried out using stoichiometric quantities of strong reducing agents such as lithium aluminum hydride or lithium triethylborohydride. The use of stoichiometric amounts of strong reductants is undesirable due to issues of reagent compatibility and the poor atom economy of the overall transformation.

An attractive alternative would be the direct hydrogenation of the carboxylic acid by dihydrogen. Unfortunately, carboxylic acids are among the most difficult carbonyl substrates to hydrogenate due to the low electrophilicity of the carbonyl carbon. It is unsurprising, therefore, that to date only two homogeneous systems for acid hydrogenation have been reported, both of which operate under relatively forcing conditions. Frediani and coworkers reported a series of ruthenium carbonyl-hydride clusters capable of hydrogenative coupling of various carboxylic acids to produce alkyl esters at 180° C. under 130 atm of $H_2$. More recently, Leitner and coworkers reported a ruthenium tris-phosphine catalyst capable of hydrogenating bio-derived acids such as levulinic acid and itaconic acid. Depending on the reaction conditions (typically 100 atm $H_2$, 160° C., Brønsted acid promoter) a variety of reduced products were formed, including lactones, alcohols, diols, and substituted tetrahydrofurans.

In view of the present state of the art, improved catalytic methods for direct hydrogenation by dihydrogen are desired.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a method of hydrogenating a substrate is provided. In one embodiment, the method comprising exposing the substrate and a catalyst to hydrogen gas; wherein the catalyst is selected from the group consisting of:

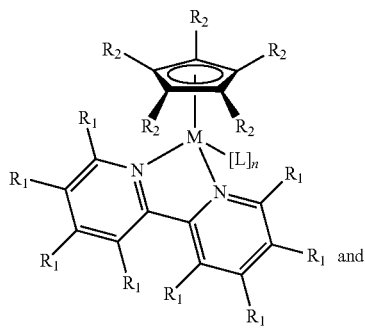

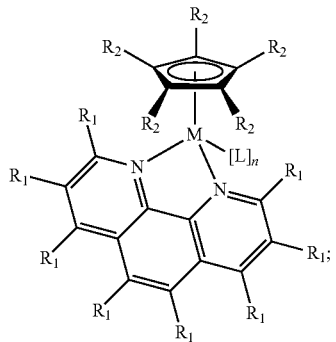

wherein M is selected from the group consisting of Ir and Rh;

wherein n is 0 or 1;

wherein when n is 1 L is selected from the group consisting of an anion and a molecule of a solvent;

wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

In another aspect, a method of hydrogenating a substrate, comprising exposing the substrate and a catalyst to hydrogen gas, wherein the catalyst comprises:

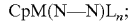

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

In another aspect, a method of forming methanol and methyl formate is provided. In one embodiment, the method comprises contacting formic acid with a catalyst selected from the group consisting of:

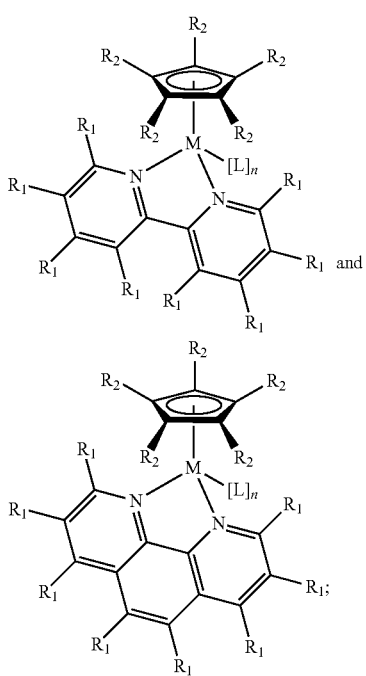

wherein M is selected from the group consisting of Ir and Rh;

wherein n is 0 or 1;

wherein when n is 1 L is selected from the group consisting of an anion and a molecule of a solvent;

wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

In another aspect, a method of forming methanol and methyl formate is provided. In one embodiment the method comprises contacting formic acid with a catalyst comprising:

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A: 27 atm $H_2$, 2 mL glacial AcOH, 120° C., 65 h. FIG. 2B: 2 mM [Cp*Ir(bpy)(OH$_2$)][OTf]$_2$ (bpy=2,2'-bipyridine, OTf=trifluoromethanesulfonate) (catalyst 1), 2 mL 3:1 $H_2O$:HBF$_4$, 27 atm $H_2$, 120° C., 18 h. FIG. 2C: 2 mM 1, 2 mL glacial AcOH, 120° C., 65 h. FIG. 2D: 2 mM 1, 2 mL 8.7 M AcOH (aq.) at given pH (adjusted with HBF$_4$), 120° C., 65 h.

(FIG. 15A) TON for methanol production as a function of pH (3 M HCO$_2$H, filled circles) and [HCO$_2$H] (empty circles). (FIG. 15B) Methanol selectivity as a function of pH (3 M HCO$_2$H, filled circles) and [HCO$_2$H] (empty circles). Conditions: 0.25 mM 1, 80° C., 24 h; solutions were adjusted to the appropriate pH using HBF$_4$ or NaOH.

DETAILED DESCRIPTION

Figure 1:
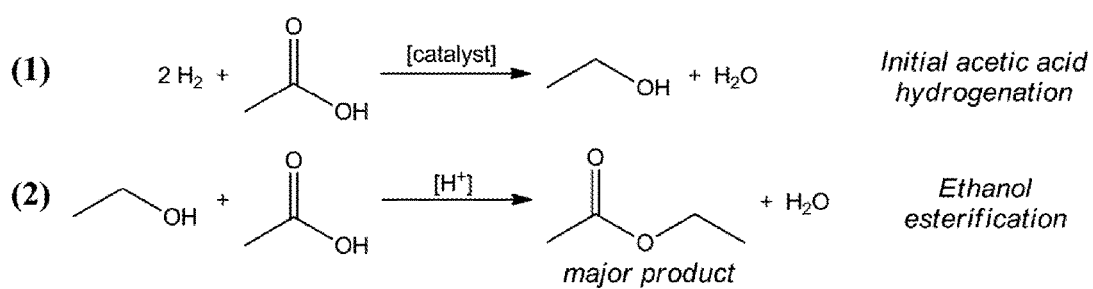
FIG. 1. Reductive coupling reaction sequence in accordance with the hydrogenation method disclosed herein.
Figure 2A:
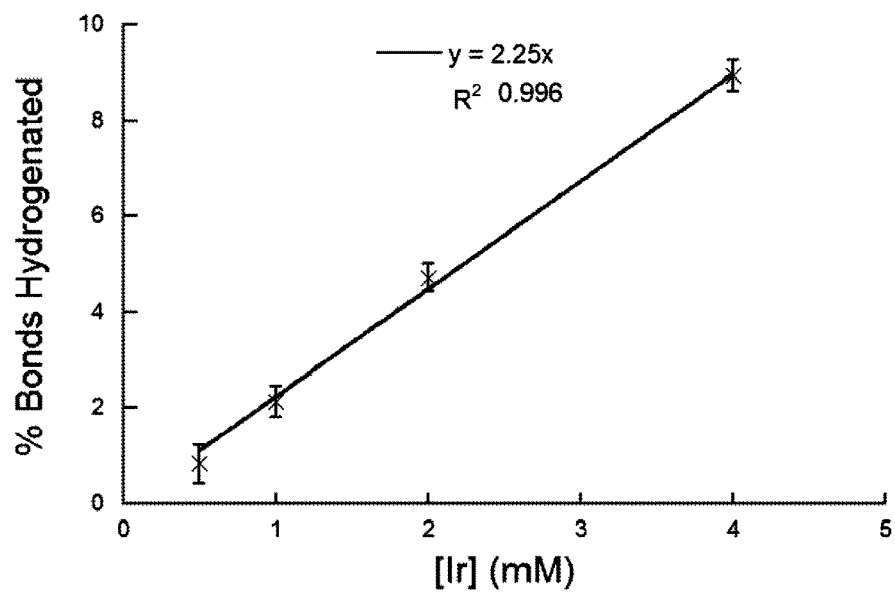
FIGS. 2A-2D. Mechanistic analysis of the hydrogenation of acetic acid catalyzed by a representative catalyst disclosed herein under various conditions.
Figure 2B:
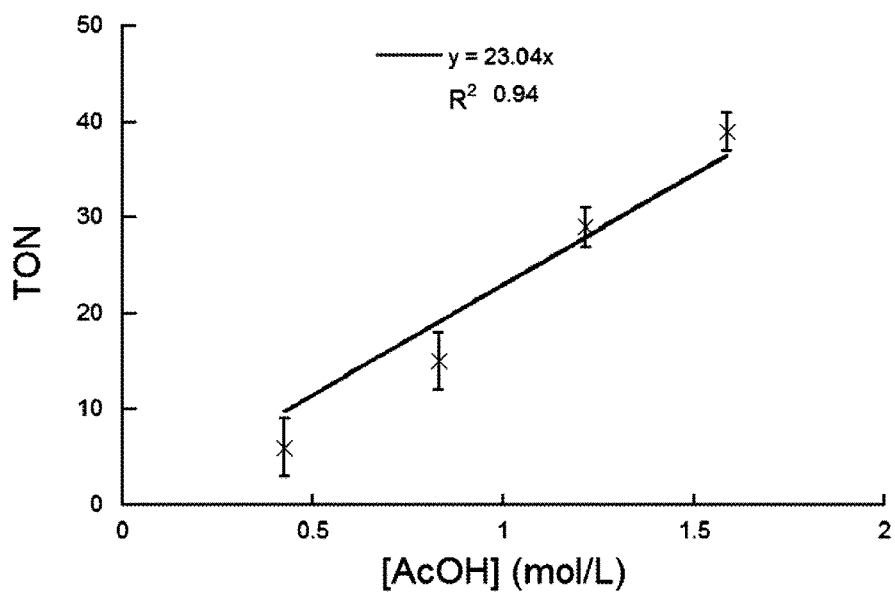
Figure 2C:
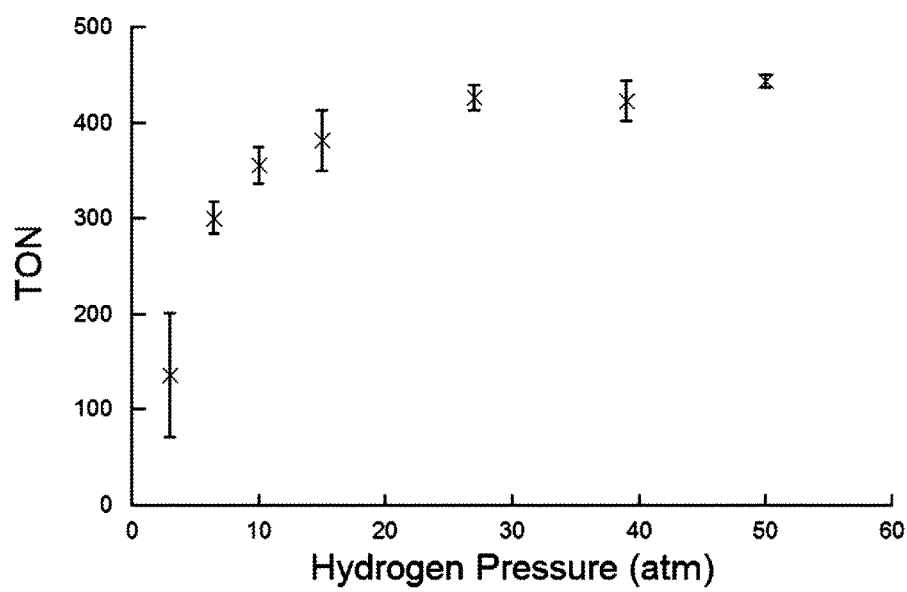
Figure 2D:
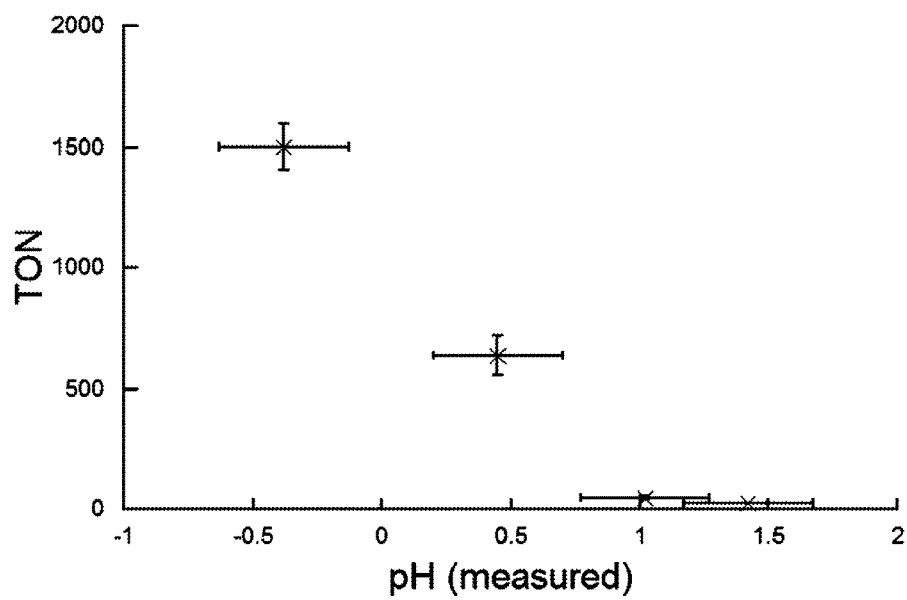

Improved catalytic methods are disclosed. The methods include both hydrogenation and disproportionation catalysis. While the reaction conditions for hydrogenation and disproportionation differ, the catalysts disclosed herein can be used for either process. The disclosed hydrogenation and disproportionation methods are improvements over the present state of the art.

Catalysts

In certain aspects, the methods rely on a catalyst:

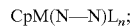

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

In other aspects, the catalyst is selected from the group consisting of:

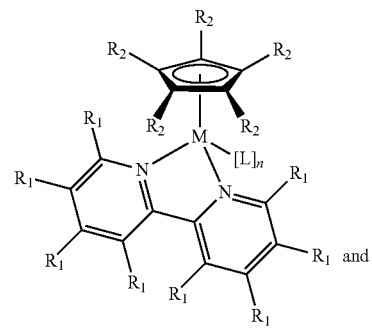

and

-continued

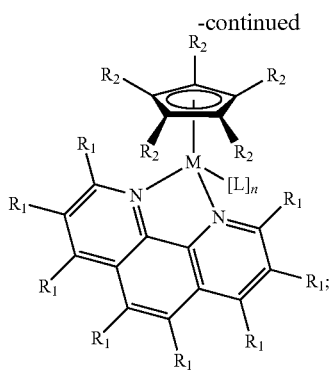

wherein M is selected from the group consisting of Ir and Rh;

wherein n is 0 or 1;

wherein when n is 1 L is selected from the group consisting of an anion and a molecule of a solvent;

wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

The catalysts of the above aspects will now be discussed to the extent generally applicable to both the hydrogenation and the disproportionation methods disclosed. Specific details of the catalysts related to each type of catalytic method will be discussed in detail when describing the individual method types.

The catalyst include a metal center, M, which is either iridium (Ir) or rhodium (Rh), both of which are Group 9 elements. In the disclosed catalysts, M typically has an oxidation state of III (3+) or I (1+). M typically has an oxidation state of III when L is present (i.e., n=1). Conversely, M has an oxidation state of I when L is absent (i.e., n=0). Exemplary catalysts in the M(I) state include Cp*Ir(bpy) and Cp*Rh(bpy).

In embodiments where the catalyst is a cation, the catalyst has a charge of +1 or +2. When the catalyst is a cation, an anion is associated with the cation. If the catalyst is in solid form (e.g., prior to introduction into a reaction solution), a certain anion may be associated with the catalyst. After introduction into a reaction solution, the same or a different anion may be associated with the catalyst. The anion can be a single species or multiple species. For example, if the catalyst has a charge of +2, there can be one or more counter ions. In one embodiment, the anions are two singly negatively charged counter ions (2A$^-$). In another embodiment, anion is one doubly negatively charged counter ion (A$^{2-}$). Representative counter ions include triflate, $PF_6$, chloride, fluoride, BF4, triflamide, tetraphenylborate, iodide, bromide, tetrafluorophenylborate, tetrakis[3,5-bis(trifluoromethyl)phenyl]borate, $SbF_6$, $NO_3$, $ClO_4$, tetrakis(pentafluorophenyl)borate, tosylate, acetate (or other carboxylate), trifluoroacetate, phosphate, hydrogen phosphate, carbonate, sulfate, nitrite, cyanide, cyanate, thiocyanate, $IO_3$, $BrO_3$, $ClO_3$, oxalate, and hydroxide.

The catalyst can include a ligand, L, in the condition where [L]$_1$. No ligand, L, is present when [L]$_0$. When no L is present, the oxidation state is I and the catalyst is neutral.

The ligand, L, is an anion or a molecule of a solvent. The bonding dynamics between M, the solvent, and anions within the solvent, dictate whether L is an anion or a molecule of a solvent. The primary factor in whether an anion binds or a solvent molecule binds is the propensity of the anion to coordinate to M. For example, the borate anions do not coordinate strongly, so in that case a solvent molecule coordinates and the borate remains in an ion pair. But anions such as chloride, bromide, and acetate can more readily bind to M and so often those become L instead of the solvent.

When L is an anion, representative anions include hydrogen, Cl, Br, I, $CF_3SO_3$, $SO_4$, hydroxide, $ClO_4$, acetate (or other carboxylate), nitrate, trifluoroacetate, phosphate, and hydrogen phosphate. When L is a molecule of a solvent, representative solvent molecules include water, acetone, acetonitrile, alcohols (e.g., methanol, ethanol, propanol, butanol, tert-butanol, trifluoroethanol, etc.), tetrahydrofuran (THF), 2-methylTHF, ethers (e.g., diethyl ether, dimethoxyethane, methoxyethanol, etc.), dioxane, dimethylformamide (DMF), dimethyl sulfoxide (DMSO), gamma-valerolactone, nitromethane, arenes (e.g., benzene, mesitylene, xylenes, etc.), dichloromethane, dichloroethane, and chloroform.

Depending upon the valence state of M, the presence or absence of L, and the charge of L, if present, the catalyst can be a neutral molecule with a net charge of zero or a cation.

Representative neutral catalysts include Cp*Ir(bpy)SO$_4$ and Cp*Ir(bpy). Representative cationic catalysts are disclosed throughout the application and Examples, including [Cp*Ir(bpy)(OH$_2$)]$^{2+}$, [Cp*Ir(bpy)(Cl)]$^+$, and [Cp*Ir(MeO-bpy)(OH$_2$)]$^{2+}$ (where MeO-bpy=4,4'-dimethoxy-2,2'-bipyridine).

In certain embodiments, the catalysts include a bipyridine ("bpy") ligand. Suitable bipyridine ligands include substituted and unsubstituted bipyridine ligands. In one embodiment, the bipyridine is a 2,2'-bipyridine. An unsubstituted bipyridine ligand has hydrogen at each position. The bipyridine ligand can be substituted at one or more positions with one or more substituents. For a bipyridine ligand substituted with more than one substituent, the substituents may the same or different. The bipyridine ligand can be substituted at any position so long as the substitution does not limit the ligands ability to form a stable complex with the metal center, M. In one embodiment, the bipyridine is disubstituted. In one embodiment, the bipyridine is symmetrically disubstituted (e.g., 4,4'-disubstituted-2,2'-bipyridine). In one embodiment the bipyridine is substituted at the ortho position and/or para position.

In certain embodiments, the catalyst includes a phenanthroline ("phen") ligand. Suitable phenanthroline ligands include substituted and unsubstituted phenanthroline ligands. In one embodiment, the phenanthroline is a 1,10-phenanthroline. An unsubstituted phenanthroline ligand has hydrogen at each position. The substituted phenanthroline ligand can be substituted at one or more positions with one or more substituents. For a phenanthroline ligand substituted with more than one substituent, the substituents may the same or different. The phenanthroline ligand can be substituted at any position so long as the substitution does not limit the ligands ability to form a stable complex with the metal center, M. In one embodiment, the phenanthroline is di-substituted. In one embodiment, the phenanthroline is symmetrically di-substituted (e.g., 4,7-di-substituted-1,10-phenanthroline; 5,6-di-substituted-1,10-phenanthroline; and 2,9-di-substituted-1,10-phenanthroline).

Suitable bipyridine or phenanthroline substituents include substituted or unsubstituted hydroxy, alkyl ester, aryl ester, alkyl, aryl, arylalkyl, alkenyl, alkoxy, amino, alkylamino, dialkylamino, and halogen. In one embodiment, the substituent is a methoxy group (e.g., 4,4'-methoxy-2,2'-bipyridine). In one embodiment, the substituent is a hydroxy group (e.g., 4,4'-hydroxy-2,2'-bipyridine, 6,6'-hydroxy-2,2'-bipyridine, and 2,9-hydroxy-1,10-phenanthroline). In one embodiment the bipyridine is unsubstituted. in one embodiment the phenanthroline is unsubstituted.

In certain embodiments the catalysts includes a substituted or unsubstituted cyclopentadienyl ligand, Cp. An unsubstituted cyclopentadienyl ligand has hydrogen at each position. The substituted cyclopentadienyl ligand can be substituted at one or more positions with one or more substituents. For a cyclopentadienyl ligand substituted with more than one substituent, the substituents may the same or different. The cyclopentadienyl ligand can be substituted at any position so long as the substitution does not limit the ligands ability to form a stable complex with the metal center, M. In one embodiment, the cyclopentadienyl is mono-substituted (e.g. methylcyclopentadiene). In one embodiment, the cyclopentadienyl is penta-substituted (i.e., at each position), such as 1,2,3,4,5-pentamethylcyclopentadienyl (referred to herein as "Cp*"). In one embodiment, the cyclopentadienyl is substituted at some, but not all, positions, such as 1-hydroxy-2,3,4,5-tetraphenyl-cyclopentadienyl.

Suitable cyclopentadienyl substituents include substituted or unsubstituted hydroxy, alkyl ester, aryl ester, alkyl, aryl, arylalkyl, alkenyl, alkoxy, amino, alkylamino, dialkylamino, silyl, and halogen.

The following definitions are provided to better understand the invention.

The term "alkyl", alone or as part of another group, refers to a monovalent alkane (hydrocarbon) derived radical containing from 1 to 12 carbon atoms unless otherwise defined. An alkyl group is an optionally substituted straight, branched, or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to, one or more of the following groups: halo (such as F, Cl, Br, I), haloalkyl (such as —CCl$_3$ or —CF$_3$), alkoxy, alkylthio, hydroxy, carboxy (—COOH), alkyloxycarbonyl (—C(O)R), alkylcarbonyloxy (—OCOR), amino (—NH$_2$), carbamoyl (—NHCOOR— or —OCONHR—), urea (—NHCONHR—), or thiol (—SH). Alkyl groups as defined may also comprise one or more carbon to carbon double bonds or one or more carbon to carbon triple bonds. The alkyl group may also be a cycloalkyl group.

The term "silyl", alone or as part of another group, refers to a group containing at least one silicon linkage —SiR, wherein R can be alkyl, aryl, or other functional group defined herein.

The term "alkenyl", alone or as part of another group, refers to a hydrocarbon radical straight, branched or cyclic containing from 2 to 12 carbon atoms and at least one carbon to carbon double bond.

The numbers in the subscript after the symbol "C" define the number of carbon atoms a particular group can contain. For example "C1-6 alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "C1-6 alkyl" can also refer to C1-6 alkylene which bridges two groups; examples include propane-1,3-diyl, butane-1,4-diyl, 2-methyl-butane-1,4-diyl. "C2-6 alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "C2-6 alkenyl" can also refer to C2-6 alkenediyl which bridges two groups; examples include ethylene-1,2-diyl (vinylene), 2-methyl butene-1,4-diyl, 2-hexene-1,6-diyl.

The terms "alkoxy" or "alkylamino", alone or as part of another group, denote an alkyl group as described above bonded through an oxygen linkage (—O—) or a nitrogen linkage (—N—), respectively.

The term "arylalkyl", alone or as part of another group, denotes an aromatic ring bonded to an alkyl group as described above.

The term "aryl", alone or as part of another group, refers to monocyclic or bicyclic aromatic rings, e.g., phenyl, substituted phenyl, and the like, as well as groups which are fused, e.g., napthyl, phenanthrenyl, and the like. An aryl group thus contains at least one ring having at least 6 atoms, with up to five such rings being present, containing up to 22 atoms therein, with alternating double bonds between adjacent carbon atoms or suitable heteroatoms. Aryl groups may optionally be substituted with one or more groups including, but not limited to, halogen, alkyl, alkoxy, hydroxy, carboxy, carbamoyl, alkyloxycarbonyl, nitro, trifluoromethyl, amino, cycloalkyl, cyano, alkyl S(O)$_m$ (m=0, 1, 2), or thiol.

The term "cycloalkyl", alone or as part of another group, refers to fully saturated and partially unsaturated hydrocarbon rings of 3 to 9, preferably 3 to 7 carbon atoms. A cycloalkyl may be substituted. A substituted cycloalkyl refers to such rings having one, two, or three substituents, preferably one selected from the group consisting of halo, alkyl, substituted alkyl, alkenyl, alkynyl, nitro, cyano, oxo (=O), hydroxy, alkoxy, thioalkyl, —CO$_2$H, —C(=O)H, CO$_2$-alkyl, C(=O)alkyl, keto, =N—OH, =N alkyl, aryl, heteroaryl, heterocyclo, a five or six membered ketal (e.g., 1,3-dioxolane or 1,3-dioxane), —NR'R", —C(=O)NR'R", —CO$_2$NR'R", —NR'CO$_2$R", —NR'C(=O)R", —SO$_2$NR'R", and NR'SO$_2$R", wherein each of R' and R" is independently selected from hydrogen, alkyl, substituted alkyl, and cycloalkyl, or R' and R" together form a heterocyclo or heteroaryl ring.

The term "heteroaryl", alone or as part of another group, refers to substituted and unsubstituted aromatic 5 or 6 membered monocyclic groups, 9 or 10 membered bicyclic groups, and 11 to 14 membered tricyclic groups which have at 6 least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups that are bicyclic or tricyclic must include at least one fully aromatic ring, but the other fused ring or rings may be aromatic or nonaromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —CO₂H, —C(=O)H, —CO₂alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —CO₂NR'R", —C(=O)NR'R", —NR'CO₂R", —NR'C(=O)R", —SO₂NR'R", and —NR'SO₂R", wherein each of R' and R" is independently selected from hydrogen, alkyl, substituted alkyl, and cycloalkyl, or R' and R" together form a heterocyclo or heteroaryl ring. Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, faranyl, thienyl, oxadiazolyl, pyridyl, pyrazinyl, pyrimidinyl, pyridazinyl, triazinyl and the like. Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like. Exemplary tricyclic heteroaryl groups include carbazolyl, benzidolyl, phenanthrollinyl, acridinyl, phenanthridinyl, xanthenyl and the like.

The term "halogen" or "halo" refers to chlorine, bromine, fluorine or iodine selected on an independent basis.

The term "amino", alone or as part of another group, refers to —NH₂. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl, or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

Hydrogenation Catalysis

The above-described catalysts can be used to facilitate hydrogenation of a substrate when in the presence of dihydrogen. The provided catalytic methods have been demonstrated to perform the hydrogenation reaction in conditions significantly milder (e.g., lower temperature and hydrogen pressure) than those of the prior art.

In one aspect, a method of hydrogenating a substrate is provided. In one embodiment, the method comprising exposing the substrate and a catalyst to hydrogen gas; wherein the catalyst is selected from the group consisting of:

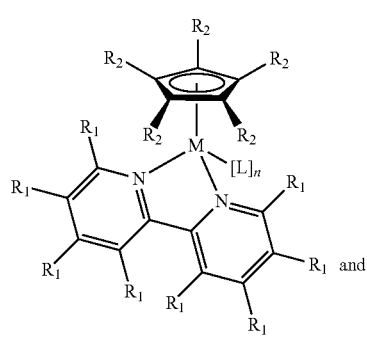

and

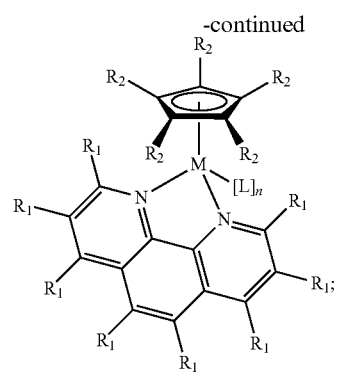

wherein M is selected from the group consisting of Ir and Rh;

wherein n is 0 or 1;

wherein when n is 1 L is selected from the group consisting of an anion and a molecule of a solvent;

wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

In another aspect, a method of hydrogenating a substrate, comprising exposing the substrate and a catalyst to hydrogen gas, wherein the catalyst comprises:

CpM(N—N)L$_n$;

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

In one embodiment, the catalyst is a neutral compound.

In one embodiment, the catalyst is a cation. In one embodiment, the catalyst has a charge of +1 or +2. In one embodiment, one or more anions are associated with the catalyst. In one embodiment, the anion is selected from the group consisting of triflate, PF₆, chloride, BF4, triflamide, tetraphenylborate, iodide, bromide, tetrafluorophenylborate, tetrakis[3,5-bis(trifluoromethyl)phenyl]borate, SbF₆, NO₃, ClO₄, tosylate, acetate (or other carboxylate), trifluoroacetate, phosphate, hydrogen phosphate, carbonate, sulfate, nitrite, cyanide, cyanate, thiocyanate, IO₃, BrO₃, ClO₃, oxalate, and hydroxide. In one embodiment, L is an anion selected from the group consisting of hydrogen, Cl, Br, I, CF₃SO₃, SO₄, tosylate, hydroxide, ClO₄, acetate (or other carboxylate), nitrate, trifluoroacetate, phosphate, and hydrogen phosphate.

In the disclosed methods, the catalyst is used to hydrogenate a substrate. As used herein, the term "hydrogenate" refers to a chemical reaction between dihydrogen and a substrate, typically resulting in a reduction of the substrate. An exemplary hydrogenation according to the disclosed embodiments is the hydrogenation of carboxylic acids to alcohols. Exemplary hydrogenation catalysis methods are disclosed extensively in Example 1 below.

The method proceeds by exposing a substrate and a catalyst to dihydrogen (e.g., hydrogen gas). As used herein, the term "exposing" refers to a reaction condition wherein hydrogen contacts or is otherwise in the presence of the substrate and the catalyst.

Representative substrates include a carboxylic acid, a carbonate, and an ester.

Representative carboxylic acids include aromatic carboxylic acids and aliphatic carboxylic acids. Representative aliphatic carboxylic acids include acetic acid, propionic acid, butyric acid, and levulinic acid. Representative aromatic carboxylic acids include benzoic acid and terephthalic acid.

Representative esters include cyclic esters, aliphatic esters, and aromatic esters. In one embodiment, the ester is selected from the group consisting of gamma-valerolactone, delta-valerolactone, gamma-butyrolactone, ethyl formate, ethyl acetate.

Representative carbonates include dialkyl, diaryl and cyclic carbonates. In one embodiment the carbonate is dimethyl carbonate or propylene carbonate.

As used herein, the combination of the substrate and the catalyst can be referred to as a "mixture" (e.g., a reaction mixture). The term mixture does not describe the reaction mixture as homogeneous or heterogeneous, but only describes the presence of at least the substrate and the catalyst.

In certain embodiments, the mixture additionally includes a solvent that solvates the substrate. Representative solvents include water, acetone, acetonitrile, alcohols (e.g., methanol, ethanol, propanol, butanol, tert-butanol, trifluoroethanol, etc.), THF, 2-methylTHF, ethers (e.g., diethyl ether, dimethoxyethane, methoxyethanol, etc.), dioxane, DMF, DMSO, gamma-valerolactone, nitromethane, arenes (e.g., benzene, mesitylene, xylenes, etc.), dichloromethane, dichloroethane, and chloroform. In one embodiment, the solvent is water.

In certain embodiments, the solvent also solvates the catalyst. Therefore, in such embodiments the catalyst is a homogeneous catalyst.

In other embodiments the catalyst is a heterogeneous catalyst. A heterogeneous catalyst is not solvated by the substrate or solvent. Typically, a heterogeneous catalyst according to the disclosed embodiments comprises a substrate to which the catalyst is attached. The substrate is flowed past the catalyst substrate in the presence of hydrogen in order to complete the hydrogenation reaction. The attachment of a typically homogeneous catalyst, such as those disclosed herein, to a substrate in order to heterogenize it is known to those of skill in the art. For example, the catalyst can be reductively electropolymerized to form a heterogeneous catalyst material (e.g., *J. Electroanal. Chem.* 1993, 352, 213); or a silica-based support could be used to heterogenize the catalyst (e.g., *ACS Catalysis*, 2013, 3, 655).

In one embodiment, the exposing step takes place under acidic conditions. As discussed further in Example 1, decreased pH leads to increased turnover numbers for the reaction. As used herein, the term "acidic conditions" refers generally to a pH of less than 7. In one embodiment, the pH of the reaction mixture is less than 4. In another embodiment, the pH of the reaction mixture is less than 1. In one embodiment, the solvent is water and the pH of the reaction mixture is less than 1.

In one embodiment, the solvent is not water, and acidity is derived from a Brønsted or Lewis acid. Representative Lewis acids include lithium, sodium, potassium, barium, zinc, and scandium (all as their triflate salts). Generally, any alkali or alkaline earth cation, as well as any lanthanide ion can be used as a Lewis acid. Brønsted acids include triflic acid, fluoroboric acid, sulfuric acid, phosphoric acid, nitric acid, hydrochloric (and HF/HBr/HI), perchloric acid, $H(Et_2O)+B(3,5-bis(trifluoromethyl)phenyl)_4^-$.

In certain embodiments the mixture contains no solvent. In this embodiment, the only liquid in the reaction mixture is the substrate. This state may also be referred to as when the "substrate is the solvent." In this regard, the substrate may still solvate the catalyst in a reaction mixture that contains "no solvent."

In the method hydrogen gas is exposed to the mixture, typically in a reaction vessel configured to contain the substrate in liquid form and the catalyst. Representative vessels are formed from steel or glass.

In one embodiment, the hydrogen gas has a pressure from 1 atm to 100 atm. Accordingly, in certain embodiments, the reaction vessel is configured to withstand the elevated pressure of the hydrogen gas. In one embodiment, the hydrogen gas has a pressure from 3 atm to 60 atm. As discussed further in Example 1, increased hydrogen gas pressure leads to increased turnover numbers for the reaction.

In one embodiment, the method further comprises a step of heating. As discussed further in Example 1, increased heat leads to increased turnover numbers for the reaction. However, the temperature must be moderated in order to avoid decomposing the catalyst. Such a heating step can improve the efficiency of the catalysis and decrease the time required for the reaction to proceed. In one embodiment, heating comprises heating to a temperature of 20° C. to 130° C. In one embodiment, heating comprises heating to a temperature of 80° C. to 120° C.

Generally, increased catalyst loading and substrate loading increases reaction rates, although at catalyst concentrations above 4 mM the catalyst decomposition rate begins to increase.

In one embodiment, the concentration of catalyst is from 0.5 mM to 4 mM. In one embodiment, the concentration of catalyst is 1 mM or less. Concentrations of catalyst as low as 0.5 mM have been found to be effective.

In one embodiment, the concentration of the substrate is from 0.5 M to neat. Each substrate will have a different neat concentration (e.g., 17.45 M for acetic acid). After the hydrogenation process has completed, some percentage of the substrate is hydrogenated. As will be discussed further in Example 1, the efficacy of the hydrogenation can be assessed using the calculated turnover number (TON).

Disproportionation Catalysis

The above-described catalysts can also be used to catalyze disproportionation of formic acid in order to generate methanol and methyl formate. This method is of particular interest because it facilitates the conversion of formic acid to methanol and therefore provides a renewable route to a major commodity chemical and a high energy density fuel.

Examples of the disproportionation catalysis method are discussed in Example 2.

In one aspect, a method of forming methanol and methyl formate is provided. In one embodiment, the method comprises contacting formic acid with a catalyst selected from the group consisting of:

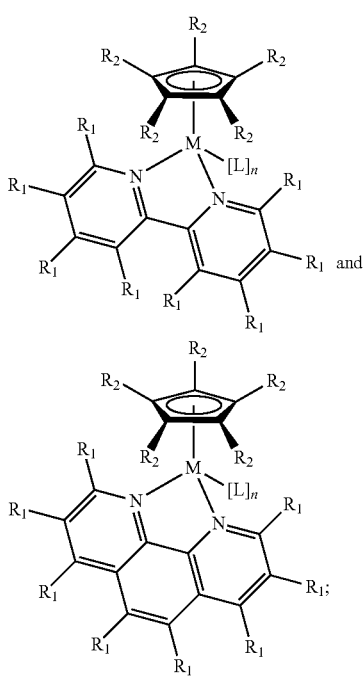

wherein M is selected from the group consisting of Ir and Rh;

wherein n is 0 or 1;

wherein when n is 1 L is selected from the group consisting of an anion and a molecule of a solvent;

wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

In another aspect, a method of forming methanol and methyl formate is provided. In one embodiment the method comprises contacting formic acid with a catalyst comprising:

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

In one embodiment, the catalyst is a neutral compound.

In one embodiment, the catalyst is a cation. In one embodiment, the catalyst has a charge of +1 or +2. In one embodiment, one or more anions are associated with the catalyst. In one embodiment, the anion is selected from the group consisting of triflate, $PF_6$, chloride, fluoride, formate, $BF_4$, triflamide, tetraphenylborate, iodide, bromide, tetrafluorophenylborate, tetrakis[3,5-bis(trifluoromethyl)phenyl]borate, $SbF_6$, $NO_3$, $ClO_4$, tetrakis(pentafluorophenyl)borate, tosylate, acetate (or other carboxylate), trifluoroacetate, phosphate, hydrogen phosphate, carbonate, sulfate, nitrite, cyanide, cyanate, thiocyanate, $IO_3$, $BrO_3$, $ClO_3$, oxalate, and hydroxide.

In one embodiment, L is an anion selected from the group consisting of hydrogen, Cl, Br, I, $CF_3SO_3$, $SO_4$, hydroxide, $ClO_4$, acetate (or other carboxylate), nitrate, trifluoroacetate, phosphate, and hydrogen phosphate.

In one embodiment, L is water.

In the disclosed methods, the catalyst is used to disproportionate formic acid to form methanol and methyl formate. Therefore, formic acid is the substrate on which the catalyst acts.

The method proceeds by contacting formic acid (i.e., a substrate) with the catalyst. As used herein, the term "contacting" refers to a reaction condition wherein the substrate is in contact with the catalyst (e.g., as part of a homogeneous mixture).

As used herein, the combination of the formic acid (i.e., substrate) and the catalyst can be referred to as a "mixture" (e.g., a reaction mixture). The term mixture does not describe the reaction mixture as homogeneous or heterogeneous, but only describes the presence of at least the substrate and the catalyst.

In certain embodiments, the mixture additionally includes water as a solvent that solvates the substrate. Addition of water decreases the concentration of formic acid and also alters the pH.

In certain embodiments, the formic acid and an any optional water solvent also solvates the catalyst. Therefore, in such embodiments the catalyst is a homogeneous catalyst.

In certain embodiments the mixture contains no solvent. In this embodiment, the only liquid in the reaction mixture is the substrate. This state may also be referred to as when the "substrate is the solvent." In this regard, the substrate may still solvate the catalyst in a reaction mixture that contains "no solvent."

In other embodiments the catalyst is a heterogeneous catalyst, as disclosed above with regard to hydrogenation catalysis.

In one embodiment, the contacting step takes place under acidic conditions. As discussed further in Example 2, decreased pH leads to increased turnover numbers for the reaction. As used herein, the term "acidic conditions" refers generally to a pH of less than 7. In one embodiment, the pH of the reaction mixture is less than 4. In another embodiment, the pH of the reaction mixture is less than 1. In one embodiment, the solvent is water and the pH of the reaction mixture is less than 1.

In one embodiment, the concentration of the formic acid is from 0.5 M to 23.4 M. In one embodiment, the concentration of the formic acid is from 0.5 M to 12 M. As discussed further in Example 2, increased formic acid concentration leads to increased turnover numbers for the reaction and increased methanol selectivity.

In one embodiment, the method further comprises a step of heating. Such a heating step can improve the efficiency of the catalysis and decrease the time required for the reaction to proceed. As discussed further in Example 2, increased heating leads to increased turnover numbers for the reaction and increased conversion rates. In one embodiment, heating comprises heating to a temperature of 20° C. to 120° C. In one embodiment, heating comprises heating to a temperature of 80° C. to 120° C.

In further embodiments, the method comprises the addition of hydrogen gas to the reaction. Hydrogen gas has the effect of improving the yield of methanol, as illustrated in Example 2 (e.g., under 30 atm of hydrogen gas the selectivity for methanol almost doubles compared to the reaction without hydrogen). In one embodiment, the hydrogen gas has a pressure from 1 atm to 100 atm. In one embodiment, the hydrogen gas has a pressure from 3 atm to 60 atm.

Side products of $H_2$ and $CO_2$ are typically generated during the method. Minimization of these side products is desirable, as they represent lost efficiency in the generation of methanol. The reaction conditions affect the generation of these side products. For example, increased concentrations of formic acid and the presence of $H_2$ gas both help to minimize the amount of $H_2$ and $CO_2$ produced, and therefore maximize the amount of methanol produced. Using the methods disclosed herein, methanol yields of 12% were achieved, as described in Example 2.

A typical reaction is completed in about 24 hours. After the disproportionation reaction has completed, methanol and methyl formate are provided. As will be discussed further in Example 2, the efficacy of the disproportionation can be assessed using turnover number (TON), turnover frequency (TOF), and methanol selectivity.

The following examples are provided for the purpose of illustrating, not limiting, the invention.

EXAMPLES

Example 1

Hydrogenation Catalysis

Reduction of carboxylic acids to alcohols is a fundamental transformation in organic chemistry. Traditionally, this reaction has been carried out using stoichiometric quantities of strong reducing agents such as lithium aluminum hydride or lithium triethylborohydride. The use of stoichiometric amounts of strong reductants is undesirable due to issues of reagent compatibility and the poor atom economy of the overall transformation.

An attractive alternative would be the direct hydrogenation of the carboxylic acid by dihydrogen. Unfortunately, carboxylic acids are among the most difficult carbonyl substrates to hydrogenate due to the low electrophilicity of the carbonyl carbon. It is unsurprising, therefore, that to date only two homogeneous systems for acid hydrogenation have been reported, both of which operate under relatively forcing conditions. Frediani and coworkers reported a series of ruthenium carbonyl-hydride clusters capable of hydrogenative coupling of various carboxylic acids to produce alkyl esters at 180° C. under 130 atm of $H_2$. More recently, Leitner and coworkers reported a ruthenium tris-phosphine catalyst capable of hydrogenating bio-derived acids such as levulinic acid and itaconic acid. Depending on the reaction conditions (typically 100 atm $H_2$, 160° C., Brønsted acid promoter) a variety of reduced products were formed, including lactones, alcohols, diols, and substituted tetrahydrofurans.

We report below in Example 2 that formic acid can be reduced to methanol via an apparent transfer hydrogenation mechanism in which formic acid acts as both the hydrogen donor and acceptor. This catalytic disproportionation of formic acid is competitive with the more common dehydrogenation pathway—selectivity for methanol and methyl formate could be pushed as high as 12%. The maximum theoretical yield of methanol is 33% based on the reaction stoichiometry of disproportionation (as described in Example 2, Eq. 4).

Mechanistic studies suggest that the catalyst [Cp*Ir(bpy)(OH$_2$)][OTf]$_2$ (bpy=2,2'-bipyridine, OTf=trifluoromethanesulfonate), (1) was converted to [Cp*Ir(bpy)(H)][OTf] (2) during turnover; hydride transfer from 2 to protonated formic acid appears to be an important step in the reaction. Hydride 2 has also been implicated in hydrogenation reactions using $H_2$ directly, most notably in the hydrogenation of $CO_2$ to formic acid. It seemed likely, therefore, that replacement of formic acid by $H_2$ might facilitate hydrogenation of a wide range of carboxylic acid substrates while avoiding competitive decomposition pathways. Here we report that 1 and related homogeneous catalysts readily hydrogenate aliphatic carboxylic acids under the mildest conditions yet reported.

We began our investigation of direct hydrogenation of carboxylic acids by 1 using acetic acid as substrate. Glacial acetic acid solutions containing 2 mM 1 were pressurized with 30 atm $H_2$ and heated to 120° C. After 65 hours, ethyl acetate was observed to be the major product by GC-FID (approx. 42:1 ethyl acetate:ethanol vs. dioxane internal standard), as outlined in FIG. 1. Reactions in glacial acetic acid consistently produced reductively coupled ester products with high selectivity (>95%). No additional products are observed under these conditions.

Preliminary mechanistic studies were undertaken in order to understand and optimize the reaction. Reaction rates were assessed from the turnover number [Turnover numbers were calculated by dividing the combined moles of all hydrogenation products by the moles of catalyst. One turnover is required to produce ethanol (and the subsequently esterified product, ethyl acetate). Two turnovers are required to produce the two ethanol molecules that couple to produce diethyl ether.] (TON) after 65 hours (up to 30% conversion). Measurements at relatively low conversion are required to avoid rate effects due to reaction inhibition by water (vide infra). [Turnover frequencies after 18 h were similar to turnover frequencies after 65 h (Catalyst 5: Table 1 and Table 4).] A direct temperature dependence was observed with the TON increasing from 73 at 60° C. to 425 at 120° C. after 65 hours. Unfortunately, at temperatures above 120° C., some catalyst decomposition was observed as evidenced by the deposition of iridium black on the reactor liners and irreproducible reaction rates. The heterogeneous decomposition products were subsequently tested and found to be inactive toward catalyzing the hydrogenation reaction.

The rate of hydrogenative coupling of acetic acid was found to be first order in both substrate and catalyst at 120° C., and saturation behavior was observed with respect to the pressure of $H_2$ (FIG. 2). Addition of water to the reaction dramatically slowed the rate. In 8.7 M acetic acid only 26 turnovers had occurred after 65 hours. Conversely, in the presence of added HBF$_4$ (8.7 M acetic acid in a 1:1 (w:w) H$_2$O:HBF$_4$ solution), the rate increased markedly to 1338 turnovers after 65 hours, as shown in FIG. 1. Under such conditions (higher concentrations of water and protons) the distribution of products begins to shift: diethyl ether was now observed as a minor product, and more ethanol was present. The product distribution was 8:13:1 (ethanol:ethyl acetate:diethyl ether). This is unsurprising, as esterification to ethyl acetate should be less favored in the presence of excess water. The diethyl ether is presumably formed through an acid-catalyzed dehydrative homocoupling of ethanol. These results illustrate that product selectivity may be tuned by changing the acid concentration in aqueous solvent.

Figure 3:
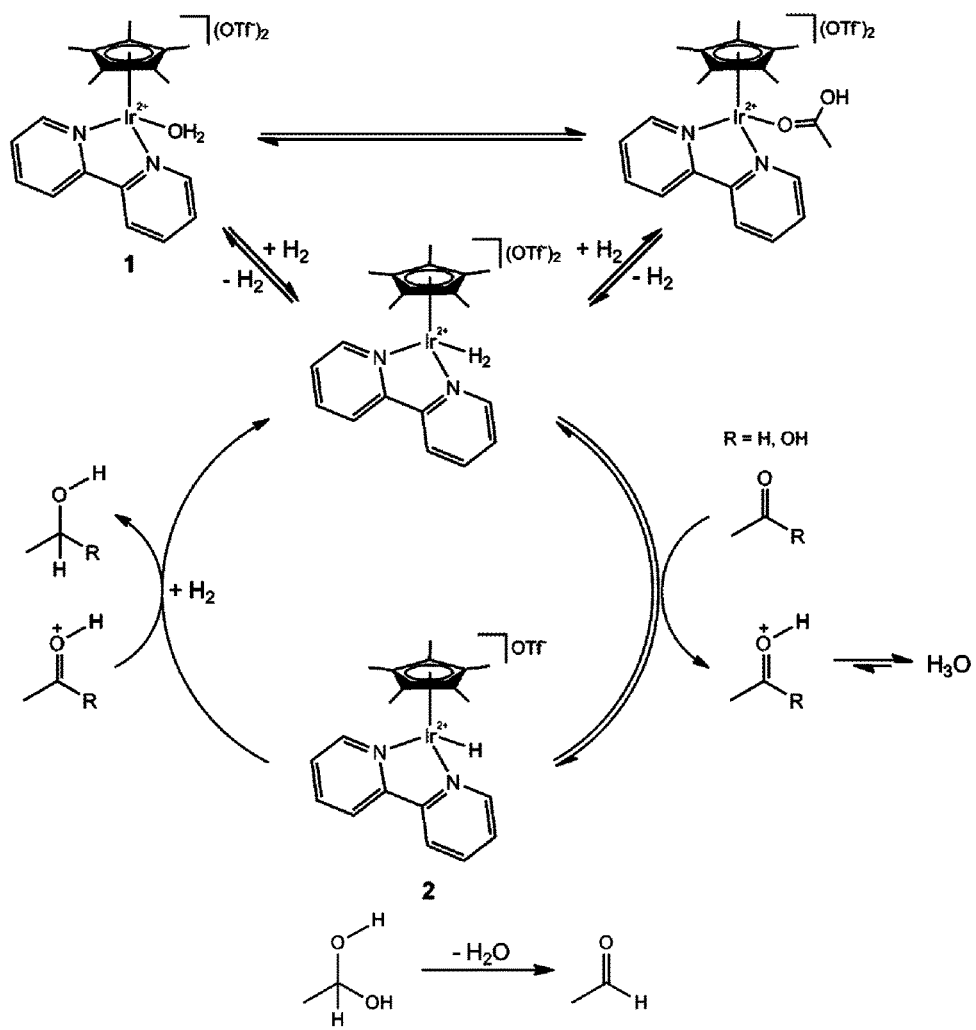
FIG. 3. Proposed hydrogenation reaction mechanism in accordance with embodiments disclosed herein.

A reaction mechanism consistent with the above data is shown in FIG. 3. An initial equilibrium between aqua complex 1, acetic acid complex [Cp*Ir(bpy)(HOAc)][OTf]$_2$, and dihydrogen complex [Cp*Ir(bpy)(H$_2$)][OTf]$_2$ is established. Such dihydrogen complexes are highly acidic, so rapid deprotonation to form 2 would be expected. This pre-equilibrium is consistent with the observed $H_2$ saturation kinetics. At sufficiently high pressure, formation of the dihydrogen complex is favored, leading to rapid formation of 2 and rate-limiting hydride transfer that does not depend on $H_2$ pressure. After protonation of acetic acid, 2 transfers a hydride to the activated acetic acid molecule producing acetaldehyde and then rejoins the equilibria between dicationic Ir species. The proposal that the reaction involves protonated acetic acid is consistent with our observations involving aqueous dilution; the concentration of protonated acetic acid drops significantly in the presence of water which is more basic ($pK_a(H_3O^+$ (aq.))=–1.7, $pK_a(CH_3CO_2H_2^+$ (aq.))=–6.1). Further, addition of strong acid accelerates the reaction.

The acetaldehyde produced after one hydrogenation cycle would then be converted to ethanol following a similar mechanism. No aldehydes (or aldehyde hydrates) were observed, consistent with previous reports of rapid (transfer) hydrogenation of aldehydes under even milder conditions. Depending on conditions, the initial hydrogenation product ethanol can undergo either Fischer esterification with the acetic acid solvent to generate the hydrogenative coupling product ethyl acetate (the major product) or acid-catalyzed homocoupling to generate diethyl ether (a minor product observed under some reaction conditions).

To probe the intermediacy of iridium monohydride complex 2, the previously reported hydride was prepared and employed as the precatalyst. Interestingly, the reaction rate under the standard conditions was much slower when 2 was used instead of 1. We hypothesized that complex 1 effectively acts as a strong acid, as $[Cp*Ir(bpy)(H_2)]^{2+}$ quickly releases $H^+$ into solution to generate hydride 2 (FIG. 3). Accordingly, reactions catalyzed by a combination of 2 and HOTf (1 μL, 3 eq.) gave similar rates to reactions catalyzed by 1. These results confirm the viability of complex 2 as an intermediate in the hydrogenation reaction.

Notably, the known iridium chloride complex $[Cp*Ir(bpy)Cl][Cl]$ (3) shows no catalytic activity for acetic acid hydrogenation. This result contrasts the case of formic acid disproportionation, where complex 3 was shown to be a competent catalyst. The relatively non-polar glacial acetic acid solvent ($\epsilon$=6.1) may inhibit chloride dissociation and prevent formation of the key hydride intermediate. The simple chloride-bridged dimer $[Cp*IrCl_2]_2$ (4) was also tested, but only traces of product—and large amounts of iridium black—were observed.

Figure 4:
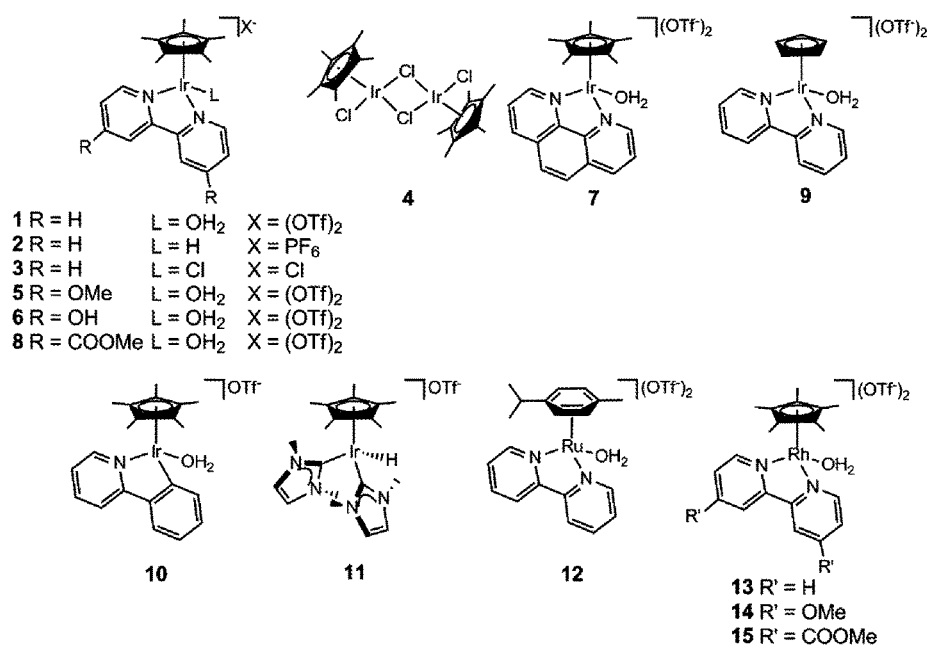
FIG. 4. Catalysts screened for AcOH hydrogenation in exemplary embodiments of the disclosure.

The above mechanistic studies suggest that under sufficient $H_2$ pressure hydride transfer is involved in the rate limiting step. Thus, increasing the hydricity of this intermediate should increase the rate of reaction. A series of structurally related catalysts with varying electronic properties were therefore investigated (FIG. 4). All catalysts were tested for activity in glacial acetic acid at 120° C. under 27 atm $H_2$ (above the $H_2$ saturation pressure), mild conditions compared to related previous literature reports. The results are summarized in Table 1. Catalysts bearing bipyridyl ligands with electron donating groups in the 4 and 4' positions (OH, 5, and OMe, 6) show markedly increased reaction rates when compared to bpy itself, consistent with our hypothesis that hydride donor ability is an important factor. The phenanthroline complex, 7, showed nearly identical activity to 1. In contrast, catalyst 8, featured electron-withdrawing methyl ester groups and showed essentially no activity. Replacing Cp* with the unsubstituted Cp ligand (complex 9) also led to a decrease in rate. No decomposition to Ir black was observed in any of these reactions.

Noticing that more electron-rich complexes were better catalysts, we sought other viable catalysts supported by strong donor ligands. The previously reported phenylpyridine complex 10 and bis(N-heterocyclic carbene) complex 11 seemed promising, and the hydrogenation reactivity of these species was investigated. Interestingly, these complexes showed little activity at 120° C. and a large amount of iridium black was observed following reactions.

Half-sandwich complexes of alternative metals were also explored as catalysts for this reaction. First, an analogous half-sandwich ruthenium complex, 12, was investigated. While similar complexes are highly active toward asymmetric hydrogenation of ketones, 12 showed no activity for acetic acid hydrogenation. In contrast the rhodium complex 13, $[Cp*Rh(bpy)(OH_2)][OTf]_2$, was found to be a competent precatalyst for this reaction, albeit at a slower rate than its iridium analogue. $[Cp*Rh(bpy-OMe)(OH_2)][OTf]_2$, 14, and $[Cp*Rh(bpy-COOMe)(OH_2)][OTf]_2$, 15, were also found to be active precatalysts. Surprisingly, Rh and Ir exhibit opposite trends in terms of how the ligand donating ability affects the reactivity of the catalyst. For Rh, the more electron donating ligand of catalyst 14 showed the lowest turnover frequency while catalyst 15 with electron withdrawing ester groups exhibited the highest activity.

TABLE 1

Comparison of acetic acid hydrogenation catalysts.[a,b]

| Cat. | TON ± dev. |
| --- | --- |
| 1 | 425 ± 8 |
| 2 | 41 ± 12 |
| 2[c] | 503 ± 34 |
| 5 | 777 ± 15 |
| 5[d] | 1637 ± 25 |
| 6 | 615 ± 50 |
| 7 | 389 ± 56 |
| 8[e] | 9 |
| 9[e] | 40 |
| 12[e] | 21 |
| 13 | 96 ± 5 |
| 14 | 56 ± 1 |
| 15 | 125 ± 23 |
| None | Trace |

[a]For full table see Table 3.
[b]Average of 3 trials with calculated standard deviation. 2 mM catalyst in glacial acetic acid, 27 atm $H_2$, 120° C., 65 h.
[c]5 mM HOTf.
[d]16 mM Sc(OTf)$_3$ added.
[e]Average of two trials.

Figure 12:
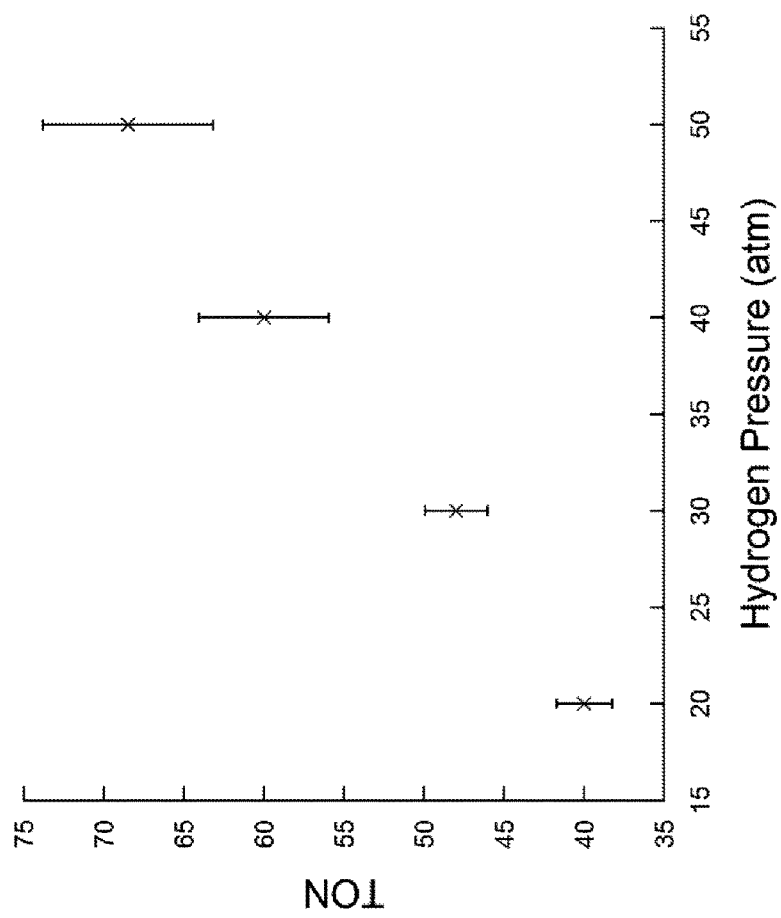
FIG. 12. Hydrogen pressure dependence of acetic acid hydrogenation. 2 mM catalyst 13 in glacial acetic acid, 120° C., 18 h.

This difference between Rh and Ir may be explained by a change in the resting state in the mechanism proposed in FIG. 3. For both metals, more strongly donating ligands should render the dihydrogen complex less acidic. For Ir, the saturation kinetics of FIG. 2C suggest that above ~30 atm $H_2$ the limiting step involves hydride transfer, which would be accelerated by more strongly donating ligands that render hydride 2 a stronger $H^-$ donor. For Rh catalyst 13, saturation kinetics were not observed up to an $H_2$ pressure of 50 atm (FIG. 12). In this case, the deprotonation of the Rh dihydrogen complex to generate the Rh hydride is involved in the rate law, and the aforementioned slowing of proton loss with more donating ligands would be expected. This leads to lower concentrations of rhodium hydride and activated acetic acid in solution, decreasing the catalytic rates.

As mentioned previously, our mechanistic proposal suggests that at pressures where the reaction is pseudo-zero-order in $H_2$, hydride transfer to a protonated substrate is rate limiting. We have already seen that increasing the proton concentration increases the reaction rate. By analogy, Lewis acid activation of the carbonyl could be expected to accelerate the reaction. Indeed, addition of NaOTf, Zn(OTf)$_2$, or Sc(OTf)$_3$ resulted in a twofold rate enhancement over reactions lacking these promoters (for full list of screened Lewis acids see Table 4). A specific interaction of the Lewis acid with the carbonyl is implied by the complete suppression of the acid effect when 15-crown-5 was added to a reaction containing NaOTf. Under these conditions, turnover returned to the level observed in the absence of Lewis acids.

The hydrogenation of other carboxylic acids was also investigated. An experiment involving catalyst 1 in a mixture of 3 M formic acid (aq.) and 3 M acetic acid (aq.) yielded only methanol and methyl ester products, suggesting that carboxylic acids with shorter aliphatic carbon chains react more rapidly (consistent with previous observations). Indeed, using our most active catalyst 5, propionic acid and butyric acid were each hydrogenated in 3:1 H$_2$O:HBF$_4$ at diminished rates compared to acetic acid (Table 2). Reaction selectivity also changes from 2.5:1 ester:alcohol for acetic acid to 1:2 ester:alcohol for propionic and butyric acids. The observed decrease in reactivity is consistent with our proposed mechanism: as the size of the carboxylic acid increases from C$_1$ to C$_4$ the carboxylate carbon would be expected to become more electron-rich, and thus less susceptible to nucleophilic attack from the iridium hydride. The magnitude of the electronic effect would likely diminish with increasing aliphatic chain size, but this could not be directly verified due to limited substrate solubility in water. [Preliminary experiments investigating fluorinated alcoholic or ethereal solvents met with difficulties due to solvent decomposition and/or esterification with the carboxylic acid starting material. For example, in the case of 1,2-dimethoxyethane, large amounts of methyl ester were observed.]

The relative rates of aliphatic carboxylic acid hydrogenation were further probed through competition experiments. Equimolar mixtures of acetic acid and C$_3$ or C$_4$ acid were subjected to 30 atm H$_2$ in the presence of 2 mM 5 and 20 mM NaOTf for 18 h at 120° C. The trend in relative rates of hydrogenation observed in this experiment reflected the activity previously observed as displayed in the ratio of observed hydrogenation products (Table 2). Under these conditions, acetic acid was reduced with 6-fold selectivity over propionic acid and 10-fold selectivity relative to butyric acid.

TABLE 2

Comparing reactivity of aliphatic carboxylic acids.

| Substrate | Aqueous TON ± dev.[a] | AcOH Selectivity[b] |
|---|---|---|
| Acetic Acid | 68 ± 3 | 100% |
| Propionic Acid | 37 ± 1 | 87% |
| Butyric Acid | 21 ± 3 | 91% |

[a]3.5 mmol substrate and 4 μmol 5 in 2 mL 3:1 (v:v) H$_2$O:HBF$_4$, 30 atm H$_2$, 120° C., 18 h (three runs per substrate).
[b]2 mM 5, 20 mM NaOTf in 2 mL 1:1 (mol:mol) AcOH:substrate, 30 atm H$_2$, 120° C., 18 h (three runs per mixture). Selectivity calculated from the ratio of hydrogenated acetic acid to hydrogenated substrate.

Figure 5:
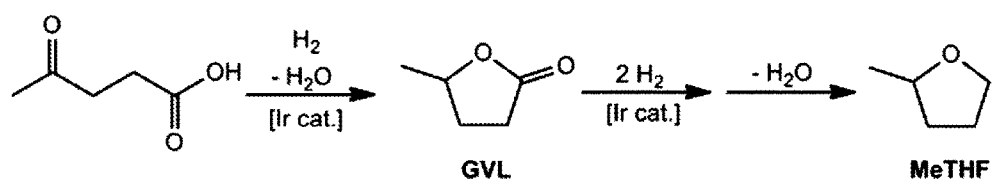
FIG. 5. Reaction sequence of hydrogenation of levulinic acid according to embodiments disclosed herein.

Finally, hydrogenation of levulinic acid was examined in order to make direct comparisons to the system recently reported by Leitner. Using an in situ generated Ru trisphosphine catalyst (0.1 mol % catalyst in 1,4-dioxane, 100 atm H$_2$, 160° C., 18 h), they reported 95% yield of 1,4-pentanediol (PDO), 3% γ-valerolactone (GVL, FIG. 5), and no 2-methyltetrahydrofuran (MeTHF). With the addition of 1 mol % p-toluenesulfonic acid, the products shifted to 39% MeTHF, 1% PDO and 58% GVL. [When a sulfonic acid containing ionic liquid rather than p-toluenesulfonic acid was added to the reaction mixture, 87% yield of MeTHF was obtained in addition to 1% PDO and 5% GVL.] At a lower temperature and pressure with catalyst 5 (0.08 mol % catalyst, 8 mol % HOTf, 30 atm H$_2$, 120° C., 18 h in 1,2-dimethoxyethane), we observed complete consumption of levulinic acid, a 90% yield of partially reduced GVL and a small amount (10% yield) of fully reduced MeTHF. Notably, no dehydration products are observed in our system.

In conclusion, we have demonstrated a novel system for catalytic hydrogenation of a variety of carboxylic acids. The proposed reaction mechanism (based on experimental evidence) guided optimization of the reaction, including the use of Lewis acid additives. The optimized catalyst system exhibits activity similar to previously published systems under significantly milder conditions.

Experimental Details

Synthesis

Procedures were performed using standard Schlenk techniques or in a nitrogen glovebox unless otherwise specified. Dichloromethane and diethyl ether were dried using a Grubbs-type solvent purification system. Methanol, acetic acid, and water were thoroughly degassed prior to use. Acetonitrile was purchased dry and dispensed in a glovebox. Isopropanol was dried over calcium hydride. Starting materials [Cp*IrCl$_2$]$_2$ (4), [Cp*RhCl$_2$]$_2$, [CpIrCl$_2$]$_n$, [(p-cym)RuCl$_2$]$_2$, dimethylimidazolium triflate, 2,2'-bipyridine-4,4'-dicarboxylic acid, 2,2'-bipyridine-4,4'-dicarboxylic acid, 2,2'-bipyridine-4,4'-dimethyl ester, and 4,4'-dihydroxy-2,2'-bipyridine were synthesized according to previously established methods. Additionally, complexes Cp*Ir(ppy)Cl, and [Cp*Ir(ppy)OH$_2$][OTf] (10), [(p-cym)Ru(bpy)Cl][Cl], and [(p-cym)Ru(bpy)OH$_2$][OTf]$_2$ (12) were synthesized by established procedures. All other reagents and solvents were commercially available and used without further purification unless specified. Deuterated solvents were purchased from Cambridge Isotope Laboratories. For analysis of hydrides, CD$_2$Cl$_2$ and CD$_3$CN were dried over calcium hydride prior to use. For all other samples deuterated solvents were used as received. $^1$H NMR spectra, $^{13}$C{$^1$H} NMR, $^{19}$F NMR spectra were recorded on 300 MHz or 500 MHz Bruker spectrometers (δ in ppm, J in Hz). $^1$H NMR spectra and $^{13}$C{$^1$H} NMR spectra were referenced to the residual solvent peak. $^{13}$C{$^1$H} NMR in D$_2$O were referenced to an external standard of 1,4-dioxane (67.19 ppm). $^{19}$F NMR spectra were referenced to an external trifluoroacetic acid standard (−78.55 ppm). Elemental analysis was performed by Atlantic Microlab, Inc. (Norcross, Ga.). HRMS analysis was performed by at the University of Washington.

General Procedure for Synthesis of [Cp*Ir(N—N)Cl]Cl and [Cp*Rh(N—N)Cl]Cl Complexes This is a modified procedure of the synthesis provided by Dadci et al. 0.25 mmol [Cp*IrCl$_2$]$_2$ or [Cp*RhCl$_2$]$_2$ and 0.50 mmol ligand (bpy, phen, bpy-OMe, bpy-COOMe, bpy-4-OH) were placed under nitrogen in a round-bottom flask fitted with a septum. 20 mL of degassed methanol was then added via syringe. The resultant mixture rapidly changed appearance from an orange suspension to a yellow-orange solution. The solution was stirred at room temperature for an additional 30 minutes. The solvent was then removed on a rotary evaporator under air. The resulting orange-yellow solid was dissolved in a minimal amount of dichloromethane, and layered with diethyl ether to recrystallize. The products [Cp*Ir(bpy)Cl][Cl] (3), [Cp*Ir(phen)Cl][Cl],

[Cp*Ir(bpy-OMe)Cl][Cl], [Cp*Ir(bpy-4-OH)Cl][Cl], [Cp*Rh(bpy)Cl][Cl], [Cp*Rh(bpy-COOMe)Cl][Cl], and [Cp*Rh(bpy-OMe)Cl][Cl] were verified by comparison with published literature spectra. Characterization data for previously unreported complexes is presented below:

[Cp*Ir(bpy-COOMe)Cl][Cl].$H_2O$ Yield: 76%. $^1$H NMR (500 MHz, $CD_2Cl_2$) δ 9.23 (d, J=5.8 Hz, 2H), 8.96 (s, 2H), 8.41 (d, J=6.1 Hz, 2H), 4.08 (s, 6H), 1.81 (s, 15H). $^{13}$C{$^1$H} NMR (126 MHz, $CD_2Cl_2$) δ 163.57, 156.00, 153.54, 141.16, 129.12, 123.88, 123.50 ($CF_3$), 120.61 ($CF_3$), 91.05, 54.09, 9.18. Elemental Analysis: Calculated for $C_{24}H_{29}Cl_2IrN_2O_5$: C, 41.86; H, 4.24; N, 4.07. Measured: C, 42.04; H, 4.51; N, 4.14.

General Procedure for Synthesis of [Cp*Ir(N—N)$OH_2$][OTf]$_2$ and [Cp*Rh(N—N)$OH_2$][OTf]$_2$ Complexes 0.2 mmol of [Cp*Ir(N—N)Cl]Cl or [Cp*Rh(N—N)Cl]Cl was weighed into a 20 mL vial in air and then pumped into a glovebox. The complex was then fully dissolved in approximately 10 mL of water. Separately, 0.4 mmol (2 eq.) silver trifluoromethanesulfonate was dissolved in a minimal amount of water (ca. 1 mL) and added to the metal complex solution. The resulting suspension was then stirred for 45 min at room temperature. After completion, the suspensions were removed from the glovebox and filtered through a syringe filter (0.2 μm, nylon) into a clean round-bottom flask. The solvent was removed under vacuum and the resulting solid was dried overnight in vacuo. [Cp*Ir(bpy)$OH_2$][OTf]$_2$ (1), [Cp*Ir(bpy-OMe)$OH_2$][OTf]$_2$ (5), [Cp*Ir(bpy-4-OH)$OH_2$][OTf]$_2$ (6), [Cp*Ir(phen)$OH_2$][OTf]$_2$ (7), and [Cp*Rh(bpy)$OH_2$][OTf]$_2$ (13) were verified by comparison with known literature spectra. Characterization data for previously unreported complexes is presented below:

[Cp*Ir(bpy-COOMe)$OH_2$][OTf]$_2$.$2H_2O$ (8) Yield: 52%. $^1$H NMR (500 MHz, $D_2O$) δ 9.15 (m, 2H), 9.03 (m, 2H), 8.23 (m, 2H), 3.96 (s, 6H), 1.58 (s, 15H). $^{13}$C{$^1$H} NMR (126 MHz, $D_2O$) δ 164.81, 156.49, 152.42, 141.42, 128.46, 123.97, 89.48, 53.82, 7.59. $CF_3$ not observed above noise. $^{19}$F NMR (470 MHz, $D_2O$) δ −76.83. Elemental Analysis: Calculated for $C_{26}H_{33}F_6IrN_2O_{13}S_2$: C, 32.81; H, 3.49; N, 2.94. Measured: C, 32.96; H, 3.29; N, 3.20.

[Cp*Rh(bpy-OMe)$OH_2$][OTf]$_2$ (14) Yield: 65%. $^1$H NMR (300 MHz, $D_2O$) δ 8.93 (d, J=6.8 Hz, 2H), 7.89 (s, 2H), 7.42 (d, J=6.0 Hz, 2H), 4.07 (s, 6H), 1.68 (s, 15H). $^{13}$C{$^1$H} NMR (126 MHz, $D_2O$) δ 169.31, 156.62, 152.56, 121.12 ($CF_3$) 118.59 ($CF_3$), 114.56, 110.80, 97.40, 56.95, 8.13. $^{19}$F NMR (470 MHz, $D_2O$) δ −76.79. Elemental Analysis: Calculated for $C_{24}H_{31}F_6N_2O_{10}RhS_2$: C, 37.41; H, 3.79; N, 3.64. Measured: C, 37.27; H, 3.96; N, 3.71.

[Cp*Rh(bpy-COOMe)$OH_2$][OTf]$_2$.$H_2O$ (15) Yield: 63%. $^1$H NMR (500 MHz, $D_2O$) δ 9.33 (d, J=5.6 Hz, 2H), 9.08 (s, 2H), 8.43 (d, J=5.9 Hz, 2H), 4.08 (s, 6H), 1.73 (s, 15H). $^{13}$C{$^1$H} NMR (126 MHz, $D_2O$) δ 164.94, 155.49, 152.66, 141.86, 128.14, 123.78, 122.85-115.69 (m, $CF_3$), 98.57, 98.51, 53.85, 7.96. $^{19}$F NMR (470 MHz, $D_2O$) δ −78.02. Elemental Analysis: Calculated for $C_{26}H_{31}F_6N_2O_{12}RhS_2$: C, 36.98; H, 3.70; N, 3.32. Measured: C, 36.64; H, 3.42; N, 3.29.

[Cp*Ir(bpy)H][$PF_6$] (2): This is a modification of a known procedure. A 50 mL 3M solution of formic acid was prepared by diluting 5.8 mL of 98% formic acid to 50 mL with water. The solution was then pH adjusted to ~3 using potassium hydroxide, degassed, and brought in to a glovebox. 39 mg of [Cp*Ir(bpy)Cl][Cl] (0.070 mmol) was dissolved in 10 mL of formic acid solution and stirred for 45 min, during which time the solution changed from a pale yellow color to a deeper yellow-orange color. Then 37 mg (0.23 mmol) of ammonium hexafluorophosphate were added. The ensuing air-sensitive yellow precipitate was collected on a fine frit and dried overnight in vacuo, giving 29 mg (66% yield) of 2. The product was then confirmed by comparison with known literature spectra.

[CpIr(bpy)Cl][Cl].$3H_2O$: 164 mg (0.5 mmol) [$CpIrCl_2$], and 78 mg (0.5 mmol) 2,2'-bipyridine were weighed into a 50 mL Schlenk flask and put under nitrogen atmosphere. 20 mL of dry acetonitrile was added and the reaction mixture was refluxed for 2 hours. The reaction was cooled to room temperature affording a yellow precipitate. The precipitate was collected and washed with hexanes. Yield: 50%. $^1$H NMR (500 MHz, MeOD) δ 9.47 (d, J=5.7 Hz, 2H), 8.65 (d, J=8.2 Hz, 2H), 8.29 (td, J=7.9, 1.5 Hz, 2H), 7.73 (ddd, J=7.4, 5.7, 1.4 Hz, 2H), 6.16 (s, 5H). $^{13}$C{$^1$H} NMR (126 MHz, MeOD) δ 157.55, 156.63, 142.17, 129.97, 126.06, 80.51. Elemental Analysis: Calculated for $C_{15}H_{19}Cl_2IrN_2O_3$: C, 33.46; H, 3.56; N, 5.20. Measured: C, 33.25; H, 3.34; N, 5.06.

[CpIr(bpy)$OH_2$][OTf]$_2$ (9): This complex was synthesized from [CpIr(bpy)Cl][Cl] as described above for the analogous Cp* complexes. Yield: 74%. $^1$H NMR (500 MHz, $D_2O$) δ 9.48 (d, J=5.6 Hz, 2H), 8.55 (d, J=8.8 Hz, 2H), 8.35 (t, J=7.7 Hz, 2H), 7.78 (t, J=6.3 Hz, 2H), 6.30 (s, 5H). $^{13}$C{$^1$H} NMR (126 MHz, $D_2O$) δ 156.27, 155.48, 141.94, 128.99, 124.72, 123.73-115.07 (m, $CF_3$).77.52. $^{19}$F NMR (471 MHz, $D_2O$) δ −76.78. ESI-HRMS calculated for [CpIr(bpy)]$^{2+}$, $C_{15}H_{13}IrN_2$: 207.0354. Measured: 207.0354.

Figure 6:
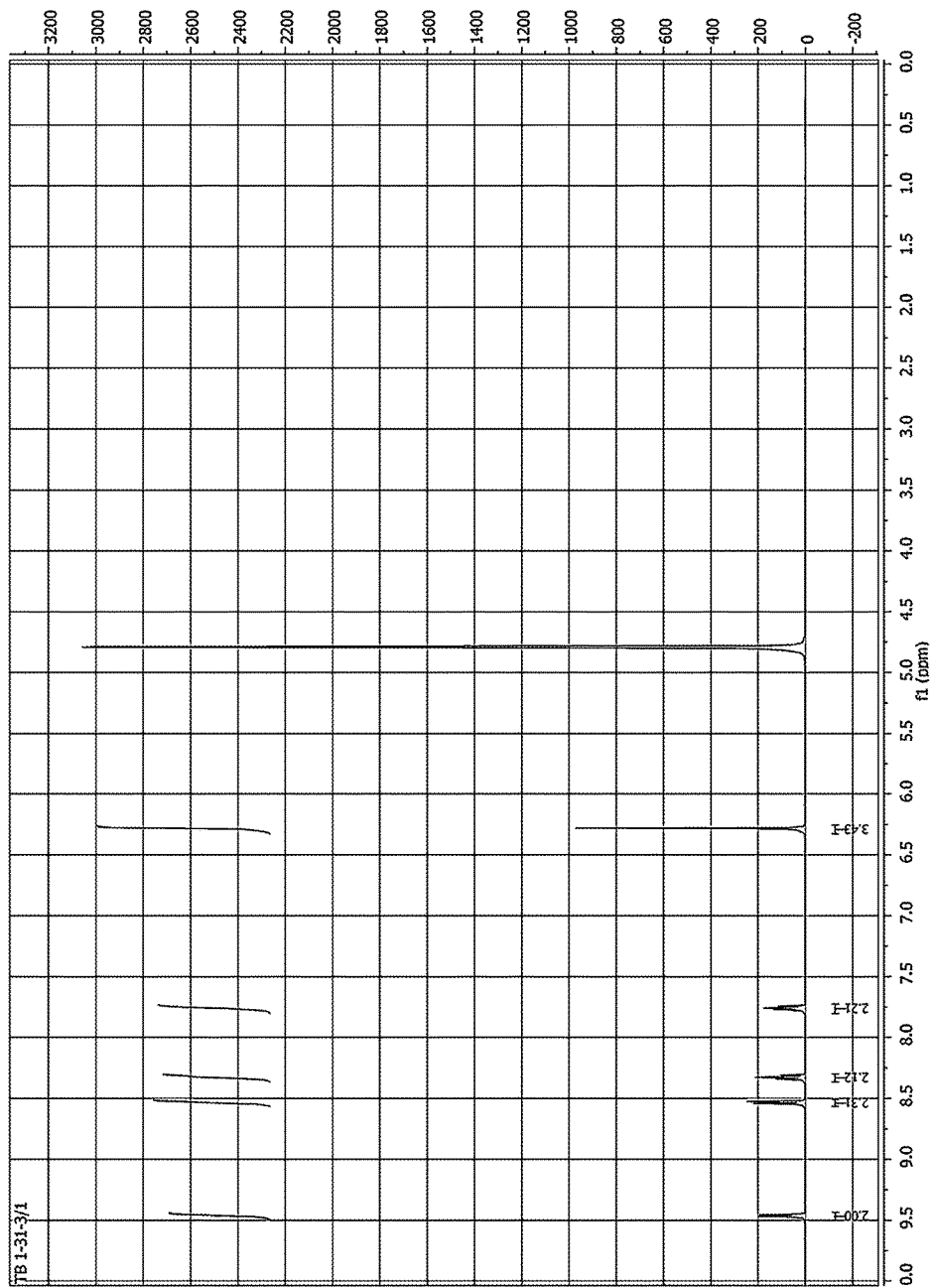
FIG. 6. $^1$H NMR Spectrum of [CpIr(bpy)OH$_2$][OTf]$_2$.

FIG. 6 is the $^1$H NMR Spectrum of [CpIr(bpy)$OH_2$][OTf]$_2$.

Figure 7:
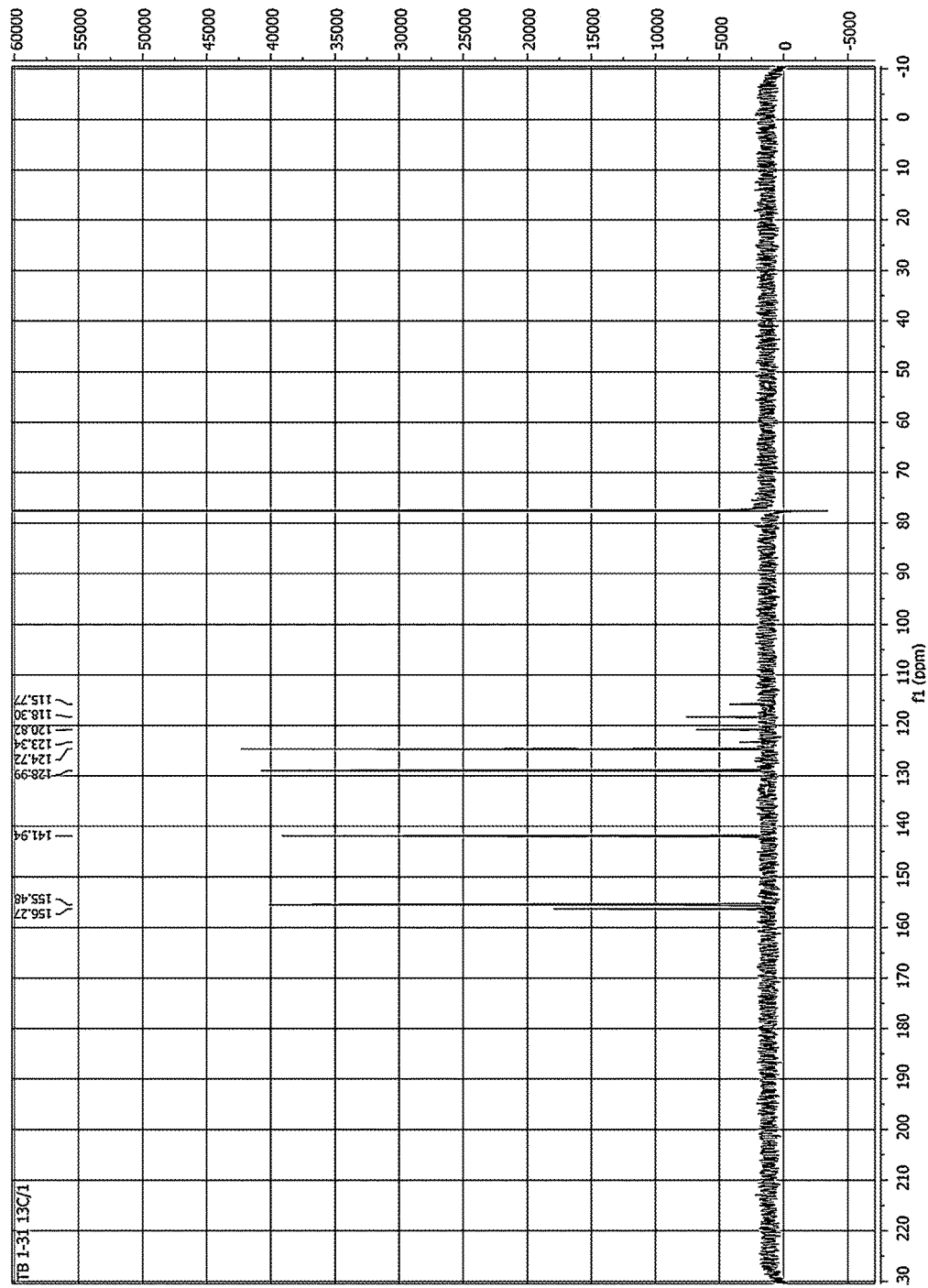
FIG. 7. $^{13}$C NMR Spectrum of [CpIr(bpy)OH$_2$][OTf]$_2$.

FIG. 7 is the $^{13}$C NMR Spectrum of [CpIr(bpy)$OH_2$][OTf]$_2$.

Figure 8:
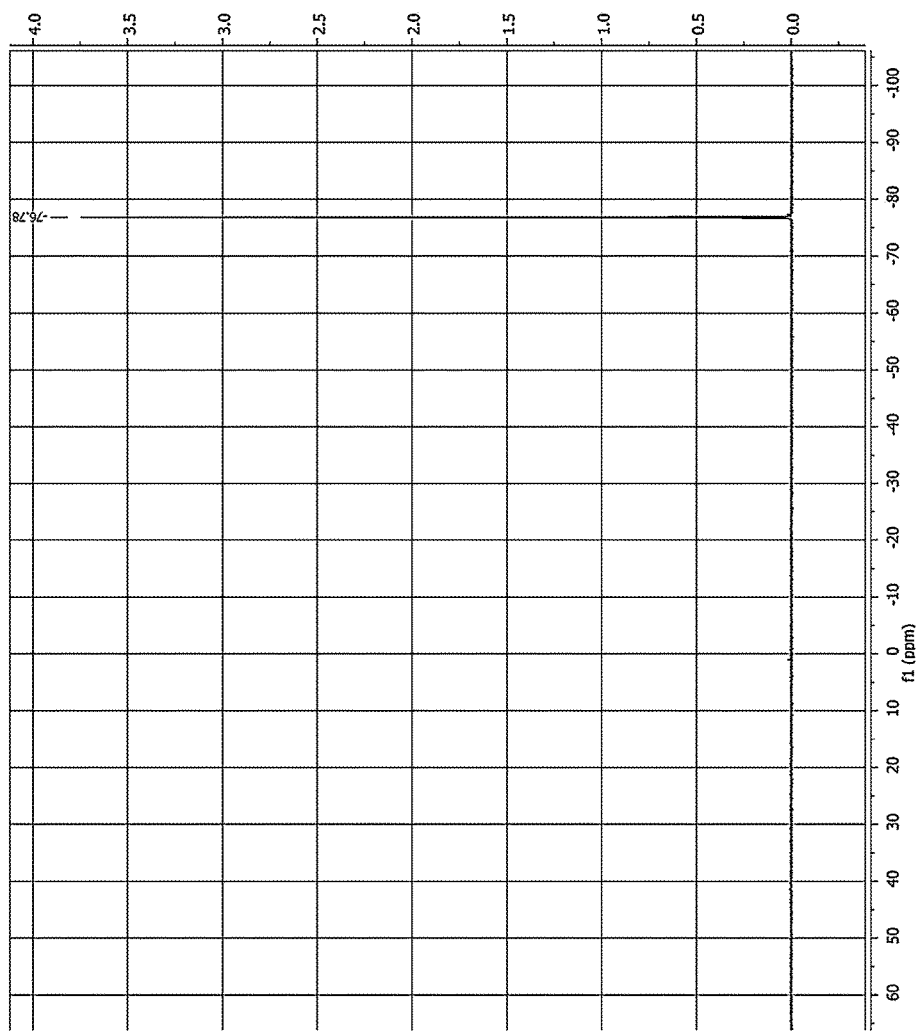
FIG. 8. $^{19}$F NMR Spectrum of [CpIr(bpy)OH$_2$][OTf]$_2$

FIG. 8 is the $^{19}$F NMR Spectrum of [CpIr(bpy)$OH_2$][OTf]$_2$

Figure 9:
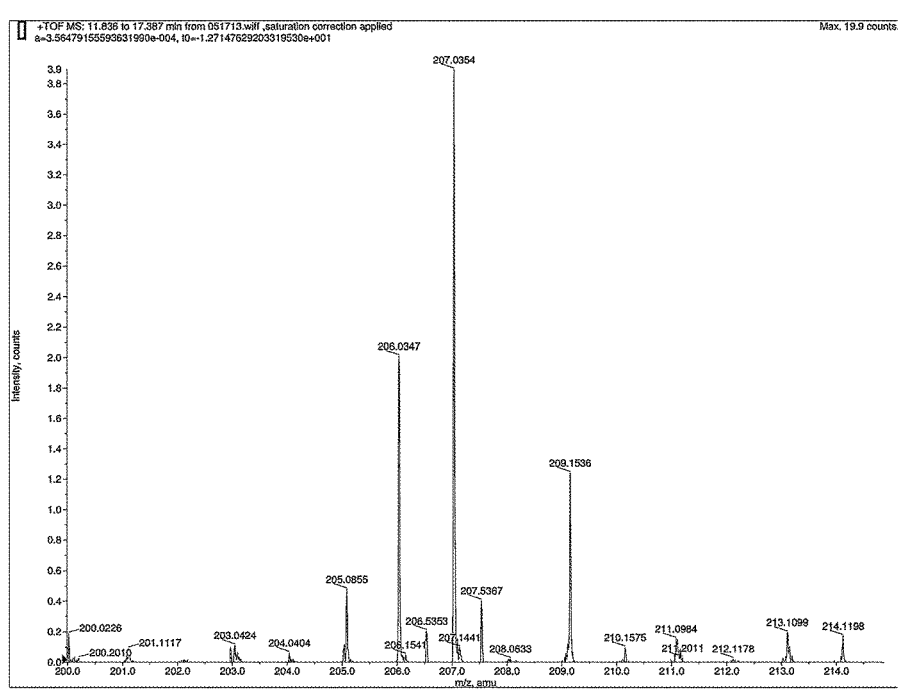
FIG. 9. ESI-HRMS results for [CpIr(bpy)OH$_2$][OTf]$_2$. Shown is the parent ion [CpIr(bpy)]$^{2+}$.

FIG. 9 is the ESI-HRMS results for [CpIr(bpy)$OH_2$][OTf]$_2$. Shown is the parent ion [CpIr(bpy)]$^{2+}$.

Synthesis of [Cp*Ir(NHC)$_2$Cl][OTf]

Figure 10:
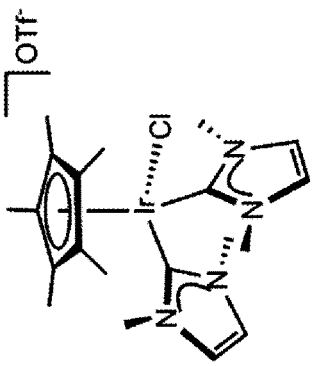
FIG. 10. Exemplary synthetic scheme for Synthesis of [Cp*Ir(NHC)$_2$Cl][OTf].
Figure 10:
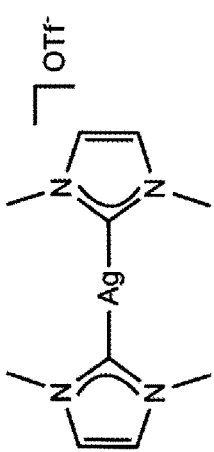
Figure 10:
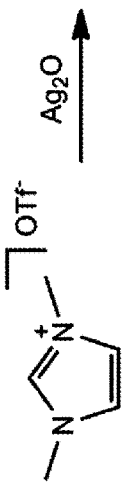

FIG. 10 illustrates an exemplary synthetic scheme for Synthesis of [Cp*Ir(NHC)$_2$Cl][OTf].

A) Preparation of Silver Bis-Carbene Transfer Reagent:

The following preparation is an adaptation of Hintermair, Englert, and Leitner.

984 mg (4 mmol) dimethylimidazolium triflate was weighed into a 250 mL round-bottom flask. 40 mL of dichloromethane was added under air. 580 mg $Ag_2O$ (2.5 mmol) and 560 mg (10 mmol) potassium hydroxide in 20 mL of water was then added. The biphasic mixture was stirred in the absence of light at room temperature overnight. The layers were then separated and the aqueous layer washed once with dichloromethane (30 mL). The washing was combined with the initial organic product and the combined organics were then filtered through a hydrophobic (PTFE, 0.2 micrometer) syringe filter into a separatory funnel. The solution was extracted 3 times with water (3×15 mL). The organic phase was then dried with sodium sulfate and the volatiles removed under vacuum. A white powder was obtained and dried overnight under vacuum in the dark. This compound was not fully characterized due to similarity with known complexes and was used in part b without further purification. $^1$H NMR (500 MHz, $CDCl_3$) δ 7.08 (s, 1H), 3.93 (s, 3H).

B) Transmetallation to Iridium:

340 mg (0.81 mmol) of the generated silver salt was weighed into a Schlenk flask under air and then transferred to a glovebox. To the flask was then added 302 mg [Cp*IrCl$_2$]$_2$ (0.379 mmol). 15 mL of dichloromethane was then added. The flask was capped and removed from the box. The solution was then stirred in the dark for 2 hours at room temperature. The solution was then filtered through a pad of celite in air and reduced under vacuum to approximately 1 mL. The solution was then layered with diethyl ether, and left overnight in a freezer (−35° C.) to precipitate. The air stable product was collected by filtration and washed with diethyl ether (30 mL). Yield: 440 mg (86%). $^1$H NMR (300 MHz, CD$_2$Cl$_2$) δ 7.08 (s, 4H), 3.45 (s, 12H), 1.64 (s, 15H). $^{13}$C{$^1$H} NMR (126 MHz, CD$_2$Cl$_2$) δ 147.14, 125.46, 124.81, 124.03, 123.27, 122.25, 95.67, 37.63, 10.24. $^{19}$F NMR (282 MHz, CD$_2$Cl$_2$) δ −77.23. Elemental Analysis: Calculated for C$_{21}$H$_{31}$ClF$_3$IrN$_4$O$_3$S: C, 35.82; H, 4.44; N, 7.96. Measured: C, 35.57; H, 4.41; N, 7.80.

Synthesis of [Cp*Ir(NHC)$_2$(H)][OTf].H$_2$O 136 mg (0.2 mmol) [Cp*Ir(NHC)$_2$Cl][OTf] and 76 mg (2 mmol, 10 eq) NaBH$_4$ were weighed into a Schlenk flask under air. The flask was then quickly flame-dried under vacuum and placed under N$_2$ atmosphere. 10 mL dry isopropanol was added via syringe. The resulting dark brown-orange suspension was stirred at room temperature under a light flow of nitrogen and sonicated periodically. After 2 hours of stirring, the solvent was removed in vacuo. 6 mL of dry dichloromethane was then added via syringe to give a dark brown suspension. The suspension was transferred via syringe filtration to a second flame-dried Schlenk flask to give a very pale yellow solution. The residue in the first flask was washed with additional dichloromethane and the washing transferred over via syringe filter. The dichloromethane volume was then reduced to approximately 2 mL under vacuum and 10 mL of diethyl ether was then added via syringe to generate a white precipitate. The sealed flask was placed in a freezer overnight. The next day, solvent was removed from the solid by syringe, and the resulting white solid was washed twice with diethyl ether in the same manner. The solid was then placed under vacuum to dry and stored in a glovebox. Yield: 53% $^1$H NMR (500 MHz, CD$_2$Cl$_2$) δ 6.94 (s, 4H), 3.54 (s, 12H), 1.94 (s, 15H), −16.20 (s, 1H). $^{13}$C{$^1$H} NMR (126 MHz, CD$_2$Cl$_2$) δ 150.72, 122.41, 93.45, 39.77, 11.11. CF$_3$ carbon not observed above noise due to C—F coupling. $^{19}$F NMR (470 MHz, CD$_2$Cl$_2$) δ −78.16. Elemental Analysis: Calculated for C$_{21}$H$_{34}$F$_3$IrN$_4$O$_4$S: C, 36.67; H, 4.98; N, 8.15. Measured: C, 36.42; H, 4.49; N, 7.98.

Procedures for Hydrogenation of Carboxylic Acids:

GC-FID analysis was performed on an Agilent Technologies 7890A GC system using a ResTek RT-U-bond column (acetic acid), Agilent Technologies DB-FFAP column (substrate scope experiments). All analytes were calibrated with reference to an internal standard using pure materials obtained from commercial sources.

A) Sample Procedure for Reactions Run in Neat Carboxylic Acid or Aqueous Acid Solutions:

0.004 mmol of catalyst was weighed in air and transferred to a vial. The vial was then taken into a nitrogen glovebox where the catalyst was dissolved in 2 mL acetic acid or aqueous acetic acid solution. Appropriate amounts of any additives (Lewis acid or HOTf) were then added. The solution was then transferred to a 30 mL Parr Instruments 5000 Multiple Reactor system vessel fitted with a PTFE liner. The reactor was then sealed, removed from the glovebox, and purged with hydrogen gas for 5 minutes before being pressurized with hydrogen (27-30 bar unless noted). Reactions were run for 65 hours at 120° C. unless otherwise specified. After completion, reactors were cooled to room temperature. A 25 μL aliquot was then removed, added to 10 μL isopropanol (internal standard), and diluted volumetrically to 5 mL with acetone for GC-FID analysis.

B) Procedure for Reaction with Catalyst Decomposition Products:

A reactor liner from a previous experiment using catalyst 4 was rinsed thoroughly with water and acetone, leaving behind the black solid decomposition product. The liner was then dried and taken into a nitrogen glovebox. 2 mL of acetic acid was added via syringe to the liner, which had been fitted into a 30 mL Parr Instruments 5000 Multiple Reactor system vessel. The reactor was then sealed, removed from the glovebox, and purged with hydrogen gas for 5 minutes before being pressurized with hydrogen (27-30 bar unless noted). Reactions were run for 65 hours at 120° C. unless otherwise specified. After completion, reactors were cooled to room temperature. A 25 μL aliquot was then removed, added to 10 μL isopropanol (internal standard), and diluted volumetrically to 5 mL with acetone for GC-FID analysis.

C) Procedure for Determination of Order of Reaction in Acetic Acid:

0.020 mmol of [Cp*Ir(bpy)OH$_2$][OTf]$_2$ was weighed in air and transferred to a vial. The vial was then taken in to a nitrogen glovebox where the catalyst was fully dissolved in 250 μL acetic acid. 50 μL aliquots were removed and transferred to 4 separate 30 mL Parr Instruments 5000 Multiple Reactor system vessels fitted with PTFE liners. To each reactor, 2 mL 3:1 (v:v) H$_2$O:HBF$_4$ was then added. Finally, 150 μL, 100 μL, 50 μL, and 0 μL of additional acetic acid was added to each of the 4 reactors respectively. Reactions were then completed and analyzed as described in Part A.

D) Procedure for pH Dependence Experiment:

Stock 8.7 M solutions of acetic acid in water and acetic acid in 1:1 (v:v) H$_2$O:HBF$_4$ were first prepared. Acetic acid in H$_2$O:HBF$_4$ solution was then added to the 8.7 M aqueous acetic acid solution until the desired pH was achieved (IQ Scientific IQ170 pH meter). Solutions were then thoroughly degassed. Separately, 0.004 mmol [Cp*Ir(bpy)OH$_2$][OTf]$_2$ was weighed into 4 separate vials. The vials containing catalyst and the stock solutions were then taken in to a nitrogen glovebox. Catalyst was then dissolved in 2 mL of stock solution of known pH. Reactions were then completed as described in Parts A and B. GC-FID analysis was run using 1,4-dioxane as dilution solvent.

E) Procedures for Substrate Scope Experiments a) Aliphatic Acids in Aqueous HBF$_4$ Solvent:

In a nitrogen glovebox, 10.2 mg (12 mmol) [Cp*Ir(bpy-OMe)OH$_2$][OTf]$_2$ was dissolved in 6 mL 3:1 (v:v) H$_2$O:HBF$_4$. 2 mL aliquots were then transferred to individual 30 mL Parr Instruments 5000 Multiple Reactor system vessels fitted with PTFE liners. 3.48 mmol of substrate was then added to the reactor. Vessels were then sealed and removed from the glovebox. Without exposure to air, reactors were then purged with H$_2$ and pressurized to 30 bar. Reactions were run for 18 h at 120° C. Upon completion, analysis was done by GC-FID using acetone as dilution solvent and 1,4-dioxane as internal standard.

b) Aliphatic Acids in Acetic Acid:

In a nitrogen glovebox, 10.2 mg (12 mmol) [Cp*Ir(bpy-OMe)OH$_2$][OTf]$_2$ and 20.5 mg (xx mmol) sodium trifluoromethanesulfonate (Lewis acid promoter) were dissolved in 6 mL 1:1 (mol:mol) substrate:acetic acid. 2 mL aliquots were then transferred to individual 30 mL Parr Instruments 5000 Multiple Reactor system vessels fitted with PTFE liners. Vessels were then sealed and removed from the glovebox. Without exposure to air, reactors were then purged with H$_2$ and pressurized to 30 bar. Reactions were run for 18 h at 120° C. Upon completion, analysis was done by GC-FID using acetone as dilution solvent and 1,4-dioxane as internal standard.

c) Levulinic Acid:

In a nitrogen glovebox, 10.2 mg (12 mmol) [Cp*Ir(bpy-OMe)OH$_2$][OTf]$_2$ was dissolved in 6 mL 1,2-dimethoxyethane. 100 μL (xx mmol) trifluoromethanesulfonic acid was then added via syringe. 2 mL aliquots were then transferred to individual 30 mL Parr Instruments 5000 Multiple Reactor system vessels fitted with PTFE liners. Vessels were then sealed and removed from the glovebox. Without exposure to air, reactors were then purged with H$_2$ and pressurized to 30 bar. Reactions were run for 18 h at 120° C. Upon completion, analysis was done by GC-FID using acetone as dilution solvent and 1,4-dioxane as internal standard.

Figure 11:
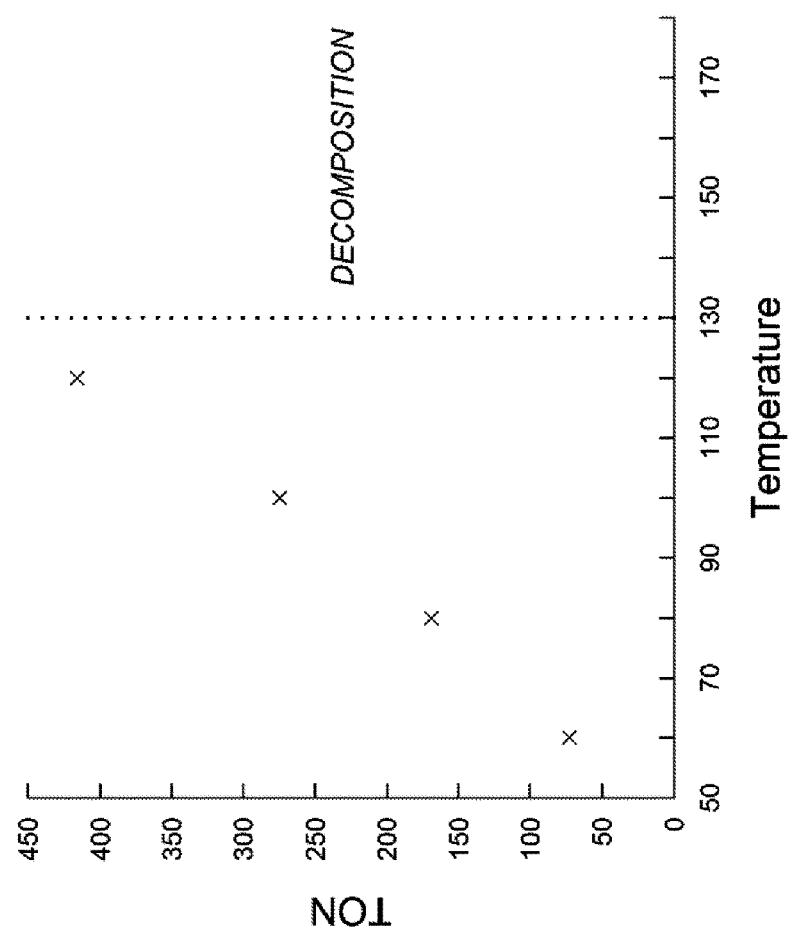
FIG. 11. Temperature dependence of acetic acid hydrogenation. 2 mM catalyst 1 in glacial acetic acid, 27 bar $H_2$, 65 h.

FIG. 11 illustrates the temperature dependence of acetic acid hydrogenation. 2 mM catalyst 1 in glacial acetic acid, 27 bar H$_2$, 65 h.

FIG. 12 illustrates hydrogen pressure dependence of acetic acid hydrogenation. 2 mM catalyst 13 in glacial acetic acid, 120° C., 18 h.

TABLE 3

Full Catalyst Screen for Acetic Acid Hydrogenation

| Catalyst | TON | StDev | Product Ratio[c] | Additive |
|---|---|---|---|---|
| 1[a] | 425 | 8 | 42:1 | |
| 2[a] | 41 | 12 | 1:1 | |
| 2[a] | 503 | 34 | 55:1 | 3 eq. HOTf |
| 3[b] | 11 | | 1:1 | |
| 4[b] | 19 | | 3:1 | |
| 5[a] | 777 | 15 | 21:1 | |
| 5[a] | 1637 | 25 | 59:1 | 8 eq. Sc(OTf)$_3$ |
| 6[a] | 615 | 50 | 31:1 | |
| 7[a] | 389 | 56 | 37:1 | |
| 8[b] | 9 | | 1:1 | |
| 9[b] | 40 | | 8:1 | |
| 10[b] | 8 | | 1:1 | |
| 11[b] | 8 | | 1:1 | |
| 12[b] | 21 | | 4:1 | |
| 13[a] | 96 | 5 | 94:1 | |
| 14[a] | 56 | 1 | 26:1 | |
| 15[a] | 125 | 23 | 12:1 | |
| No Catalyst | trace product | | | |

[a]Average of 3 trials with calculated standard deviation.
[b]Average of two trials. All run with 2 mM catalyst in glacial acetic acid, 27 bar H$_2$, 120° C., 65 h.
[c]Ethyl Acetate:Ethanol.

TABLE 4

Screen of Lewis acids.[a]

| Lewis Acid | TON | STDev |
|---|---|---|
| LiOTf | 488 | 118 |
| NaOTf | 456 | 23 |
| NaOTf[b] | 227 | 92 |
| KOTf | 412 | 113 |
| Ba(OTf)$_2$ | 473 | 27 |

TABLE 4-continued

Screen of Lewis acids.[a]

| Lewis Acid | TON | STDev |
|---|---|---|
| Zn(OTf)$_2$ | 465 | 51 |
| Sc(OTf)$_3$ | 525 | 70 |
| None | 290 | — |

[a]Average of 3 trials with calculated standard deviation. 2 mM catalyst 5 in glacial acetic acid, 20 mM Lewis acid, 27 bar H$_2$, 120° C., 18 h.
[b]With equimolar 15-crown-5.

Figure 13:
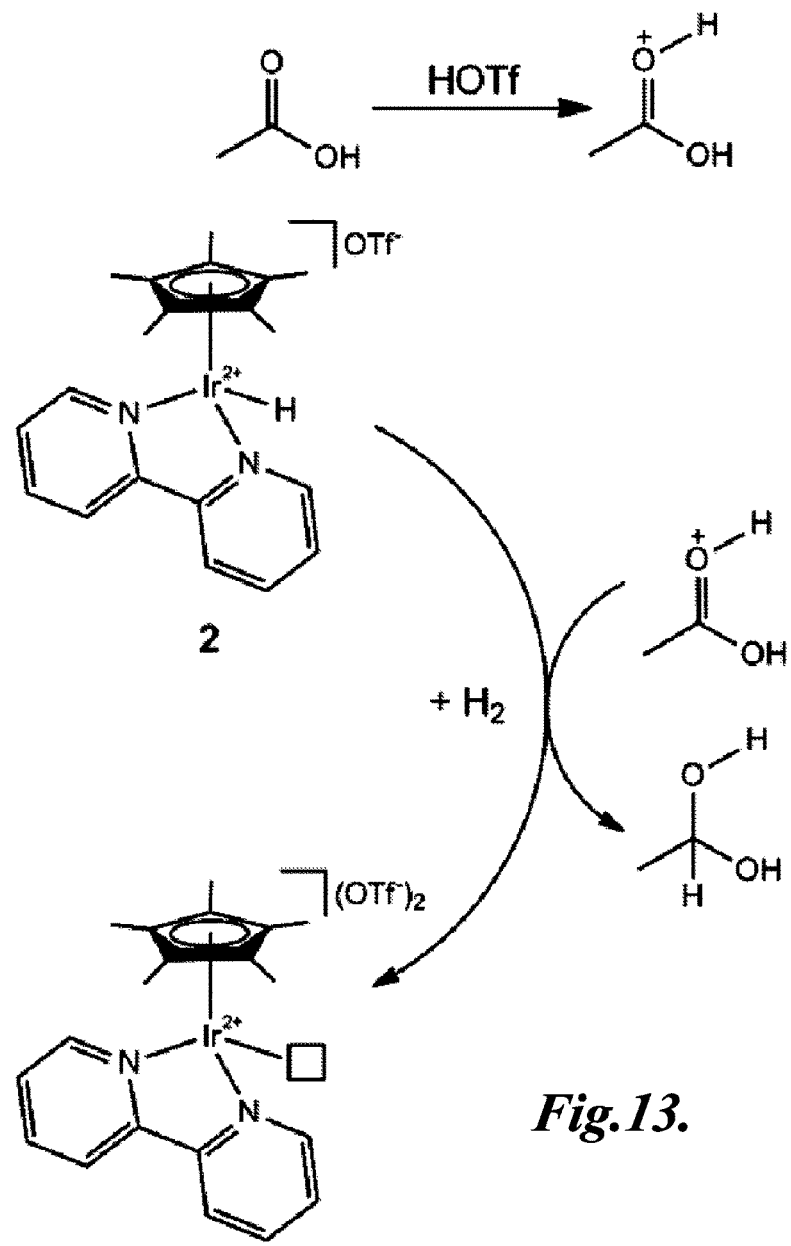
FIG. 13. Reaction of acetic acid with HOTf to initiate catalysis by 2.

FIG. 13 illustrates the reaction of acetic acid with HOTf to initiate catalysis by 2.

Example 2

Disproportionation Catalysis

Note: Equation and Compound Numbers Reset at 1 in Example 2.

The decomposition of formic acid almost always proceeds by dehydrogenation to produce H$_2$ and CO$_2$ (Eq. 1) or by dehydration to produce CO and H$_2$O (Eq. 2). In rare cases, disproportionation to produce formaldehyde (Eq. 3) has been observed—with low selectivity on metal oxides above 200° C.

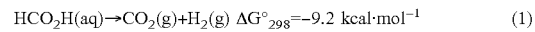

$$HCO_2H(aq) \rightarrow CO_2(g) + H_2(g) \quad \Delta G°_{298} = -9.2 \text{ kcal·mol}^{-1} \quad (1)$$

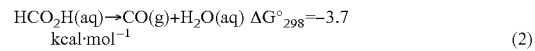

$$HCO_2H(aq) \rightarrow CO(g) + H_2O(aq) \quad \Delta G°_{298} = -3.7 \text{ kcal·mol}^{-1} \quad (2)$$

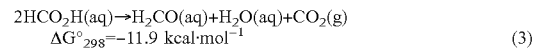

$$2HCO_2H(aq) \rightarrow H_2CO(aq) + H_2O(aq) + CO_2(g) \quad \Delta G°_{298} = -11.9 \text{ kcal·mol}^{-1} \quad (3)$$

In 1911, Sabatier reported that some dimethoxymethane was produced upon thermolysis of HCO$_2$H over ThO$_2$, providing indirect evidence for a methanol-producing pathway (Eq. 4). There is great interest in the facile interconversion of various C$_1$ chemicals, and so it is remarkable that reports of the decomposition mode shown in Eq. 4 have been absent in the literature since that now century old report. Catalytic transformations of C$_1$ feedstocks—natural gas (CH$_4$) and synthesis gas (CO/H$_2$) derived from various sources—are a key foundation of chemical industry. HCO$_2$H is produced on large scale (~700,000 tons/yr) via these traditional fossil fuel feedstocks. Alternative, renewable routes to HCO$_2$H are being developed, with CO$_2$ or biomass as starting points. New transformations of formic acid are needed to ignite and promote development of renewable C$_1$ chemistry; conversion to methanol represents a renewable route to a major commodity chemical and high energy density fuel.

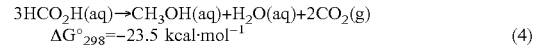

$$3HCO_2H(aq) \rightarrow CH_3OH(aq) + H_2O(aq) + 2CO_2(g) \quad \Delta G°_{298} = -23.5 \text{ kcal·mol}^{-1} \quad (4)$$

We report here that a molecular iridium species catalyzes the disproportionation of formic acid to methanol, water, and CO$_2$ (Eq. 4). The present study represents, to our knowledge, the first well-defined example of such a reaction mode of formic acid. The reaction occurs in acidic aqueous solution, without the need for any organic solvent or added hydrogen. The net reaction is formally a transfer hydrogenation, with HCO$_2$H acting as hydrogen source and substrate simultaneously. This fundamental C$_1$ reaction poses a number of interesting mechanistic questions and may have ramifications in the conversion of CO$_2$ to fuels and chemicals. Hydrogenation of formic acid to methanol directly is very unusual (generally an alkyl formate intermediate must be produced); disproportionation of formic acid raises the possibility of direct formation of methanol. We have started to map the scope and mechanism of this simple, yet essentially unrecognized reaction. While dehydrogenation of $HCO_2H$ occurs simultaneously, we have shown that the catalyst activity and the selectivity to methanol can be tuned by changing reaction conditions.

TABLE 5

Catalytic disproportionation of aqueous $HCO_2H$.[a]

| | Catalyst (conditions) | TON | TOF ($h^{-1}$) | Conversion | MeOH Selectivity |
|---|---|---|---|---|---|
| 1 | $[Cp*Ir(Cl)_2]_2$ | 0 | 0 | 16(3)% | 0% |
| 2 | $[Cp*Ir(Cl)_2]_2$ + 2 bpy | 33(1) | 1.4(1) | 20(3)% | 4(1)% |
| 3 | 1 | 34(1) | 1.4(1) | 23(3)% | 4(1)% |
| 4 | 1 (pH 0.5) | 70(2) | 2.9(1) | 48(3)% | 4(1)% |
| 5 | 1 (12M $HCO_2H$)[b] | 156(3) | 6.5(1) | 16(3)% | 7(1)% |
| 6 | 1 (12M $HCO_2H$, 60° C.)[b] | 70(2) | 2.9(1) | 3(3)% | 12(2)% |
| 7 | 1 (3M $HCO_2H$ in $D_2O$)[c] | 54(9) | 2.6(2) | 12(3)% | 11(2)% |

[a]Conditions (unless noted): 3M formic acid (pH 1.4), 0.25 mM [Ir] (0.0083 mol %, 83 ppm), 80° C., 24 h. Average of at least two runs, with estimated uncertainty in parentheses. Full details below.
[b]0.25 mM [Ir] (0.002 mol %, 2 ppm).
[c]Values from NMR data.

Aqueous $HCO_2H$ solutions containing $[Cp*Ir(bpy)(H_2O)][OTf]_2$ (1, Cp*=pentamethylcyclopentadienyl, bpy=2,2'-bipyridine) produced methanol upon heating. This result was surprising because $HCO_2H$ is commonly used as a source of $H_2$ in transfer hydrogenation reactions, and 1 is a well known transfer hydrogenation catalyst, with no prior reports of methanol-producing side reactions. When 3 M $HCO_2H$ (2 mL, pH 1.4) containing 1 (0.5 μmol, 0.25 mM, 0.008 mol %) was heated at 80° C. for 24 h in a sealed vessel, 17 μmol of methanol was produced (by $^1H$ NMR spectroscopy). This corresponds to 34 turnovers (TON) and a turnover frequency (TOF) of 1.4 $h^{-1}$ (Table 5, entry 3). Methanol and methyl formate (produced by $HCO_2H$ esterification) are the only products observed in solution, but roughly 23% of the $HCO_2H$ had been consumed at this time, indicating 4% selectivity for methanol. [Under conditions of excess formic acid, methanol is partially converted to methyl formate; at full conversion only methanol was observed. Methanol yields represent the sum of methanol and methyl formate products.] 1:2 mixtures of $[Cp*Ir(Cl)_2]_2$ and bpy gave similar results (Table 5, entry 2). The bipyridyl ligand is important, as neither $[Cp*Ir(Cl)_2]_2$ (Table 5, entry 1) nor $[Cp*Ir(H_2O)_3][SO_4]$ without bpy produced any detectable methanol. Formic acid was consumed with these Ir species, however, and the pressure in sealed reaction vessels rose, implying that Eqs. 1 and/or 2 are catalyzed in lieu of Eq. 4.

That the methanol originates from $HCO_2H$ was confirmed by the production of methanol-$^{13}C$ upon heating a solution of $H^{13}CO_2H$ in $D_2O$ at 80° C. in the presence of 1 in a sealed NMR tube. In addition to the signal for methanol-$^{13}C$, a prominent resonance for $^{13}CO_2$— but not $^{13}CO$— was observed in the $^{13}C$ NMR spectrum, consistent with a competition between Eq. 1 and Eq. 4.

Figure 25:
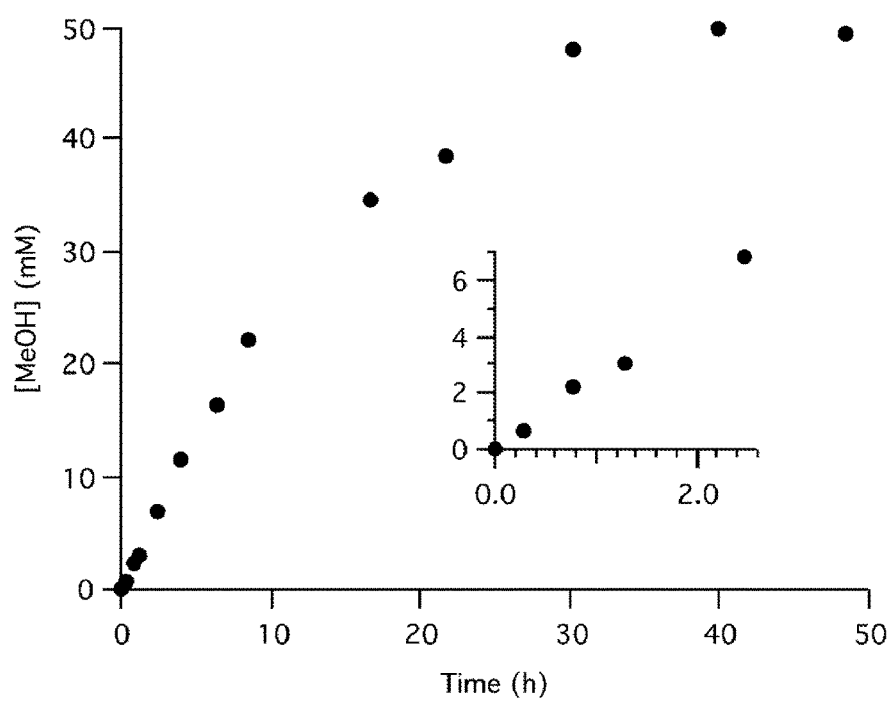
FIG. 25. Time course of methanol formation when 1 mM 1 was used as catalyst. Inset shows early reaction times. Reaction conditions: 1 mM 1, 3 M formic acid in $D_2O$, 80° C.

Initial observations indicate that the formic acid disproportionation is homogeneously catalyzed. Under the reaction conditions described here, no films or particles were deposited from the clear, yellow solutions. Addition of a mercury drop to a vigorously stirred reaction had no impact on the amount of MeOH produced. There was no induction period, with methanol forming steadily once the reaction temperature was reached (FIG. 25). Under other conditions, such as high [Ir] (>10 mM) or prolonged heating at 100° C., reaction mixtures turned dark blue-purple ($\lambda_{max}$=730 nm, FIG. 29)—a color characteristic of $IrO_2$ nanoparticles. Notably, the blue solids that remained after removal of volatiles were essentially inactive towards methanol production, instead acting as highly active catalysts for the dehydrogenation of $HCO_2H$ to $H_2$ and $CO_2$.

Figure 30:
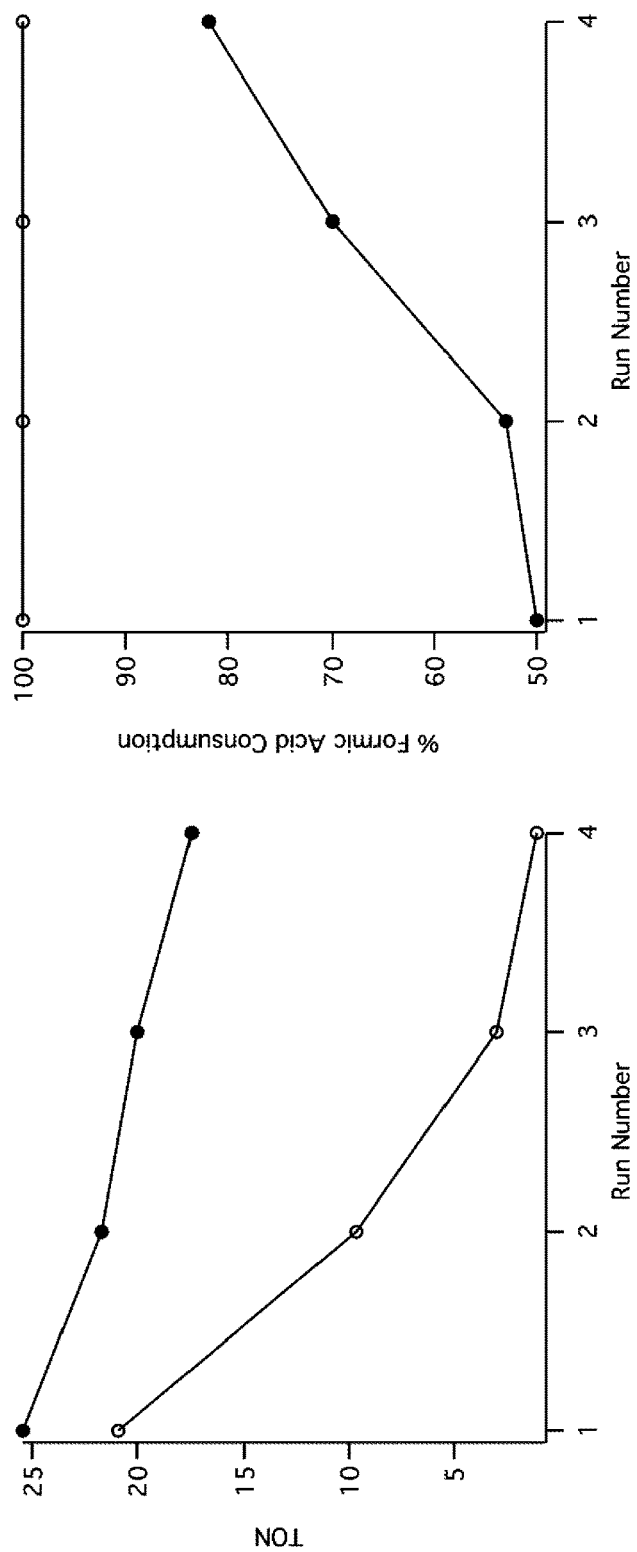
FIG. 30. Plots of recycle experiments at 80° C. (filled circles) and 100° C. (empty circles). The fourth run of the 100° C. recycle experiment was run at 80° C. Left plot shows changes in turnover number when volatiles were removed at the end of the reaction and replaced with fresh 3 M formic acid, while right plot shows changes in % consumption of formic acid. Conditions: 1 mM catalyst 1, 3 M formic acid, 24 hours.

Catalyst decomposition is further indicated by recycle experiments at 80 and 100° C. At 80° C., the catalyst was fairly robust, and could be recycled four times with only ~30% loss of activity for methanol production (FIG. 30). In contrast, at 100° C., 95% loss of methanol activity was observed over four cycles (and the reaction mixture became turbid purple-blue). Together, these observations are consistent with homogeneous catalyst 1 acting as the only catalyst for methanol production, whereas both 1 and its decomposition products catalyze the transformation to $H_2$ and $CO_2$.

Figure 14:
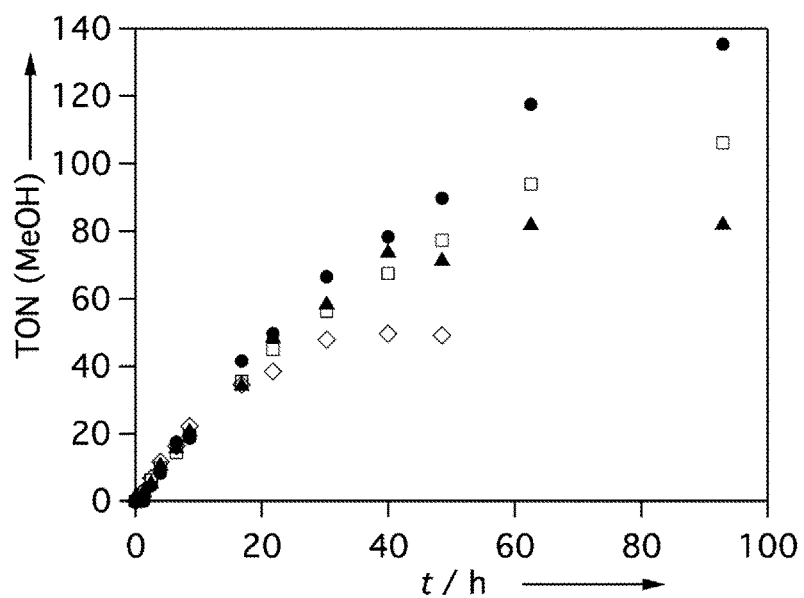
FIG. 14. TON for methanol production over time at various: 1 mM (empty diamonds), 0.5 mM (filled triangles), 0.25 mM (empty squares), and 0.125 mM (filled circles). Conditions: 3 M HCO$_2$H/D$_2$O, 80° C.

FIG. 14 illustrates TON for methanol production over time at various [1]: 1 mM (empty diamonds), 0.5 mM (filled triangles), 0.25 mM (empty squares), and 0.125 mM (filled circles). Conditions: 3 M $HCO_2H/D_2O$, 80° C.

Figure 21:
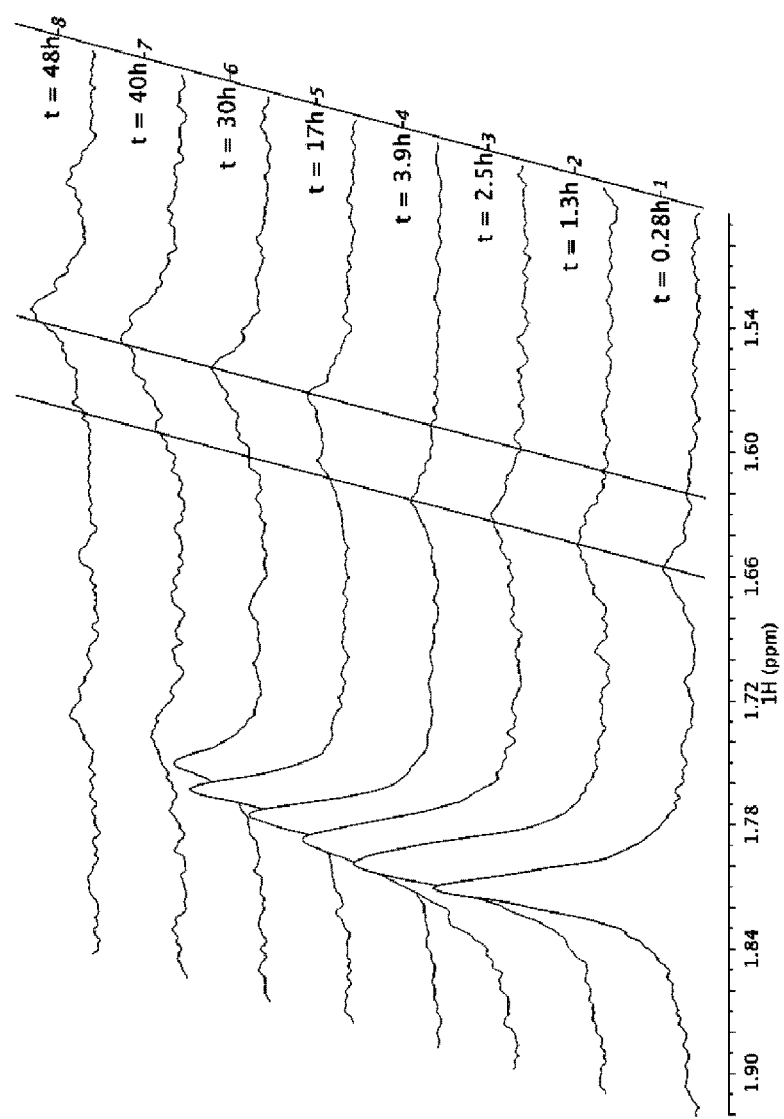
FIG. 21. $^1$H NMR spectra following a catalytic reaction (Cp* region). Early spectra show hydride 2 (δ 1.81) as the major species in solution, along with formate 3 (δ1.66). As the reaction proceeds, 2 and 3 are consumed and new, unidentified resonances appear. Reaction conditions: 1 mM 1, 3 M formic acid in D$_2$O, 80° C.

Intrigued by the unprecedented homogeneous formic acid disproportionation reaction, we set out to understand catalyst specification and other salient features of the mechanism in order to improve the selectivity to methanol. $^1H$ NMR spectroscopy studies revealed that dissolving pre-catalyst 1 in 3 M $HCO_2H/D_2O$ causes rapid conversion at ambient temperature to a mixture of deuteride $[Cp*Ir(bpy)(D)][OTf]$ (2) and another species in a ~9:1 ratio. Electrospray ionization mass spectrometry under the same conditions featured ion peaks for deuteride 2 (m/z 486.2, FIG. 38) and identified the minor species as the formate complex $[Cp*Ir(bpy)(O_2CH)][OTf]$ (3, m/z 529.1). When catalytic reactions at 80° C. (1 mM [1]) were periodically cooled to room temperature and monitored by NMR spectroscopy, 2 and 3 remained unchanged for over 8 h before being gradually replaced by new, unidentified species over 48 h (FIG. 21). Methanol was observed as soon as 15 min after initiating heating, and grew steadily for over 8 h before its production slowed until halting after 48 h, coincident with decomposition of the catalyst species 2 and 3 (FIG. 14).

Figure 23:
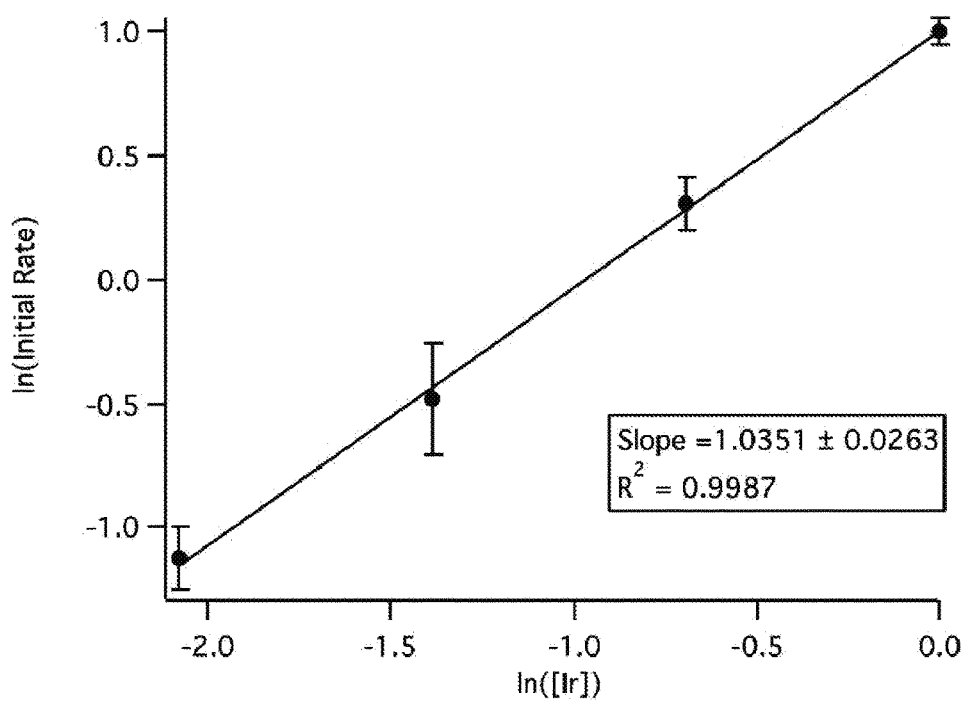
FIG. 23. Log-log plot of initial rate of methanol formation vs. [Ir], with linear fit (average of 2 runs). Slope of 1 indicates first-order dependence on catalyst. Reaction conditions: 0.125-1 mM 1, 3 M formic acid in $D_2O$, 80° C., initial rates from linear fits to first 10-20 hours of reaction.
Figure 24:
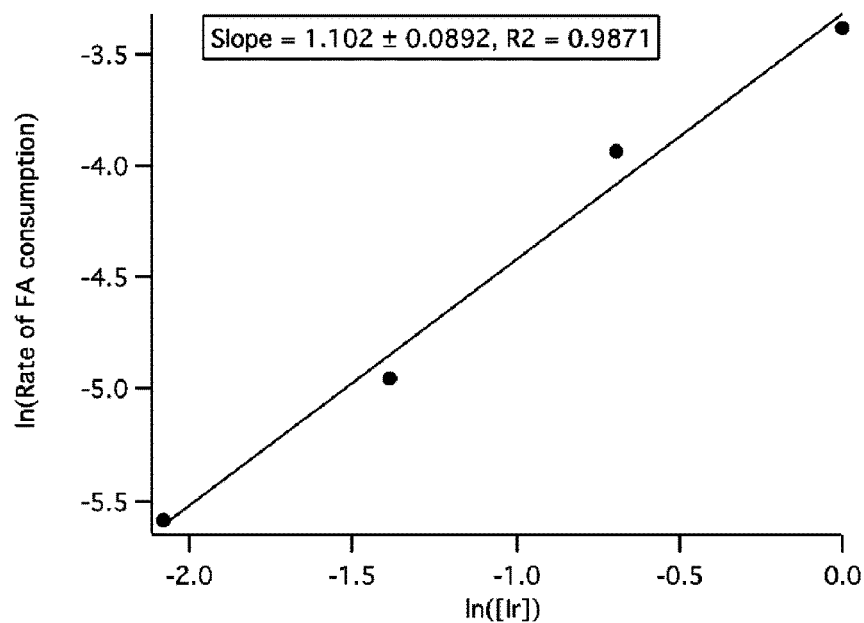
FIG. 24. Log-log plot of rate of consumption of formic acid vs. concentration of iridium. Slope of 1 indicates that overall formic acid decomposition (to $H_2/CO_2$ and to $CH_3OH$) is first order in catalyst. Reaction conditions: 0.125-1 mM 1, 3 M formic acid in $D_2O$, 80° C.

Methanol formation and formic acid consumption both exhibited a first-order dependence on [Ir] at early reaction times (FIGS. 23 and 24). Interestingly, catalyst deactivation was dependent on [Ir], with lower concentrations of 1 leading to longer catalyst lifetimes (FIG. 14). Higher TON values were therefore achieved at lower catalyst loadings. At 0.0313 mM 1 (~10 ppm), TON=200 after 120 h. The selectivity for methanol was significantly higher in $D_2O$ (Table 5, entry 7). Reaction 1 may be slowed relative to reaction 4 due to a large kinetic isotope effect of Ir—H protonolysis.

Figure 15A:
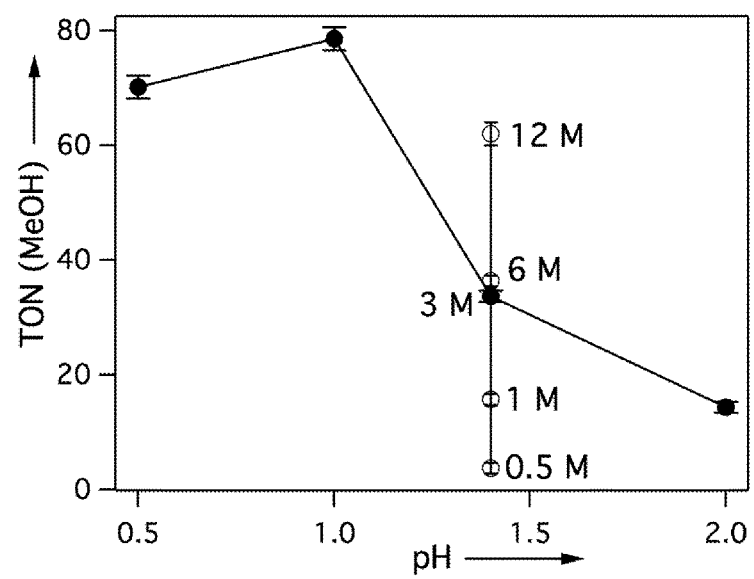
FIGS. 15A and 15B.

FIGS. 15A and B illustrate: (FIG. 15A) TON for methanol production as a function of pH (3 M $HCO_2H$, filled circles) and $[HCO_2H]$ (empty circles). (FIG. 15B) Methanol selectivity as a function of pH (3 M $HCO_2H$, filled circles) and $[HCO_2H]$ (empty circles). Conditions: 0.25 mM 1, 80° C., 24 h; solutions were adjusted to the appropriate pH using $HBF_4$ or NaOH.

Figure 15B:
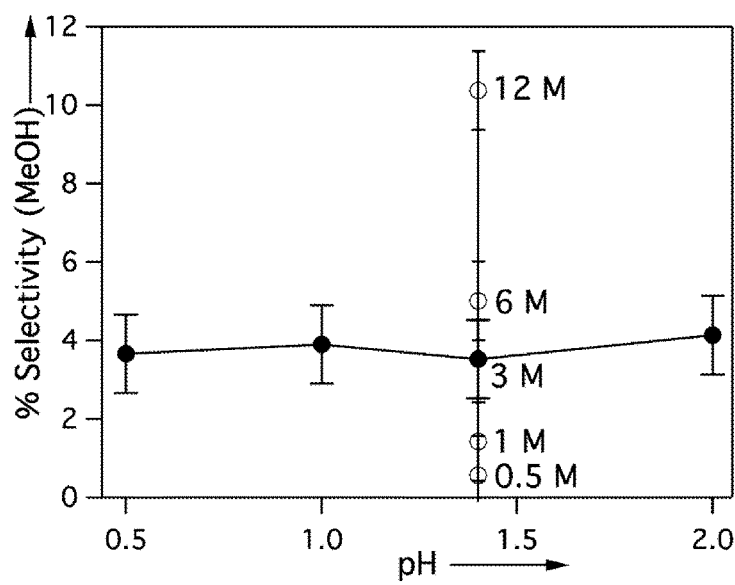

The reaction is strongly influenced by both pH and $[HCO_2H]$. When 3 M $HCO_2H$ solutions (0.25 mM in 1), with pH adjusted with $HBF_4$ or NaOH were heated to 80° C. for 24 h, the TON varied from only 14 turnovers at pH 2 to 70 or more below pH 1 (FIG. 15A). Changing the initial $[HCO_2H]$ from 0.5-12 M (maintaining pH 1.4) revealed a similar, roughly 15-fold increase in TON, from 4 (0.5 M $HCO_2H$) to 62 (12 M $HCO_2H$) (FIG. 15A). The selectivity for methanol was not significantly affected by pH (FIG. 15B), suggesting that reactions 1 and 4 respond similarly to pH changes. However, selectivity for methanol was markedly improved upon increasing the initial [$HCO_2H$] (adjusted to pH 1.4): 0.5 M $HCO_2H$ solutions showed very poor selectivity for methanol (~0.05%) with selectivity of 10% seen in 12 M $HCO_2H$ (FIG. 15B).

We considered three possible intermediates for the multi-step hydrogenation of $HCO_2H$: (1) CO, (2) $CO_2$, or (3) formaldehyde. The intermediacy of CO or $CO_2$ was ruled out by inspection of the isotopic composition of the methanol produced from different reaction mixtures. Conversion of $HCO_2H$ in $D_2O$ solvent formed $CH_3OD$, $CH_2DOD$, and $CHD_2OD$ but no $CD_3OD$ (by $^1H$ and $^2H$ NMR spectroscopy, see FIG. 22). Conversely, only $CDH_2OH$ (no $CH_3OH$) was observed when $DCO_2D$ was the substrate in $H_2O$. These experiments indicate that the existing C—H (or C-D) bond of formic acid is preserved through the reduction, consistent only with the formaldehyde path. The improved performance at low pH and high [$HCO_2H$] suggests that the species being hydrogenated may be protonated formic acid, $HC(OH)_2^+$. Similar acid-promoted pathways have been invoked for ketone reduction catalyzed by 1. The improved selectivity would also be consistent with the diminished water content in concentrated $HCO_2H$ solutions, as a higher ratio of $HC(OH)_2^+$ to $H_3O^+$ would disfavor reaction 1.

Figure 16:
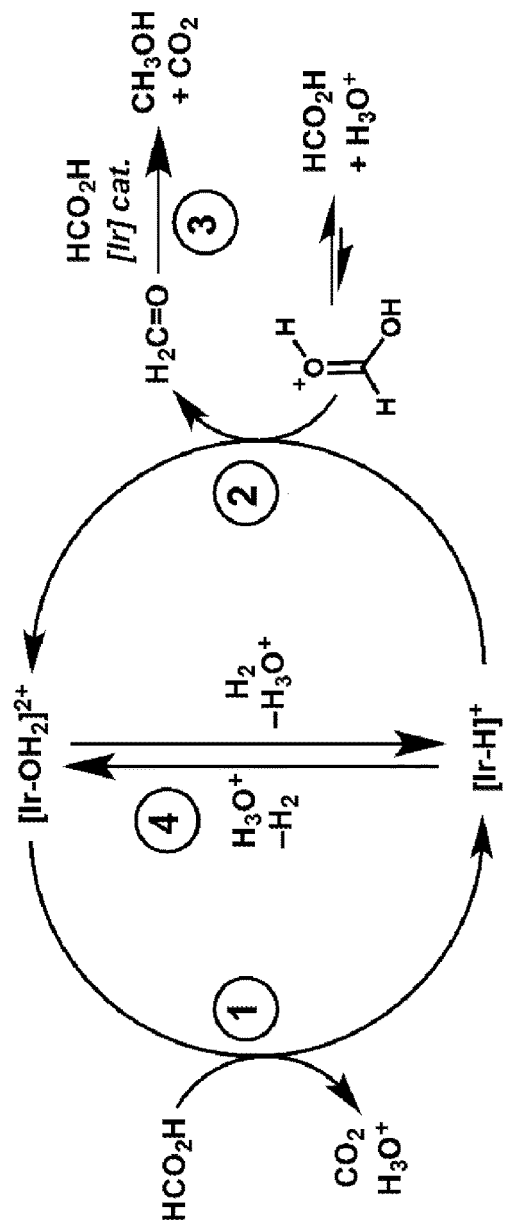
FIG. 16. A proposed pathway for methanol formation supported by the available data. The Ir—H complex is initially formed (step 1), followed either by protonation (step 4, dehydrogenation) or by reduction of protonated formic acid to generate formaldehyde (step 2) and ultimately methanol (step 3).

FIG. 16 lays out a plausible pathway for methanol formation supported by the available data. The Ir—H complex is initially formed (step 1), followed either by protonation (step 4, dehydrogenation) or by reduction of protonated formic acid to generate formaldehyde (step 2) and ultimately methanol (step 3).

Formaldehyde was shown to be a competent potential intermediate in the reaction. [Under the reaction conditions formaldehyde may be in equilibrium with its hydrate, methanediol.] Heating a 3 M $HCO_2H/D_2O$ solution containing paraformaldehyde-$^{13}C$ and 1 to 60° C. resulted in rapid formation of $^{13}CH_3OD$ and $^{13}CH_2DOD$. This transfer hydrogenation of formaldehyde catalyzed by 1 was found to be quite efficient, with TOF~240 $h^{-1}$ at 0.013 mol % catalyst loading, reaching completion at TON>7000. Thus, the reduction of $H_2CO$ is much faster than the observed catalytic rates (c.f. Table 5, entry 6 and Table 6, entry 1), consistent with turnover-limiting reduction of protonated $HCO_2H$.

Figure 20:
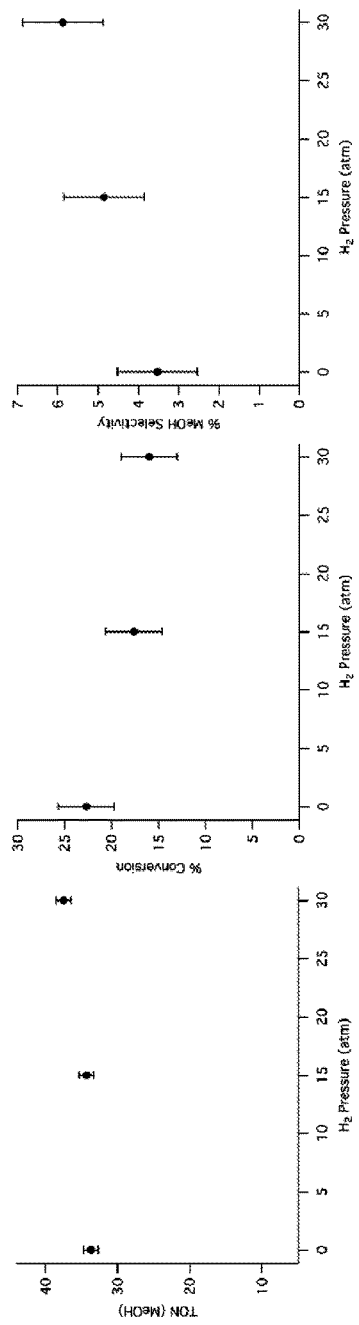
FIG. 20. Plots showing effect of $H_2$ pressure on TON (left), % conversion (middle) and % methanol selectivity (right). Conditions: 0.25 mM 1, 3 M formic acid, 80° C., 24 hours.

FIG. 16 implies that improved methanol selectivity should be accessible either by moving to more acidic formic acid solutions, or by suppressing the competing formate decomposition to $CO_2$ by addition of $H_2$ (FIG. 16, step 4). Under the standard 3 M $HCO_2H$ conditions, addition of 30 atm $H_2$ significantly improved methanol selectivity from 3.5 to 5.9% (FIG. 20). The combination of low pH, lower temperature, and high [$HCO_2H$] gave the best selectivity for methanol. Heating concentrated $HCO_2H$ (12 M; unadjusted pH 0.4) containing 0.25 mM 1 at 80° C. for 24 h gave 156 turnovers of methanol at 7% selectivity (Table 5, entry 5). When carried out at 60° C., methanol selectivity improved to 12% (Table 5, entry 6). The latter conditions represent, to our knowledge, the highest reported selectivity for $HCO_2H$ disproportionation.

In summary, we report the first molecular catalyst for the disproportionation of formic acid to methanol, water, and carbon dioxide. The reaction is a novel transformation of formic acid, a difficult substrate for homogeneously catalyzed reduction. Formic acid joins other challenging substrates whose homogeneous hydrogenation has been recently reported, including carboxylic acids, esters and amides. The formic acid reaction employs a catalyst bearing simple ligands, avoids the use of organic solvents and $H_2$ gas, and features very low catalyst loadings. Future efforts will focus on improving the overall methanol yield by increasing catalyst selectivity and/or recycling the $H_2$ and $CO_2$ byproducts. Thus, one hundred years after Sabatier's initial findings, the presently described reaction (Eq. 4) represents a new addition to the mature field of $C_1$ chemistry, one that may eventually play a role in the renewable production of methanol.

I. General Considerations

Reagents were manipulated under the inert atmosphere of a vacuum line or a nitrogen filled glovebox, except as noted. Water was degassed by thorough sparging with nitrogen before use. $D_2O$, formic acid-$d_2$, and formic acid-$^{13}C$ were purchased from Cambridge Isotopes Laboratories, Inc. and sparged with nitrogen before being stored in a glovebox. [Cp*Ir(Cl)$_2$]$_2$, [Cp*Ir(bpy)(Cl)][Cl], [Cp*Ir(bpy)($H_2O$)][OTf]$_2$ (1), and [Cp*Ir(bpy)($H_2O$)][SO$_4$] were synthesized by literature methods. Complex 1 was also synthesized by an alternative method, as detailed below. All other materials were readily commercially available, and used as received. $^1H$ and $^{13}C$ NMR spectra were recorded on Bruker AVANCE 300 or 500 MHz spectrometers at 25° C. Chemical shifts are reported with respect to NaTSP (3-(trimethylsilyl)propionic-2,2,3,3-$d_4$ acid sodium salt, δ 0.0) for $^1H$ NMR spectra and with respect to methanol (δ 49.50) for $^{13}C\{^1H\}$ NMR spectra. Solution pH was measured with either a Hach IQ170 meter equipped with a PHW77-SS ISFET electrode or a Thermo Orion 4-Star meter equipped with a Mettler-Toledo InLab Semi-Micro electrode. Note: the theoretical basis of pH measurements becomes less rigorous at the high concentrations of formic acid required for the chemistry described below. The measurements are taken as a guide, and are not quantitatively accurate. GC-MS data was acquired with an Agilent 7890A GC and 5975C mass spectrometer, using a 30 m Restek RT-U-Bond fused silica PLOT column. ESI-MS data was acquired on a Bruker Esquire ion trap mass spectrometer. UV-vis spectra were obtained on a HP 8453 diode array spectrophotometer.

II. Synthetic Procedures

Alternative Synthesis of [Cp*Ir(bpy) ($H_2O$)][OTf]$_2$ (1)

Figure 17:
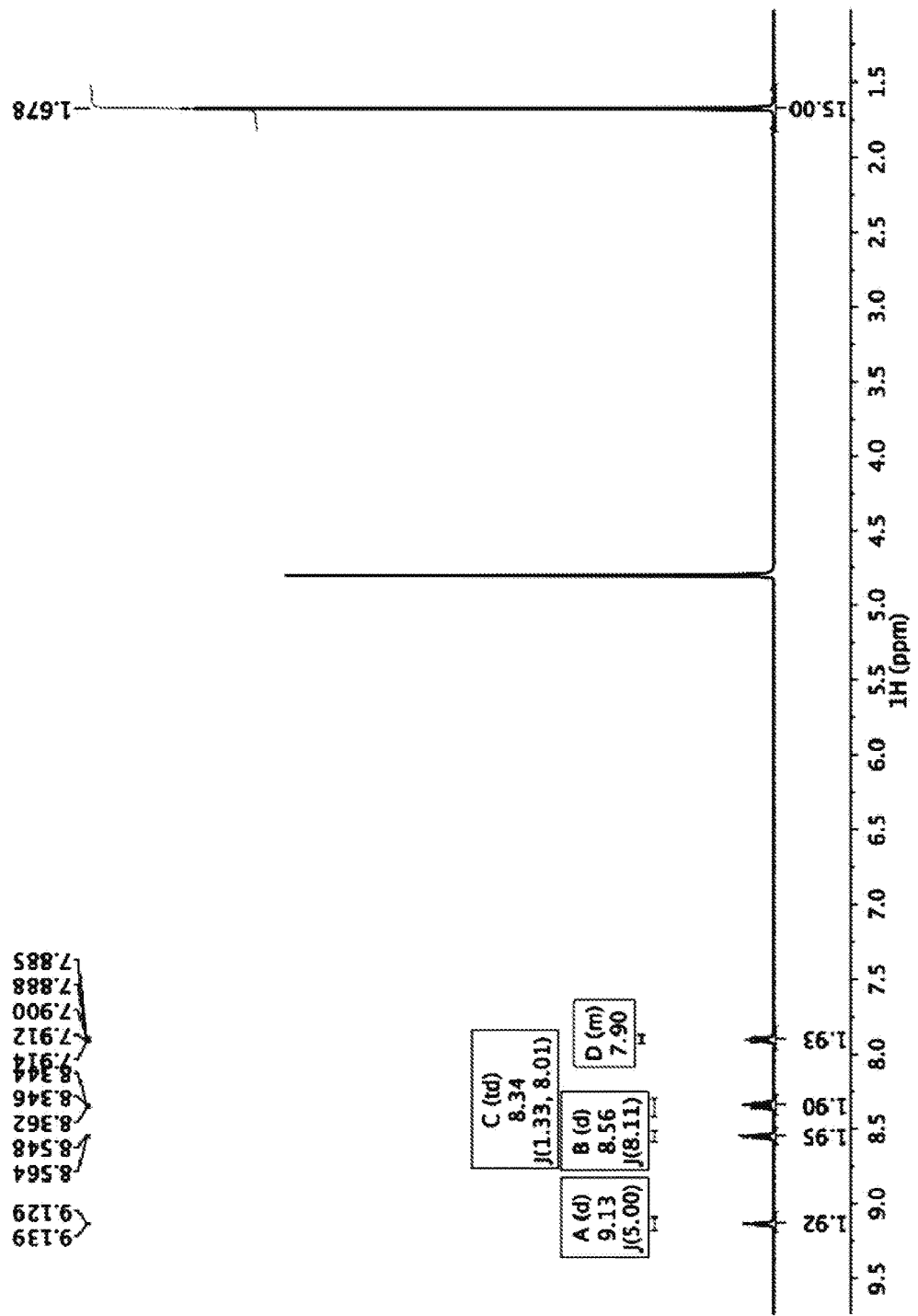
FIG. 17. $^1$H NMR spectrum of Ir catalyst 1 in D$_2$O (referenced to NaTSP).

To an orange suspension of 243.0 mg (0.305 mMol) [Cp*Ir(Cl)$_2$]$_2$ in 10 mL water stirring under a nitrogen atmosphere was added 95.3 mg (0.610 mMol) solid 2,2'-bipyridine. The suspension slowly turned yellow over a few minutes, and stirring was continued for 3 hours, at which point 313.5 mg (1.22 mMol) solid AgOTf was added. A white precipitate formed immediately. The reaction mixture was filtered through a sintered-glass frit loaded with celite and washed with water, affording a yellow filtrate which was dried in vacuo overnight to afford spectroscopically pure 1 (351.5 mg, 72% yield). The $^1H$ NMR spectrum matched the previously reported data (FIG. 17). Anal. calcd. for $C_{22}H_{25}F_6IrN_2O_7S_2$: C, 33.04; H, 3.15; N, 3.50. Found: C, 32.85; H, 2.95; N, 3.34.

FIG. 17 illustrates is a $^1H$ NMR spectrum of Ir catalyst 1 in $D_2O$ (referenced to NaTSP).

III. Procedures for Catalytic Reactions

A. Stock Solutions.

Formic acid stock solutions were made by dilution of 88% formic acid with either HPLC grade $H_2O$ or $D_2O$. In a typical preparation, 13.0 mL of formic acid was diluted to 100 mL, affording 3 M aqueous formic acid. The solutions were pH~1.4 under air and after degassing by sparging with $N_2$ for 20 minutes. Adjustments of pH were carried out by addition of $HBF_4$(aq) or NaOH(aq), and measured using pH electrodes (see General Considerations above); solutions pH adjusted with HCl showed no activity. In experiments using labeled formic acid, formic acid-$d_2$ (5% $D_2O$, 98% $^2H$) or formic acid-$^{13}C$ (4% $H_2O$, 99% $^{13}C$) were diluted with $D_2O$ to give the appropriate labeled stock solutions.

A solution of sodium tosylate was used as an internal standard. The sodium salt was dried under high vacuum for 18 hours before use. A 20 mL scintillation vial was charged with 291.3 mg (1.50 mMol) NaOTs and dissolved in 10 mL $D_2O$ to give a 150 mM NaOTs solution ($^1H$ NMR δ 2.388 vs. NaTSP). NaTSP was also occasionally used as an internal standard; however, NaTSP relaxes slowly and is quite hygroscopic, so it was not used to obtain absolute yields.

B. General Procedure for Catalytic Reactions.

Note:

Stock solutions of catalyst 1 in formic acid showed diminished activity after prolonged storage, even when stored at −35° C. Fresh solutions were made for each reaction.

NMR Scale.

In a typical reaction, 1.77 mg (2.22 μmol) of Ir catalyst 1 was dissolved in 1.00 mL of 3 M formic acid in $D_2O$ (2 mM in Ir). Addition of 50 μL of the stock solution and 350 μL of 3 M formic acid in $D_2O$ to a Teflon sealable NMR tube provided a 0.25 mM solution of 1. The tube was sealed, and the clear, bright yellow reaction mixture was heated at 80° C. Reactions were periodically cooled to room temperature and monitored by NMR spectroscopy. Fitting of the NMR lineshape of the methanol and methyl formate resonances with Gaussian functions (using MestReNova software) established a 12:9:1 ratio of $CHD_2OD:CH_2DOD:CH_3OD$ (see FIG. 22). The actual concentration of methanol and methyl formate was therefore estimated by multiplying the integrated area by 2.3 to account for partial deuteration. At intermediate reaction times, some of the methanol was converted to methyl formate; all values of methanol include both methanol and methyl formate. At complete consumption of formic acid, only methanol was present. For monitoring reaction kinetics, a known amount of NaOTs internal standard was added, and careful temperature control was maintained (±0.2° C.). The tubes were removed from the oil bath to an ice bath to stop the reaction periodically for NMR spectroscopic analysis. Data was treated in the MestreNova software suite, using 1 Hz line broadening and Whittaker smoother baseline correction. The NMR experiments showed higher selectivity for methanol due to the use of $D_2O$ as solvent. This was confirmed by comparison of $D_2O$ and $H_2O$ solvents in the multi-reactor (procedure below), which showed a similar selectivity enhancement in $D_2O$.

Pressure Vials.

Test reactions were carried out in 20 mL scintillation vials equipped with septum caps designed to rupture at 150 psi (ChemGlass CG-4912-05). Solutions of 1 in aqueous formic acid were prepared in a glovebox, added to the pressure vials with a stirbar, and sealed. The reaction vials were removed from the glovebox and submerged in an oil bath heated to the appropriate temperature. After the desired reaction time, the vials were submerged in an ice bath, and a 100-200 μL portion of 150 mM sodium tosylate $D_2O$ solution was added by syringe. The mixture was shaken well to mix evenly, and an aliquot was removed and analyzed by $^1H$ NMR (60 second delay time).

Multi-Reactor.

Up to 6 reactions could be run in parallel using a Series 5000 multi-reactor from Parr Instrument Company. The reactor vessels were oven-warmed (>140° C.), while the reactor heads were gently warmed on top of the oven, and the separate parts were pumped into the glovebox for assembly. A custom-designed, snug-fitting PTFE insert lined the walls of the reactor vessel (total volume~46 mL). The lined reactors were charged with an appropriate formic acid solution of catalyst 1 and a stirbar, and sealed. One vessel was generally retained as a control reaction, usually by omission of the catalyst; no methanol was ever observed in these controls, with <0.1 atm pressure increase typically observed over 24 hours. Vessels were moved to the reactor assembly, stirred at 300 rpm, and the temperature of each vessel was adjusted using the accompanying software. If required, hydrogen pressure was applied after purging the manifold and the vessel headspace. Pressure was monitored in real-time using the digital pressure gauge. After the desired reaction time, the reactors were allowed to cool, then submerged in an ice bath and vented. A 100-200 μL portion of 150 mM sodium tosylate in $D_2O$ was added by syringe. The mixture was shaken well to mix evenly, and an aliquot was removed and analyzed by $^1H$ NMR (60 second delay time). At intermediate reaction times, methyl formate (produced by condensation of methanol and formic acid) was detected; methanol yields include both methanol and methyl formate. At complete consumption of formic acid, only methanol was present. Reactions carried out with sodium tosylate as part of the reaction mixture gave similar results. Conversion values for reactions run with 12 M initial formic acid concentration were obtained by addition of a second internal standard of dioxane. After carrying out the procedure above using NaOTs for methanol quantification, the contents of the NMR tube were returned to the reaction vessel, and dioxane was added (concentration of dioxane in reaction mixture: 1.5 M). The mixture was shaken well, and an aliquot was removed for $^1H$ NMR spectroscopic analysis.

Reactions were carried out varying temperature, [FA], pH, and $H_2$ pressure. Tables compiling average data from at least 2 experiments are presented in the following tables. The average values are given, with estimated uncertainty in parentheses. Our conservative estimation of uncertainty was based on the standard deviation of 2-5 reactions, and variations in $^1H$ NMR integration. Different batches of catalyst (using distinct sources of Ir and bpy) and formic acid gave similar results. Definitions: turnover number (TON) is moles of methanol (and methyl formate when present) divided by moles of catalyst. Turnover frequency (TOF) is TON divided by time, in hours; TOF is given after 24 hours (<50% conversion) in most cases. Conversion is moles of formic acid consumed divided by the initial moles of formic acid. Selectivity for methanol is three times the moles of methanol (accounting for reaction stoichiometry) produced divided by the amount of formic consumed.

Figure 18:
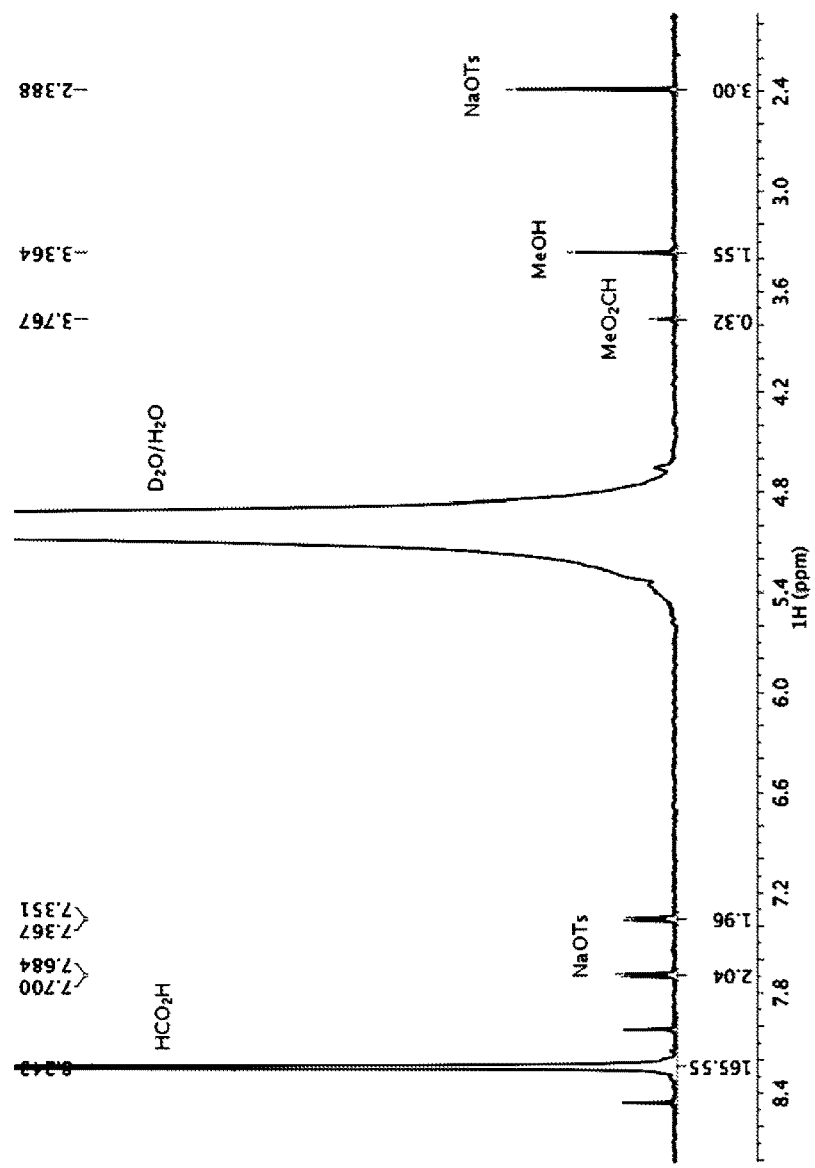
FIG. 18. Typical $^1$H NMR spectrum after workup of formic acid disproportionation catalyzed by [Cp*Ir(bpy)(H$_2$O)]2+.

FIG. 18 illustrates a typical $^1H$ NMR spectrum after workup of formic acid disproportionation catalyzed by $[Cp*Ir(bpy)(H_2O)]^{2+}$.

TABLE 6

Effect of temperature on reaction. Conditions: 0.25 mM Ir, 3M formic acid, 80° C., 24 hours.

| Temp (° C.) | TON | TOF ($h^{-1}$) | Conversion (%) | MeOH Selectivity (%) | MeOH Yield (%) |
|---|---|---|---|---|---|
| 60 | 17(1) | 0.7(1) | 6(3) | 8(2) | 0.43(4) |
| 70 | 26(1) | 1.1(1) | 11(3) | 6(1) | 0.64(4) |
| 80 | 34(1) | 1.4(1) | 23(3) | 4(1) | 0.82(4) |
| 90 | 46(1) | 2.0(1) | 31(3) | 4(1) | 1.2(4) |
| 100 | 46(1) | 2.0(1) | 58(3) | 2(1) | 1.1(4) |

Figure 19:
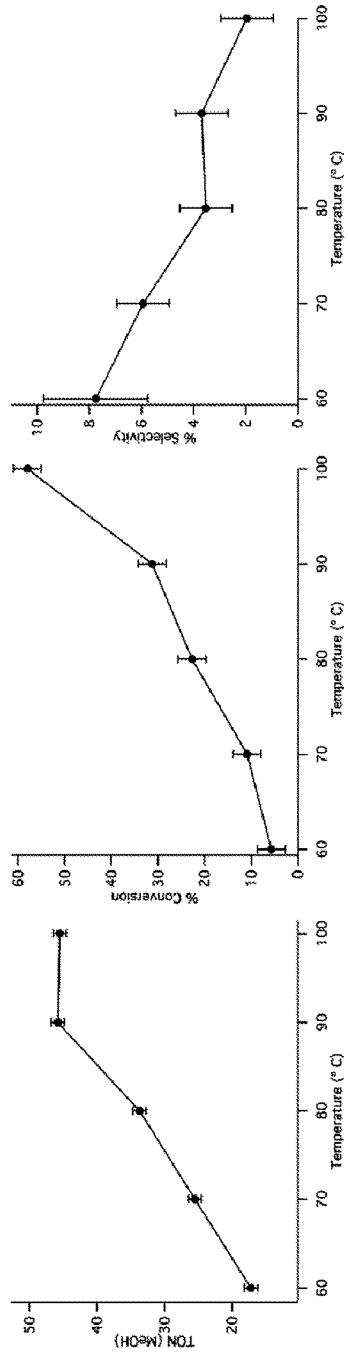
FIG. 19. Plots showing impact of reaction temperature on TON (left), % conversion (middle) and % methanol selectivity (right). Conditions: 0.25 mM 1, 3 M formic acid, 24 hours.

FIG. 19 illustrates plots showing impact of reaction temperature on TON (left), % conversion (middle) and % methanol selectivity (right). Conditions: 0.25 mM 1, 3 M formic acid, 24 hours.

TABLE 7

Effect of [FA] on reaction. pH was adjusted to 1.4 by $HBF_4$(aq) or NaOH(aq). Conditions: 0.25 mM 1, 80° C., 24 hours.

| [Formic acid] (M) | TON | TOF ($h^{-1}$) | Conversion (%) | MeOH Selectivity (%) | MeOH Yield (%) |
|---|---|---|---|---|---|
| 0.5 | 4(1) | 0.2(1) | 97(1) | 0.6(1) | 0.08(4) |
| 1 | 16(1) | 0.7(1) | 83(2) | 1(1) | 0.36(4) |
| 3 | 34(1) | 1.4(1) | 23(3) | 4(1) | 0.82(4) |
| 6 | 36(1) | 1.5(1) | 9(3) | 5(1) | 0.83(4) |
| 12 | 62(3) | 2.6(1) | 4(3) | 10(1) | 1.4(4) |

TABLE 8

Effect of pH (adjusted by $HBF_4$(aq) or NaOH(aq)) on reaction. Conditions: 0.25 mM 1, 3M formic acid, 80° C., 24 hours.

| pH | TON | TOF ($h^{-1}$) | Conversion (%) | MeOH Selectivity (%) | MeOH Yield (%) |
|---|---|---|---|---|---|
| 0.5 | 70(2) | 2.9(1) | 48(3) | 4(1) | 1.8(4) |
| 1.0 | 79(2) | 3.3(1) | 51(3) | 4(1) | 2.0(4) |
| 1.4 | 34(1) | 1.4(1) | 23(3) | 4(1) | 0.82(4) |
| 2.0 | 14(1) | 0.6(1) | 8(3) | 4(1) | 0.35(4) |

TABLE 9

Effect of dihydrogen on reaction. Conditions: 0.25 mM 1, 3M formic acid, 80° C., 24 hours.

| Pressure, Gas | TON | TOF ($h^{-1}$) | Conversion (%) | MeOH Selectivity (%) | MeOH Yield (%) |
|---|---|---|---|---|---|
| 1 atm $N_2$ | 34(1) | 1.4(1) | 23(3) | 4(1) | 0.82(4) |
| 15 atm, $H_2$ | 34(1) | 1.4(1) | 18(3) | 5(1) | 0.90(4) |
| 30 atm, $H_2$ | 38(1) | 1.6(1) | 16(3) | 6(1) | 0.94(4) |

FIG. 20 illustrates plots showing effect of $H_2$ pressure on TON (left), % conversion (middle) and % methanol selectivity (right). Conditions: 0.25 mM 1, 3 M formic acid, 80° C., 24 hours.

Analysis of Kinetic Dependence of the Reaction on [Ir].

Kinetic analysis of catalytic reactions at different catalyst loading provided accurate data on initial rates. Reactions were monitored by $^1$H NMR spectroscopy up until ~25% conversion in Teflon-sealed tubes. Above ~25% conversion, the tubes were vented periodically to avoid pressure buildup. Representative data are shown below. Only a small Ir—H resonance was observed in $HCO_2H/D_2O$ mixtures, consistent with rapid H/D exchange at the hydride position in acidic conditions, and consistent with the formation of various methanol isotopologue products. The spectrum of isolated 2 in $D_2O$ overlaid nearly exactly with the species formed in 3 M $HCO_2H/D_2O$. The data in Table 5 of the main text was obtained by averaging the values of TON, TOF, conversion, and selectivity obtained with [1]=0.25 mM at ~24 hours (three runs: 20, 21, 26 h).

FIG. 21 illustrates $^1$H NMR spectra following a catalytic reaction (Cp* region). Early spectra show hydride 2 (δ 1.81) as the major species in solution, along with formate 3 (δ 1.66). As the reaction proceeds, 2 and 3 are consumed and new, unidentified resonances appear. Reaction conditions: 1 mM 1, 3 M formic acid in $D_2O$, 80° C.

Figure 22:
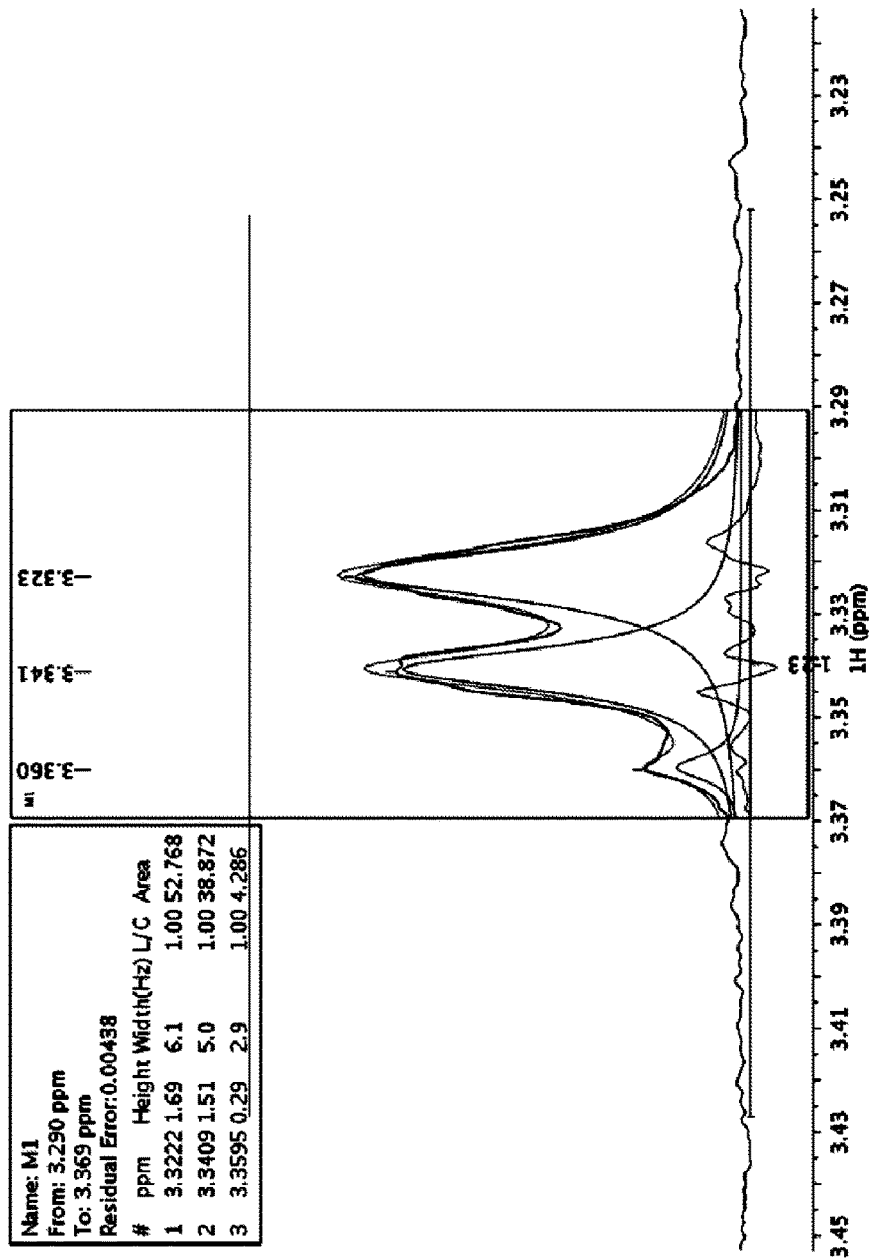
FIG. 22. Representative Gaussian fitting of methanol isotopologues using MestReNova software; 55% $CHD_2OD$, 40.5% $CH_2DOD$, and 4.5% $CH_3OD$. These values were used to correct for the amount of methanol formed in NMR-scale reactions. Reaction conditions: 0.0625 mM 1, 3 M formic acid in $D_2O$, 44 hours.

FIG. 22 illustrates representative Gaussian fitting of methanol isotopologues using MestReNova software; 55% $CHD_2OD$, 40.5% $CH_2DOD$, and 4.5% $CH_3OD$. These values were used to correct for the amount of methanol formed in NMR-scale reactions. Reaction conditions: 0.0625 mM 1, 3 M formic acid in $D_2O$, 44 hours.

FIG. 23 illustrates log-log plot of initial rate of methanol formation vs. [Ir], with linear fit (average of 2 runs). Slope of 1 indicates first-order dependence on catalyst. Reaction conditions: 0.125-1 mM 1, 3 M formic acid in $D_2O$, 80° C., initial rates from linear fits to first 10-20 hours of reaction.

FIG. 24 illustrates log-log plot of rate of consumption of formic acid vs. concentration of iridium. Slope of 1 indicates that overall formic acid decomposition (to $H_2/CO_2$ and to $CH_3OH$) is first order in catalyst. Reaction conditions: 0.125-1 mM 1, 3 M formic acid in $D_2O$, 80° C.

FIG. 25 illustrates time course of methanol formation when 1 mM 1 was used as catalyst. Inset shows early reaction times. Reaction conditions: 1 mM 1, 3 M formic acid in $D_2O$, 80° C.

Figure 26:
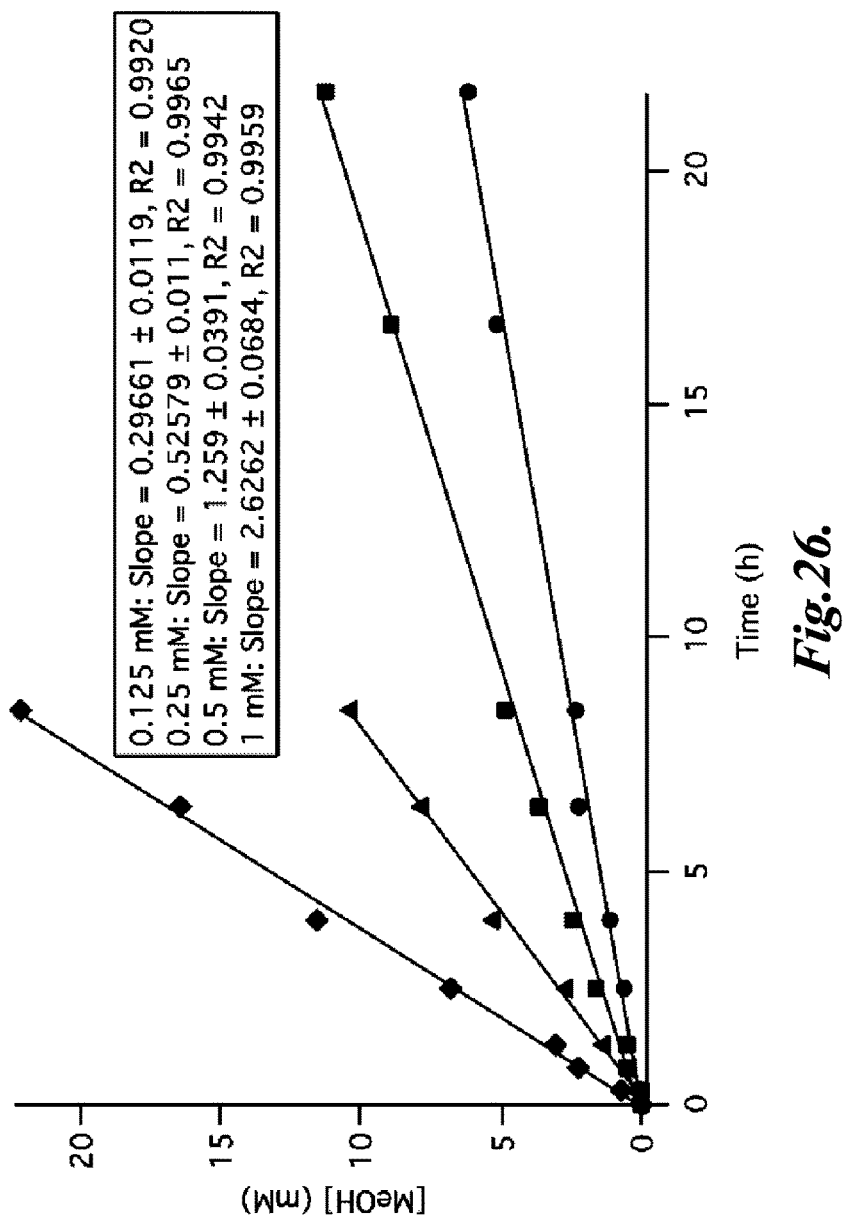
FIG. 26. Overlaid plots of concentration of MeOH (mM) vs. time (h), with linear fits. Black circles, 0.125 mM 1; red squares, 0.25 mM 1; green triangles, 0.5 mM 1; blue diamonds, 1 mM 1. Reaction conditions: 3 M formic acid in $D_2O$, 80° C.

FIG. 26 is overlaid plots of concentration of MeOH (mM) vs. time (h), with linear fits. Black circles, 0.125 mM 1; red squares, 0.25 mM 1; green triangles, 0.5 mM 1; blue diamonds, 1 mM 1. Reaction conditions: 3 M formic acid in $D_2O$, 80° C.

Figure 27:
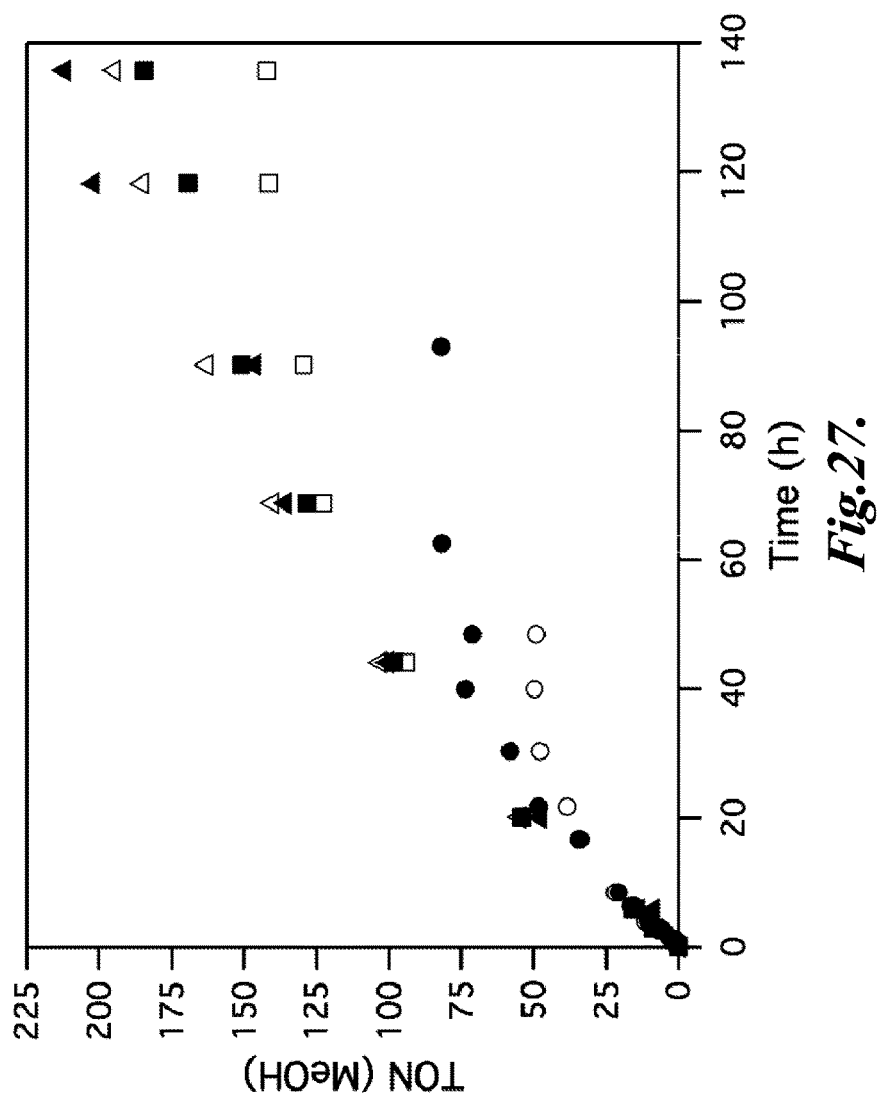
FIG. 27. TON for MeOH production vs. time at various catalyst loadings. Empty circles, 1 mM 1; filled circles, 0.5 mM 1; empty squares, 0.25 mM 1; filled squares, 0.125 mM 1; empty triangles, 0.0625 mM 1; filled triangles, 0.0313 mM 1. Reaction conditions: 3 M formic acid in $D_2O$, 80° C.

FIG. 27 illustrates TON for MeOH production vs. time at various catalyst loadings. Empty circles, 1 mM 1; filled circles, 0.5 mM 1; empty squares, 0.25 mM 1; filled squares, 0.125 mM 1; empty triangles, 0.0625 mM 1; filled triangles, 0.0313 mM 1. Reaction conditions: 3 M formic acid in $D_2O$, 80° C.

C. Control Reactions.

Heating 3 M solutions of formic acid as high as 100° C. resulted in negligible consumption of formic acid, and no detectable methanol.

Heating 2.2 mg (0.0141 mMol) of 2,2'-bipyridine in 1 mL 3 M formic acid to 80° C. for 24 hours resulted in a color change of the reaction mixture from colorless to pale pink. After standard work up, no methanol and was observed by $^1$H NMR spectroscopy, and negligible amounts of formic acid were consumed.

Simple Ir complexes $[Cp*Ir(Cl)_2]_2$ and $[Cp*Ir(H_2O)_3][SO_4]$ were also tested under standard conditions (80° C., 24 hours, 3 M formic acid). After standard work up, significant consumption of formic acid was observed, but no methanol was detectable by $^1$H NMR spectroscopy.

D. Homogeneity Tests.

Mercury Drop Test.

Figure 28:
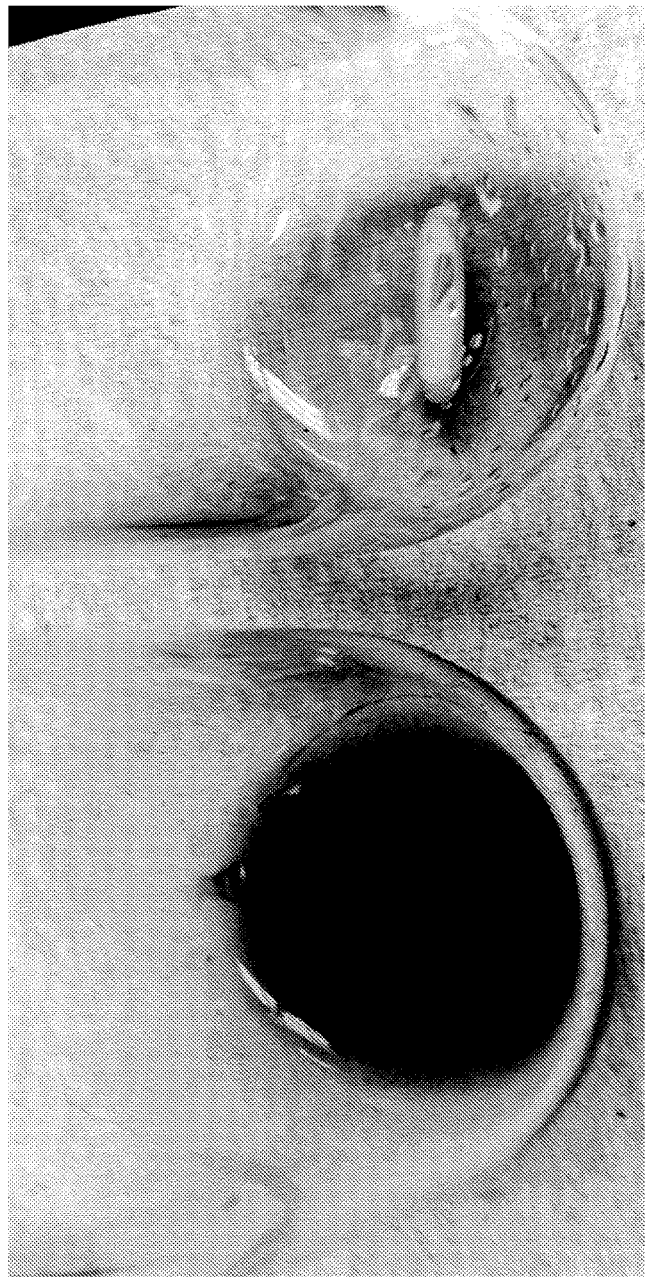
FIG. 28. Photograph of a reaction mixture of 1 mM catalyst 1 in 3 M formic acid that was split into two vessels and heated to 100° C. (left) and 80° C. (right), after two 24 hour cycles.
Figure 29:
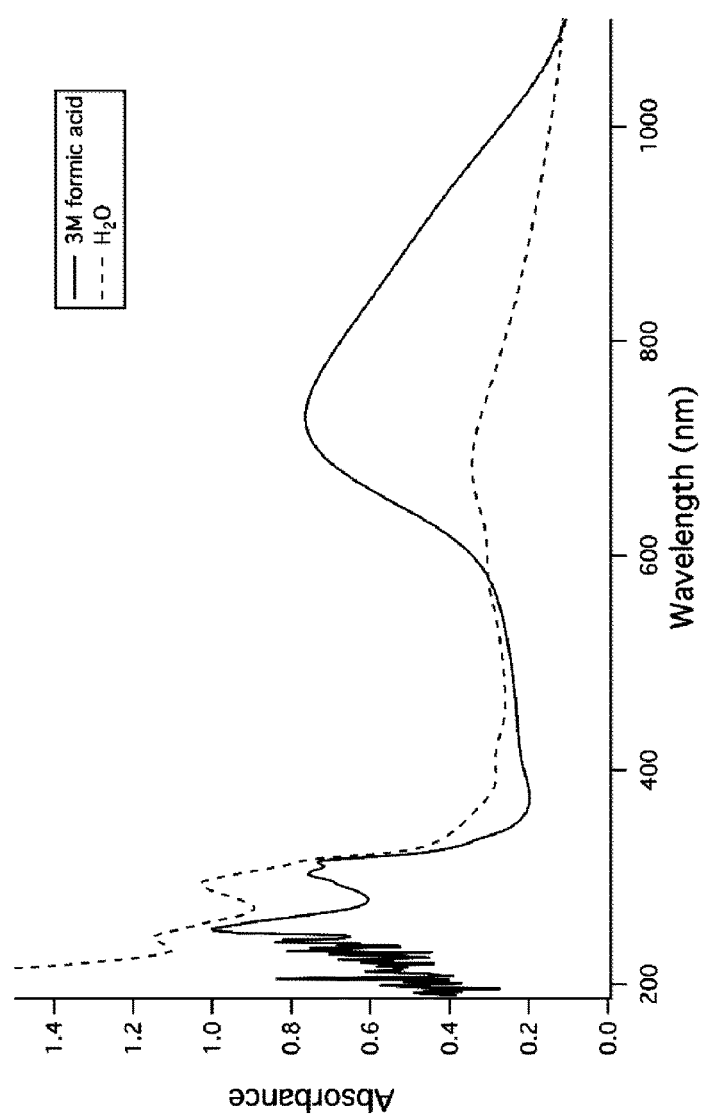
FIG. 29. UV-visible spectra of the decomposed catalyst material after 4 reaction cycles at 100° C. The solid trace shows is in 3 M formic acid, and the dotted trace is in water (material was sparingly soluble).

In a glovebox, 1 mL of 1 mM 1 in 3 M formic acid was added to two 20 mL vials. Each vial was equipped with a stir bar, and to one vial was added 2 g of elemental mercury. The two solutions were both bright yellow, and the mercury drop was bright and shiny metallic. The vials were capped and sealed with electrical tape, removed from the box and heated to 80° C. in an oil bath. After 15 hours of heating with vigorous stirring, the reactions were removed from the oil bath and submerged in an ice bath. The solutions both appeared yellow-orange, and the mercury drop appeared as shiny and metallic as it did at the start of the reaction. 100 µL of 50 mM NaTSP in $D_2O$ was added to each, and the vials were shaken well to mix. $^1H$ NMR spectroscopy revealed 27.4 µmoles of MeOH (TON=26.1) without the mercury drop, and 27.2 µmoles of MeOH (TON=25.9) in the presence of the mercury drop. The reactions were repeated in a separate experiment with the same results. Recycle experiments at 80 and 100° C. In a glovebox, two 50 mL Teflon-sealable pressure vessels equipped with magnetic stir bars were each charged with 1 mL of 3 M formic acid containing 1 mM Ir catalyst 1. One vessel was heated to 80° C., and the other was heated to 100° C. After heating with stirring for 24 hours, the reactions were allowed to cool. The reaction carried out at 80° C. maintained a bright yellow color, while the reaction carried out at 100° C. was a darker purple color. The reaction vessels were each attached to a vacuum line through a small trap cooled with liquid nitrogen. Volatiles were removed under reduced pressure and collected in the liquid nitrogen-cooled trap. 100 µL of 150 mM NaOTs in $D_2O$ was added by syringe to the volatiles, and an aliquot was examined by $^1H$ NMR spectroscopy. The reaction vessels, containing orange-yellow and purple-blue solids, respectively, were sealed under vacuum and brought into a glovebox. A 1 mL portion of 3 M formic acid was added to each reaction vessel, and the mixture was shaken to dissolve the solids. The vessels were sealed and heated again for 24 hours at 80° C. or 100° C. The hot reaction continued to darken, and contained some insoluble solids. A photograph after the second 24 hour reaction cycle is shown in FIG. 28. The procedure was repeated 3 times in this manner. A fourth cycle was completed with both vessels heated to 80° C., to ensure that the blue-purple mixture was not active at 80° C. The results are tabulated in Table 10. UV-vis spectra of the blue solids after the recycle experiment were obtained in degassed water (solids were slightly soluble) and 3 M formic acid (solids were mostly soluble), with spectra shown in FIG. 29. FIG. 28 illustrates a photograph of a reaction mixture of 1 mM catalyst 1 in 3 M formic acid that was split into two vessels and heated to 100° C. (left) and 80° C. (right), after two 24 hour cycles. FIG. 29 illustrates UV-visible spectra of the decomposed catalyst material after 4 reaction cycles at 100° C. The solid trace shows is in 3 M formic acid, and the dotted trace is in water (material was sparingly soluble).

TABLE 10

Catalyst recycle experiments. Conditions: 1 mM catalyst 1, 3M formic acid, 80 or 100° C.

| Run | TON | TOF ($h^{-1}$) | Conversion (%) | MeOH Selectivity (%) | Overall MeOH Yield (%) | Retention of Activity (%) |
|---|---|---|---|---|---|---|
| 80° C. Recycle |||||||
| 1 | 25.5 | 1.1 | 50 | 5.1 | 2.6 | 100 |
| 2 | 21.8 | 0.91 | 53 | 4.1 | 2.2 | 85 |
| 3 | 20.1 | 0.84 | 70 | 2.9 | 2.0 | 79 |
| 4 | 17.5 | 0.73 | 82 | 2.1 | 1.8 | 69 |
| 100° C. Recycle |||||||
| 1 | 21 | 0.88 | 100 | 2.1 | 2.1 | 100 |
| 2 | 9.6 | 0.40 | 100 | 0.96 | 0.96 | 46 |
| 3 | 2.95 | 0.12 | 100 | 0.30 | 0.30 | 14 |
| 4 | 1 | 0.04 | 100 | 0.10 | 0.10 | 4.8 |

FIG. 30 illustrates plots of recycle experiments at 80° C. (filled circles) and 100° C. (empty circles). The fourth run of the 100° C. recycle experiment was run at 80° C. Left plot shows changes in turnover number when volatiles were removed at the end of the reaction and replaced with fresh 3 M formic acid, while right plot shows changes in % consumption of formic acid. Conditions: 1 mM catalyst 1, 3 M formic acid, 24 hours.

E. Confirming the Identity of Organic Products.

Methanol.

Figure 31:
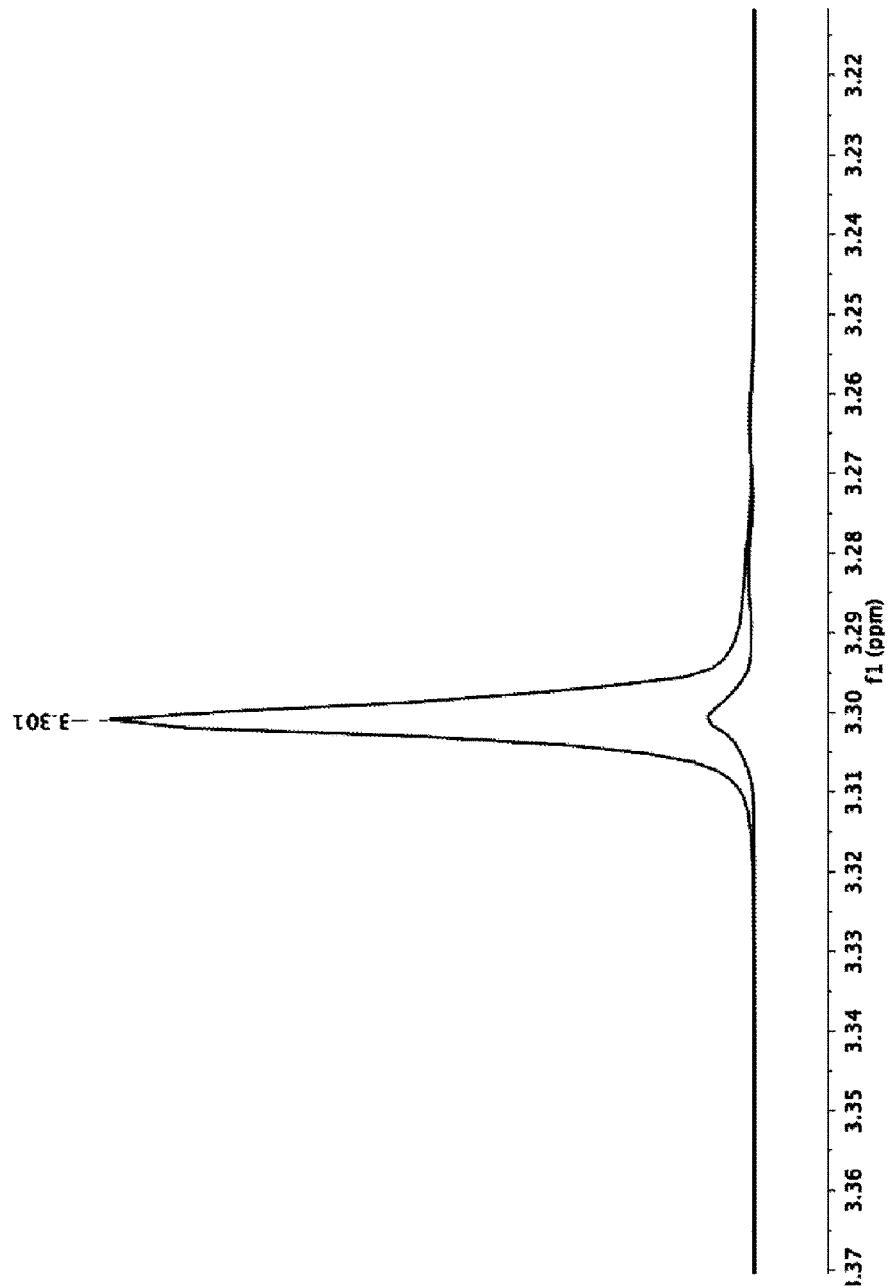
FIG. 31. Partial $^1H$ NMR spectrum showing methanol region of reaction mixture (smaller peak), and after addition of an authentic methanol sample (large peak).

Methanol was identified to be the reaction product by spiking with an authentic sample and by GC-MS analysis. In each case, catalyst 1 was dissolved in 3 M $HCO_2H/D_2O$ (~5 mM) and heated to 100° C. in an NMR tube (Caution: these test reactions unexpectedly built significant pressure). After 8 hours, the dark purple reaction mixtures were attached to a high vacuum line via a small trap. The trap was cooled with liquid nitrogen and the volatiles were removed under vacuum. In one experiment, the volatiles were analyzed by $^1H$ NMR spectroscopy, and then re-analyzed after addition of 10 µL of MeOH (FIG. 31). The suspected methanol peak grew in intensity upon addition of the authentic sample of methanol. In a separate experiment, the volatiles were analyzed by GC-MS, and showed the same retention time as an authentic sample of methanol, but a more complicated mass spectrum consistent with a mixture of $d_0$, $d_1$, and $d_2$ isotopologues (the same mixture observed by $^1H$ NMR spectroscopy). GC-MS of the product of reactions carried out in $HCO_2H/H_2O$ featured the same retention time as methanol and m/z=32, as expected for unlabeled methanol.

FIG. 31 illustrates partial $^1H$ NMR spectrum showing methanol region of reaction mixture (smaller peak), and after addition of an authentic methanol sample (large peak).

Methyl Formate.

A reactor was charged with 2 mL of 6 M formic acid (pH 1.4) containing 0.25 mM Ir precatalyst 1, and heated at 80° C. for 24 hours. Standard workup and $^1H$ NMR spectroscopic analysis showed the presence of methanol and methyl formate. To the NMR tube was then added 1 µL (16.2 µmol) of an authentic sample of methyl formate (Aldrich, anhydrous, 99%) by microliter syringe. Subsequent $^1H$ NMR spectroscopic analysis showed an increase in two resonances (FIG. 32): δ 3.777 (s, 3H) and 8.157 (s, 1H). Methyl formate was therefore assigned as the minor product in the formic acid disproportionation. When reactions were run to complete conversion, methanol was the only soluble product observed.

Figure 32:
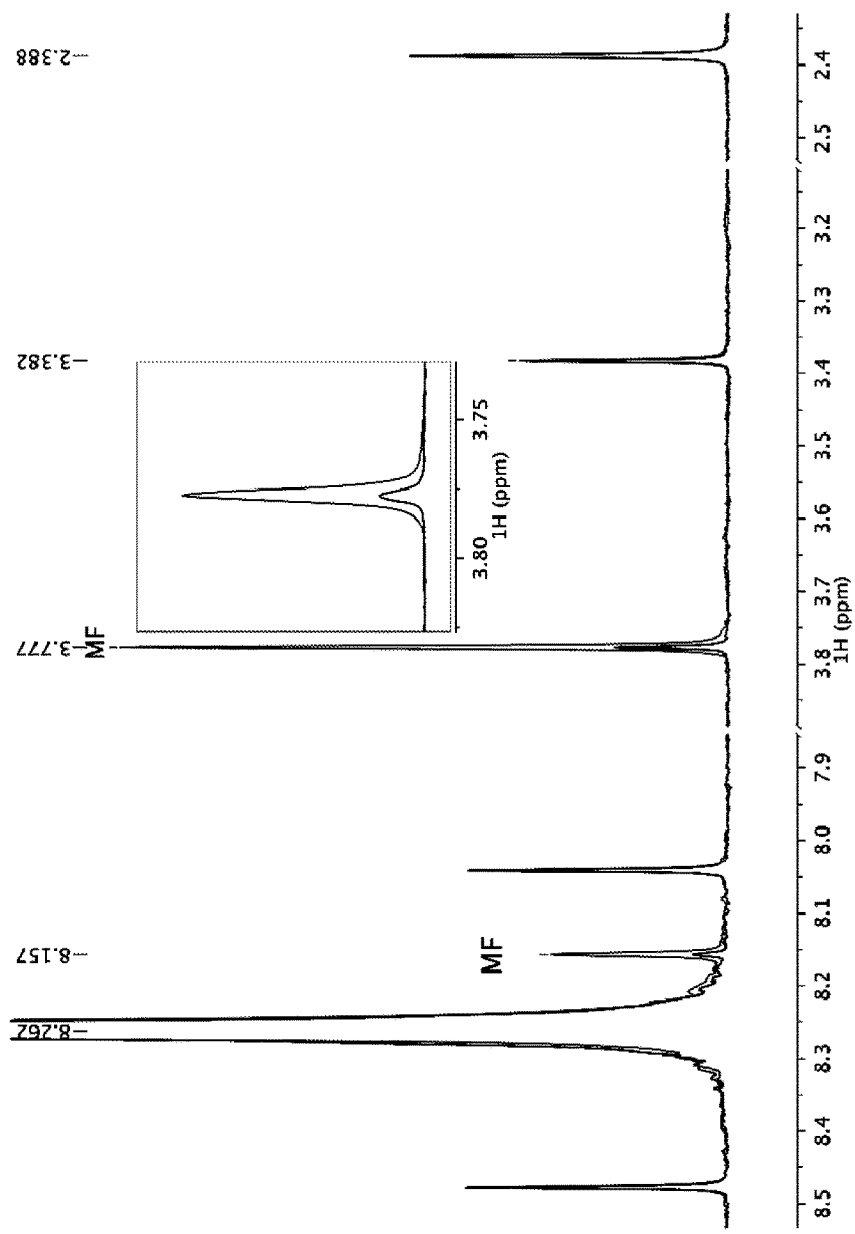
FIG. 32. $^1H$ NMR spectra of a typical post-reaction mixture containing formic acid (δ 8.26), methanol (δ 3.382), methyl formate (δ 3.777, 8.157, labeled "MF") and NaOTs internal standard (δ 2.388, other resonances omitted). The identity of methyl formate was confirmed by comparison of spectra from initial reaction workup and after spiking with an authentic sample of methyl formate. Inset shows close-up of methyl group of methyl formate.

FIG. 32 illustrates $^1H$ NMR spectra of a typical post-reaction mixture containing formic acid (δ 8.26), methanol (δ 3.382), methyl formate (δ 3.777, 8.157, labeled "MF") and NaOTs internal standard (δ 2.388, other resonances omitted). The identity of methyl formate was confirmed by comparison of spectra from initial reaction workup and after spiking with an authentic sample of methyl formate. Inset shows close-up of methyl group of methyl formate.

$H_2$ and $CO_2$.

Figure 33:
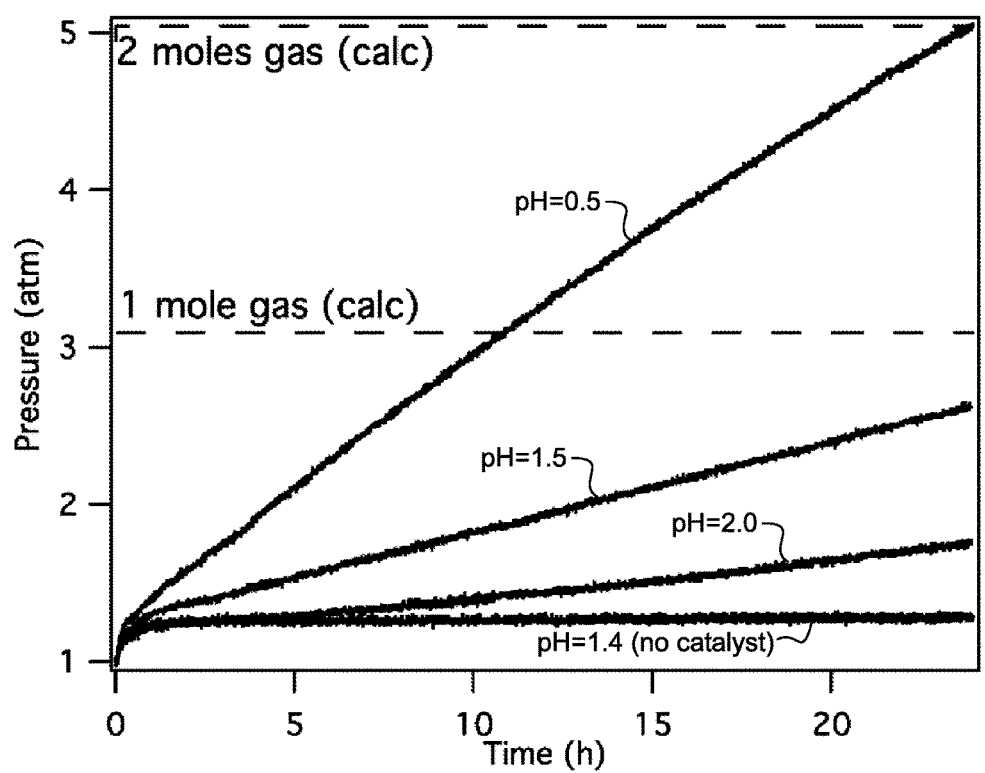
FIG. 33. Plot of the pressure in the reactors over time at various pH. pH 0.5; pH 1.4; pH 2.0; and pH 1.4, in the absence of catalyst 1. The dotted lines show the calculated pressure level expected for pH 0.5 after 24 hours for a combination of disproportionation/dehydrogenation (2 moles of gas) and for a combination of disproportionation/dehydration (1 mole of gas). Conditions: 3 M $HCO_2H$, pH adjusted with $HBF_4$/NaOH, 0.25 mM 1, 80° C.

The most common decomposition of formic acid solutions is the production of $H_2$ and $CO_2$ (11). $H_2$ and $CO_2$ were observed qualitatively as described below by $^1H$ and $^{13}C$ NMR spectroscopy. No CO was observed by $^{13}C$ NMR spectroscopy when $^{13}C$ labeled formic acid was employed as the substrate in a sealed NMR tube. In further support, pressure increases in sealed reactor vessels were consistent a combination of disproportionation (⅔ moles of gas released per mole of formic acid consumed) and dehydrogenation (2 moles of gas released per mole of formic acid consumed). For example, when 3 M formic acid (pH adjusted to 0.5) containing 0.25 mM 1 was heated to 80° C., NMR integration after 24 hours showed 35.7 μmoles MeOH, resulting from consumption of 107 μmoles of formic acid with expected release of 71.4 μmoles of gas. NMR integration of formic acid corresponded to 49% conversion, with 2.91 mMoles formic acid consumed. Correction for the formic acid converted to methanol leaves 2.8 mMoles formic acid consumed in other reactions. By the ideal gas law, if the remaining formic acid decomposed to give 2 moles of gas (in the case of $CO_2/H_2$ release), the vessel headspace pressure should increase by a total of 3.74 atm. On the other hand, if only 1 mole of gas is liberated (in the case of CO release), the pressure change is predicted to be only 1.89 atm. The observed pressure increase in the reactor was 3.84 atm, in good agreement with the calculated estimate (FIG. 33). All of the reactions were within ~10% of the value expected for a combination of disproportionation and dehydrogenation, with relatively large uncertainty deriving from NMR integration of a large resonance. While small amounts of CO cannot be ruled out, the data clearly point to dehydrogenation of formic acid to release $CO_2$ and $H_2$ as the major competing reaction.

FIG. 33 illustrates a plot of the pressure in the reactors over time at various pH. pH 0.5; pH 1.4; pH 2.0; and pH 1.4, in the absence of catalyst 1. The dotted lines show the calculated pressure level expected for pH 0.5 after 24 hours for a combination of disproportionation/dehydrogenation (2 moles of gas) and for a combination of disproportionation/dehydration (1 mole of gas). Conditions: 3 M $HCO_2H$, pH adjusted with $HBF_4$/NaOH, 0.25 mM 1, 80° C.

F. Confirming that Formic Acid is the Source of Methanol and Methyl Formate.

$^{13}C$ Labeled Formic Acid Experiment.

Figure 34:
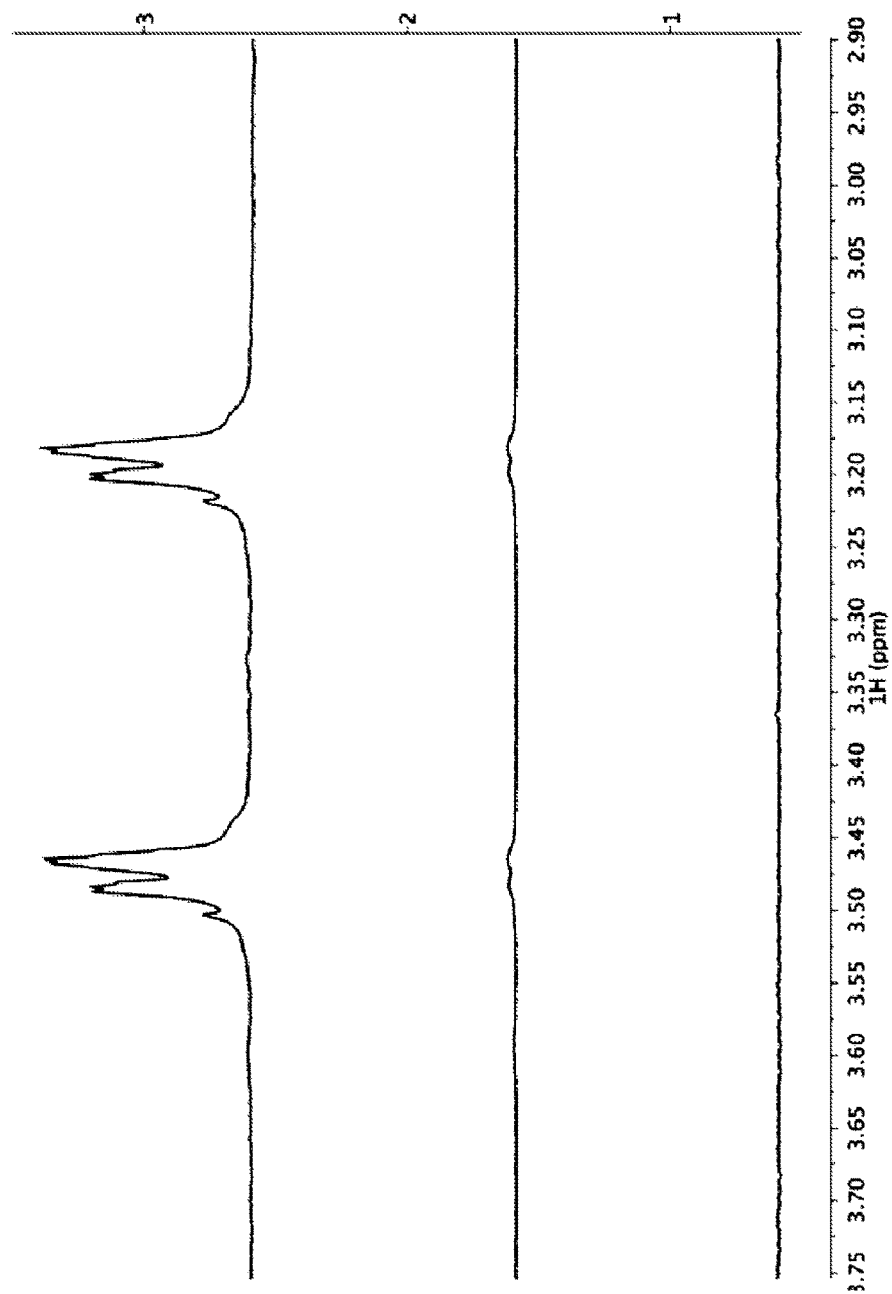
FIG. 34. Partial $^1H$ NMR spectra illustrating the time course of methanol production from $H^{13}CO_2H$. Bottom: before heating; middle: after 1 hour at 75° C.; top, after 24 hours at 75° C. Reaction conditions: ~4 mM 1, 3 M $H^{13}CO_2H$ in $D_2O$.

In a glovebox, 1.2 mg ($1.5 \times 10^{-6}$ mol) catalyst 1 was dissolved in 0.4 mL 3 M formic acid-$^{13}C$ $D_2O$ solution. The mixture was transferred to a Teflon-sealed NMR tube. A $^1H$ NMR spectrum was obtained, and the reaction mixture was then heated to 75° C. After 1 hour, a small amount of methanol-$^{13}C$ (δ ~3.34, d, $J_{CH}$=142 Hz) was observed by $^1H$ NMR, which grew significantly over 24 hours (FIG. 34). The methanol was ~90% $^{13}C$ labeled, with the expected array of isotopologues ($HO^{13}CH_3$, $HO^{13}CHD_2$, $HO^{13}CH_2D$) because of the deuterated solvent. Strong signals for the same methanol isotopologues were observed by $^{13}C\{^1H\}$ NMR, in addition to large amounts of $^{13}CO_2$. No $^{13}CO$ was observed. Vacuum transfer of the volatiles into another NMR tube containing $C_6D_6$ allowed observation of $H_2$ (s, δ 4.47) and HD (δ 4.43, 1:1:1 t, $J_{HD}$=42.7 Hz) by $^1H$ NMR spectroscopy ($H_2$ is not appreciably soluble in aqueous solutions).

FIG. 34 illustrates partial $^1H$ NMR spectra illustrating the time course of methanol production from $H^{13}CO_2H$. Bottom: before heating; middle: after 1 hour at 75° C.; top, after 24 hours at 75° C. Reaction conditions: ~4 mM 1, 3 M $H^{13}CO_2H$ in $D_2O$.

Figure 35:
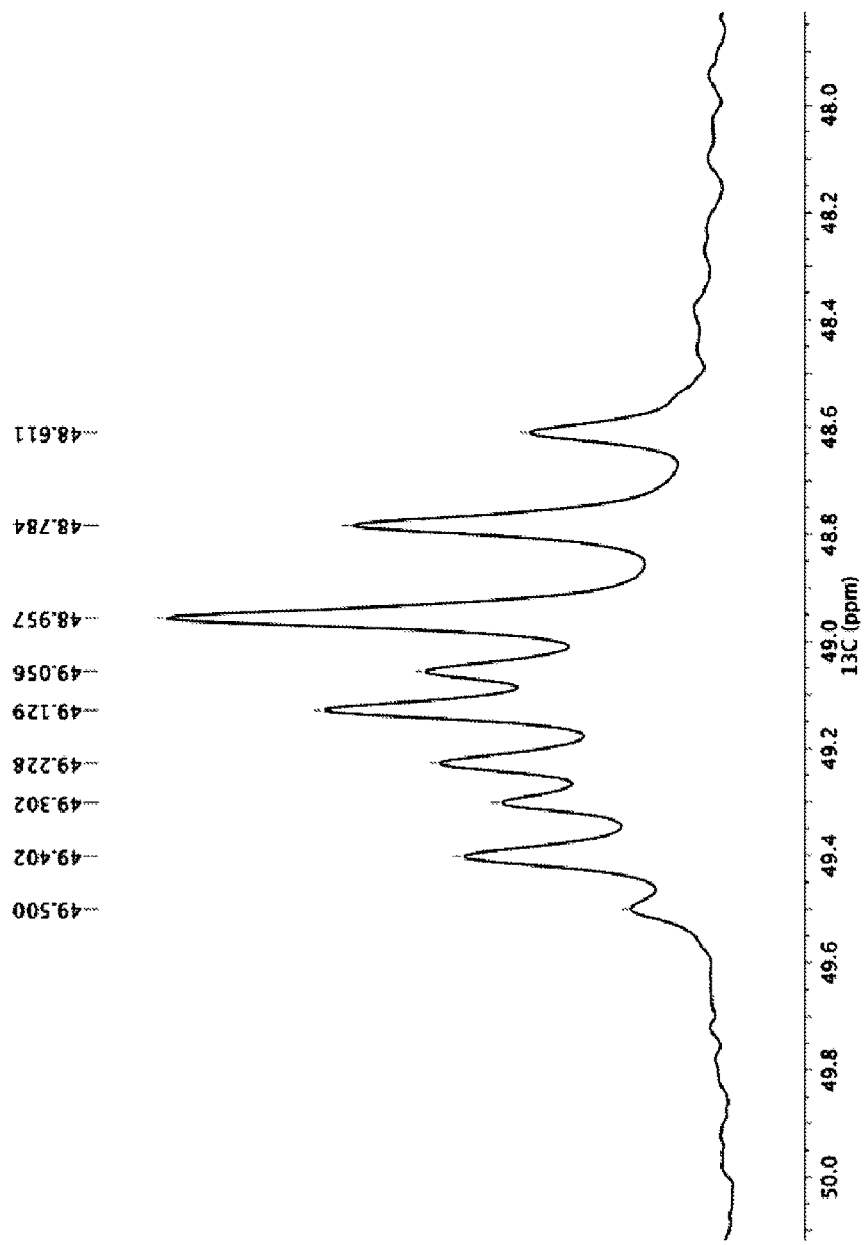
FIG. 35. Partial $^{13}C\{^1H\}$ NMR spectrum showing methanol region after a 3 M $H^{13}CO_2H/D_2O$ solution containing ~4 mM 1 was heated at 75° C. for 24 hours.

FIG. 35 illustrates partial $^{13}C\{^1H\}$ NMR spectrum showing methanol region after a 3 M $H^{13}CO_2H/D_2O$ solution containing ~4 mM 1 was heated at 75° C. for 24 hours.

Figure 36:
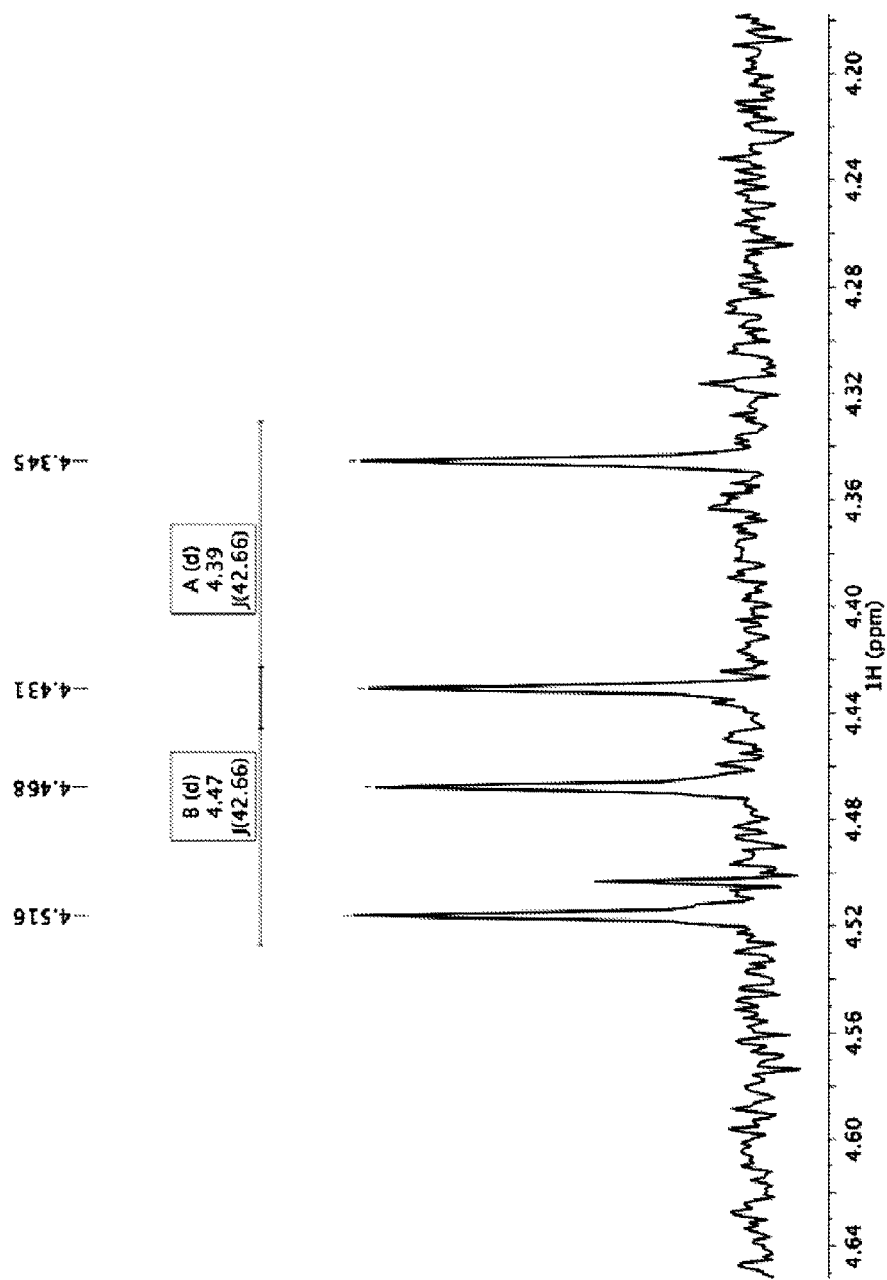
FIG. 36. Partial $^1H$ NMR spectrum showing $H_2$ and HD in a $C_6D_6$ solution, after vacuum transfer from a catalytic reaction in which ~4 mM 1 was dissolved in 3 M $H^{13}CO_2H/D_2O$ and heated to 75° C. for 24 hours.

FIG. 36 illustrates partial $^1H$ NMR spectrum showing $H_2$ and HD in a $C_6D_6$ solution, after vacuum transfer from a catalytic reaction in which ~4 mM 1 was dissolved in 3 M $H^{13}CO_2H/D_2O$ and heated to 75° C. for 24 hours.

$^2H$ Labeled Formic Acid Experiment.

A Teflon-sealable NMR tube was charged with a 0.5 mL solution of a 1.08 mg ($1.35 \times 10^{-6}$ mol) catalyst 1 in 3 M formic acid-$d_2$ in $H_2O$ ([Ir]=2.7 mM). A $^1H$ NMR spectrum was obtained, and then the tube was heated to 80° C. for 18 hours with occasional spectroscopic monitoring. The only isotopologue observed by $^1H$ and $^2H$ NMR spectroscopy was $CH_2DOH$ ($^1H$ NMR: δ 3.33, 1:1:1 triplet, $J_{HD}$=1.5 Hz. $^2H$ NMR: δ 3.34, t, $J_{HD}$=1.6 Hz), indicating that the C-D bond remained intact during the catalytic reaction.

Figure 37:
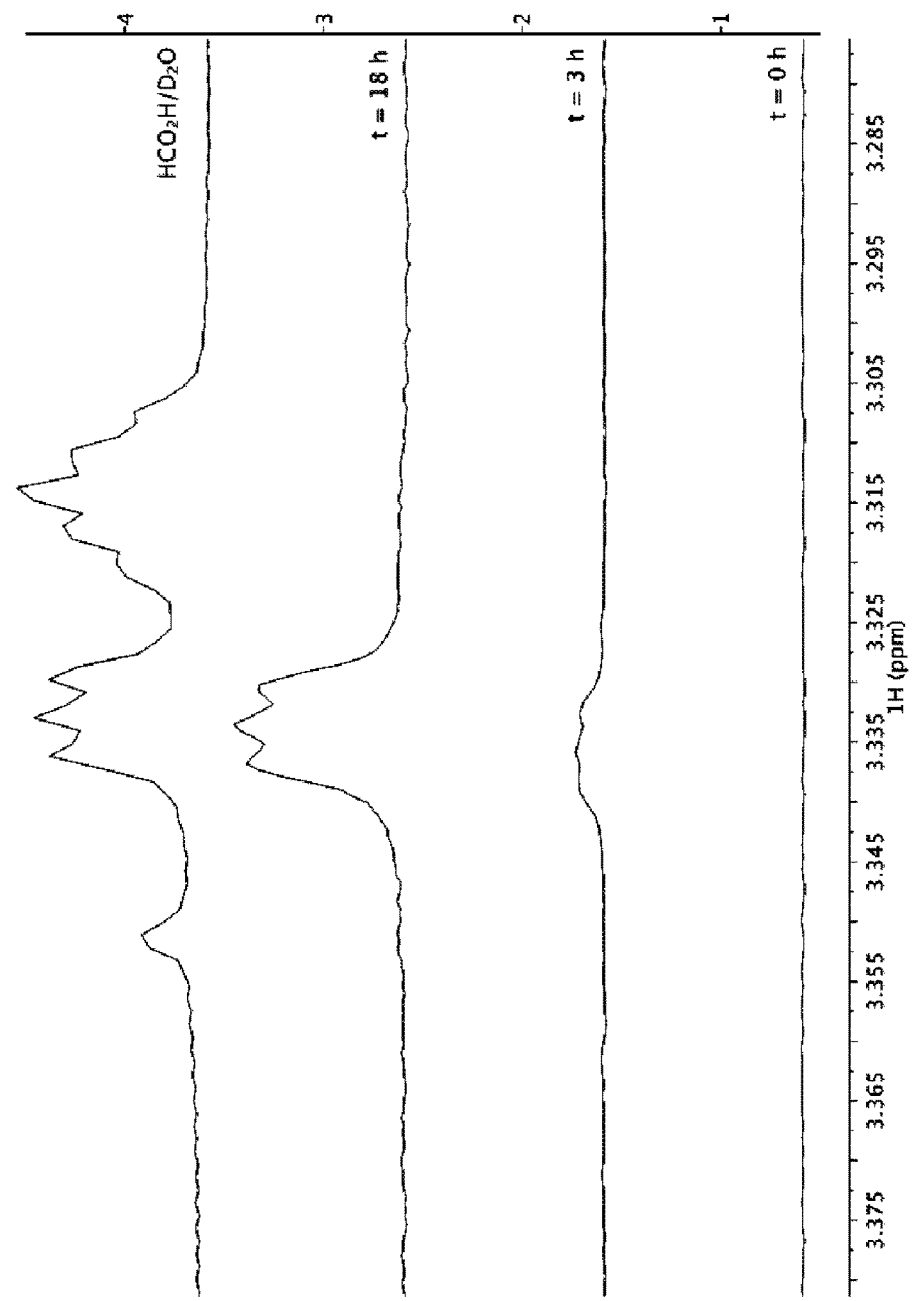
FIG. 37. $^1H$ NMR time course of methanol production from formic acid-$d_2$ in $H_2O$. From bottom: before heating, 3 h, 18 h. Top spectrum shows mixture of $CH_3OD$, $CH_2DOD$, and $CHD_2OD$ from a separate experiment. Conditions: 2.7 mM 1, 3 M formic acid-$d_2$ in $H_2O$, 80° C.

FIG. 37 illustrates $^1H$ NMR time course of methanol production from formic acid-$d_2$ in $H_2O$. From bottom: before heating, 3 h, 18 h. Top spectrum shows mixture of $CH_3OD$, $CH_2DOD$, and $CHD_2OD$ from a separate experiment. Conditions: 2.7 mM 1, 3 M formic acid-$d_2$ in $H_2O$, 80° C.

G. Probing Possible Reaction Intermediates.

$^{13}C$-Formaldehyde.

A Teflon-sealable NMR tube was charged with 6 mg (0.194 mMol) paraformaldehyde-$^{13}C$ and 0.45 mL 3 M formic acid in $D_2O$. The tube was heated at 60° C. for 19 hours. The insoluble white powder dissolved during this time, and a resonance at δ 4.68 (d, $J_{CH}$=164 Hz) appeared. No methanol or other products were observed in the absence of Ir catalyst. The tube was cooled and returned to the glovebox, and 100 μL of 0.25 mM 1 in 3 M formic acid in $H_2O$ was added by syringe ([Ir]=0.045 mM; $2.5 \times 10^{-8}$ moles of Ir; 7760 equivalents of formaldehyde). A small amount of solid NaOTs was also added as an internal standard. The tube was heated to 60° C. and periodically cooled and monitored by $^1H$ NMR spectroscopy. Roughly 30% conversion of the paraformaldehyde to a mixture of methanol-$^{13}C$ and methyl formate-$^{13}C$ ($HCO_2{}^{13}CH_3$) was observed after 10 hours. Spectra taken after 4 days showed that all of the paraformaldehyde was converted to a mixture of methanol and methyl formate (TON=7,760; $TOF_{init}$ (after 10 hours)=240 $h^{-1}$). Only a small amount of formic acid was consumed during the reaction, showing that conversion of formaldehyde to methanol is far more efficient than either the decomposition to $H_2/CO_2$ or disproportionation of formic acid to methanol under these conditions.

Ethyl Formate.

Methyl formate was tested as a possible intermediate using ethyl formate as a model. The ethyl derivative was chosen in order to distinguish between hydrogenation and hydrolysis; in the former case, methanol and ethanol would be formed in an equimolar ratio, but in the latter case only ethanol would be observed. A vial was charged with 1.0 mg (1.25 μmol) 1, and 1 mL of 3 M formic acid in $D_2O$ was added to generate a 1.25 mM stock solution of catalyst. A Teflon-sealable NMR tube was charged with 0.5 mL of the 1.25 mM 1 stock solution and 5 μL (6.25 μmol, 100 equiv) ethyl formate was added by syringe. A sealed capillary containing 250 mM NaTSP was added to the tube, which was then sealed and monitored by $^1H$ NMR spectroscopy intermittently (298 K) during heating at 60° C. In the 30 minutes between preparing the reaction mixture and taking the initial $^1$H NMR spectrum before heating, significant amounts of ethanol (but no methanol) were observed, indicating that hydrolysis (not hydrogenation) was operative, even at room temperature. After 1.5 hours at 60° C., almost all of the ethyl formate had been converted to ethanol and formic acid, as evidenced by a lack of observed methanol. Under these conditions, hydrolysis is clearly faster than hydrogenation.

Testing Reversibility of Methanol Formation.

In order to determine whether methanol formation is reversible under the catalytic conditions, formic acid-$d_2$ was treated with catalyst 1 in the presence of $^{13}CH_3OH$. In a small scintillation vial, 0.650 mg (0.813 μmol) Ir catalyst 1 and 2.0 mg (11.6 μmol) NaTSP were dissolved in 0.4 mL $D_2O$ containing 20 mM $^{13}CH_3OH$. $DCO_2D$ (50 μL, 1.2 mMol) was added to the mixture by syringe, providing a 3 M $DCO_2D/D_2O$ solution containing the catalyst, internal standard, and $^{13}CH_3OH$. The mixture was transferred to a Teflon-sealable NMR tube, and multinuclear NMR spectra were acquired. The tube was then heated to 80° C. for 30 hours, with periodic monitoring by NMR spectroscopy (298 K).

NMR spectra showed partial conversion of $^{13}CH_3OH$ to methyl formate-$^{13}C$, $HCO_2^{13}CH_3$ (in a ratio similar to that observed in the standard reaction conditions. If methanol formation is reversible under these conditions, $H^{13}CO_2H$ would be formed and subsequently converted to other isotopologues of methanol (e.g., $^{13}CHD_2OD$). However, the amount of $^{13}CH_3OH$ and $^{13}CH_3OCHO$ remained constant. No $^{13}C$-labeled formic acid was observed, nor were any other isotopologues of methanol or methyl formate observed, consistent with methanol formation being irreversible under these conditions. This is consistent with the estimated thermodynamics of equation 4 (see below).

Electrospray Ionization Mass Spectrometry.

Samples were prepared under typical catalytic reaction conditions (0.25 mM 1, 3 M $HCO_2H$) under nitrogen. After ~30 minutes at room temperature, the solutions were injected and analyzed in positive ion acquisition mode. In 3 M $HCO_2H/D_2O$, the two major fragments displayed m/z 486.2 and 529.1, consistent with the presence of [Cp*Ir(bpy)(D)]+ (calc. m/z 486.16) and [Cp*Ir(bpy)($O_2$CH)]$^+$ (calc. m/z 529.15).

Figure 38:
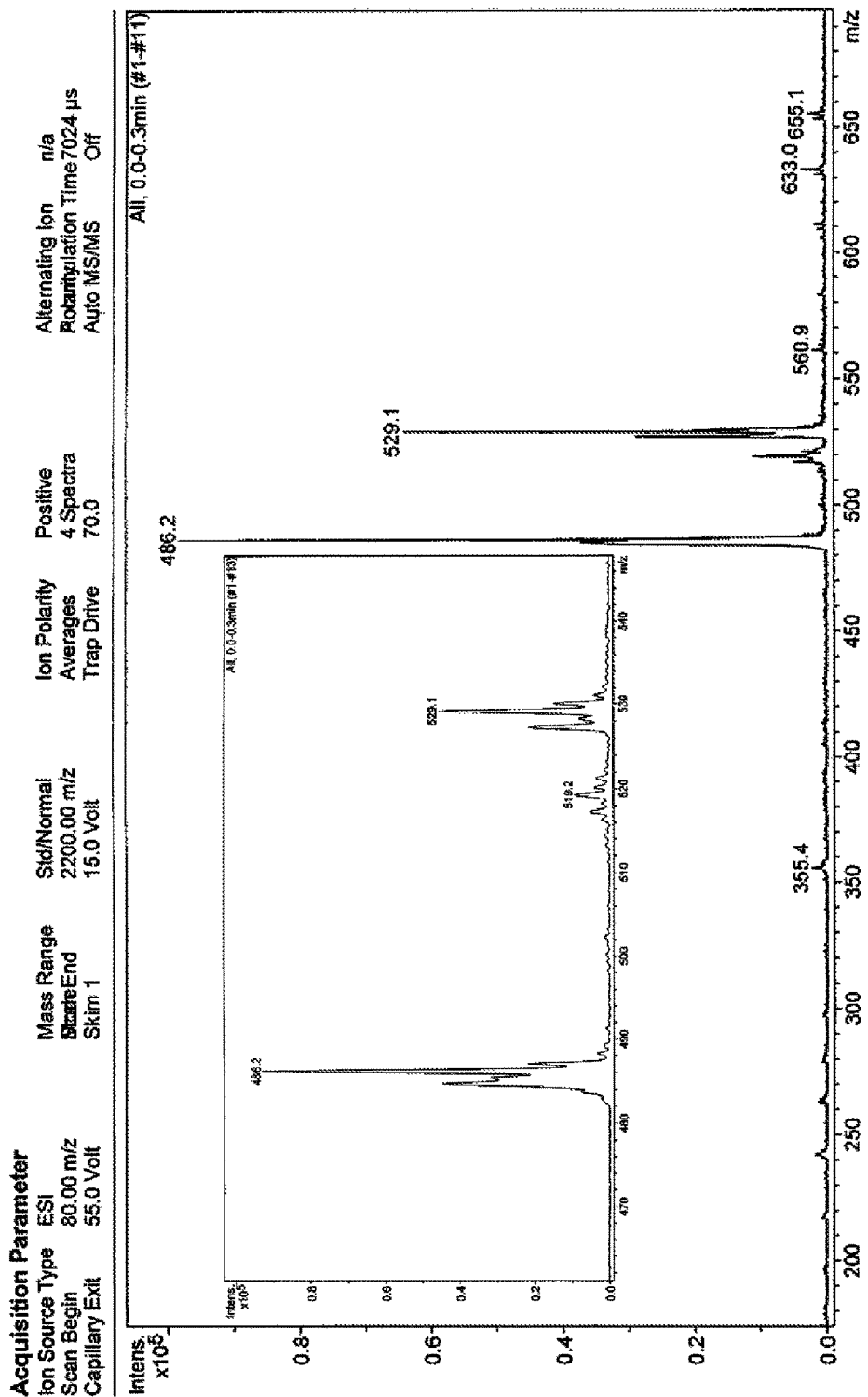
FIG. 38. Positive mode ESI-MS spectrum of a typical catalytic formic acid disproportionation reaction in $D_2O$, showing the presence of $[Cp*Ir(bpy)(D)]^+$ (m/z 486.2) and $[Cp*Ir(bpy)(O_2CH)]^+$ (m/z 529.1). Inset: blow-up of region of interest. Conditions: 0.25 mM 1, 3 M $HCO_2H/D_2O$.

FIG. 38 illustrates a positive mode ESI-MS spectrum of a typical catalytic formic acid disproportionation reaction in $D_2O$, showing the presence of [Cp*Ir(bpy)(D)]$^+$ (m/z 486.2) and [Cp*Ir(bpy)($O_2$CH)]$^+$ (m/z 529.1). Inset: blow-up of region of interest. Conditions: 0.25 mM 1, 3 M $HCO_2H/D_2O$.

IV. Thermodynamic Considerations

Method 1.

Electrochemical standard formal potentials E were obtained from the literature. The E values are given for pH 7 aqueous solutions with 1 atm gas pressure, and 1 M in all other solutes. The E values were converted to $\Delta G_{298}$ by, $$\Delta G = -nFE$$

where n is the number of electrons transferred in the reaction, F is Faraday's constant (23.06 kcal V$^{-1}$). All potentials are given at pH 7 vs the Normal Hydrogen Electrode. The half-reactions are all pH dependent. For example, the proton reduction reaction, $$H^+ + e^- \Leftrightarrow H_2$$

has E=0-0.0591·pH (−0.41V at pH 7). The full reactions involving $H_2$ and $HCO_2H$ are pH independent.

| | |
|---|---|
| $CO_2 + 6 H^+ + 6 e^- = CH_3OH + H_2O$ | $\Delta G = -6(23.06)(-0.38V)$ |
| $3 H_2 = 6 H^+ + 6 e^-$ | $\Delta ZG = -6(23.06)(+0.41V)$ |
| $CO_2(g) + 3 H_2(g) \rightarrow CH_3OH(aq) + H_2O(aq)$ | $\Delta G°_{298} = 4.2$ kcal · mol$^{-1}$ |
| $CO_2\ 3\ H_2 = CH_3OH + H_2O$ | $\Delta G = 4.2$ kcal · mol$^{-1}$ |
| $3\ HCO_2H = 3\ CO_2 + 6\ H^+ + 6\ e^-$ | $\Delta G = -6(23.06)(+0.61V)$ |
| $6\ H^+ + 6\ e^- = 3\ H_2$ | $\Delta G = -6(23.06)(-0.41V)$ |
| $3\ HCO_2H(aq) \rightarrow CH_3OH(aq) + H_2O(aq) + 2\ CO_2(g)$ | $\Delta G°_{298} = -23.5$ kcal · mol$^{-1}$ |
| $HCO_2H = CO_2 + 2 H^+ + 2 e^-$ | $\Delta G = -2(23.06)(+0.61V)$ |
| $2\ H^+ + 2\ e^- = H_2$ | $\Delta G = -2(23.06)(-0.41V)$ |
| $HCO_2H(aq) \rightarrow CO_2(g) + H_2(g)$ | $\Delta G°_{298} = -9.2$ kcal · mol$^{-1}$ |
| $CO_2 + 2 H^+ + 2 e^- = CO + H_2O$ | $\Delta G = -2(23.06)(-0.53V)$ |
| $HCO_2H = CO_2 + 2 H^+ + 2 e^-$ | $\Delta G = -2(23.06)(+0.61V)$ |
| $HCO_2H(aq) \rightarrow CO(g) + H_2O(aq)$ | $\Delta G°_{298} = -3.7$ kcal · mol$^{-1}$ |
| $CO_2 + 4 H^+ + 4 e^- = H_2CO + H_2O$ | $\Delta G = -4(23.06)(-0.48V)$ |
| $2 H_2 = 4 H^+ + 4 e^-$ | $\Delta G = -4(23.06)(+0.41V)$ |
| $CO_2(g) + 2 H_2(g) \rightarrow H_2CO(aq) + H_2O(aq)$ | $\Delta G°_{298} = 6.5$ kcal · mol$^{-1}$ |
| $CO_2(g) + 2 H_2(g) \rightarrow H_2CO(aq) + H_2O(aq)$ | $\Delta G°_{298} = 6.5$ kcal · mol$^{-1}$ |
| $2\ HCO_2H = 2\ CO_2 + 4\ H^+ + 4\ e^-$ | $\Delta G = -4(23.06)(+0.61V)$ |
| $4 H^+ + 4 e^- = 2 H_2$ | $\Delta G = -4(23.06)(-0.41V)$ |
| $2\ HCO_2H(aq) \rightarrow H_2CO(aq) + H_2O(aq) + CO_2(g)$ | $\Delta G°_{298} = -11.9$ kcal · mol$^{-1}$ |

Method 2.

Thermochemical data was also calculated using values for enthalpy of formation and entropy at standard conditions (pure substance or 1 bar of gas). The enthalpy and entropy values are for the phase of the substance under standard conditions (either gas or liquid), as indicated.

For the disproportionation reaction:

$$3HCO_2H(l) \rightarrow CH_3OH(l) + H_2O(l) + 2CO_2(g)$$

$$\Delta H° = [\Delta_fH°_{liq}(CH_3OH) + \Delta_fH°_{liq}(H_2O) + 2*(\Delta_fH°_{gas}(CO_2))] - [3*(\Delta_fH°_{liq}(HCO_2H))]$$

$$\Delta H° = [(-57) + (-68.3) + 2*(-94)] - [3*(-101.6)]$$

$$\Delta H° = -8.5\ \text{kcal·mol}^{-1}$$

$$\Delta S° = 56.2\ \text{cal·mol}^{-1}\text{K}^{-1}$$

$$\Delta G°_{298} = \Delta H° - T\Delta S° = -25.2\ \text{kcal·mol}^{-1}$$

| | |
|---|---|
| $HCO_2H(l) \rightarrow CO_2(g) + H_2(g)$ | $\Delta G°_{298} = -7.7$ kcal·mol$^{-1}$ |
| $HCO_2H(l) \rightarrow CO(g) + H_2O(l)$ | $\Delta G°_{298} = -2.9$ kcal·mol$^{-1}$ |
| $2\ HCO_2H(l) \rightarrow H_2CO(g) + H_2O(l) + CO_2(g)$ | $\Delta G°_{298} = -2.4$ kcal·mol$^{-1}$ |
| $3\ HCO_2H(l) \rightarrow CH_3OH(l) + H_2O(l) + 2\ CO_2(g)$ | $\Delta G°_{298} = -25.2$ kcal·mol$^{-1}$ |

The two calculations give slightly different values because they refer to slightly different reactions. For instance, the electrochemical calculations involve 1 M methanol in water while the thermochemical data are for pure MeOH. Considerations of state can have a large impact on the thermochemistry: $HCO_2H(aq) \rightarrow CO_2(g) + H_2(g)$ is downhill ($\Delta G°_{298} = -7.7$ kcal mol$^{-1}$, see above), but $HCO_2H(aq) \rightarrow CO_2(aq) + H_2(aq)$ is uphill ($\Delta G°_{298} = +1$ kcal mol$^{-1}$). Both methods give values that are only approximations of the thermochemistry under the reaction conditions used. As the formic acid concentration is increased, such as at 3 or 12 M formic acid, "standard state" approximations may not apply. For example, the pH dependencies of the electrochemical potentials may break down as proton activity becomes a more useful description of the solvent medium. The values given here are provided as a guide, not as absolute values.

V. Mechanistic Proposals

Figure 39:
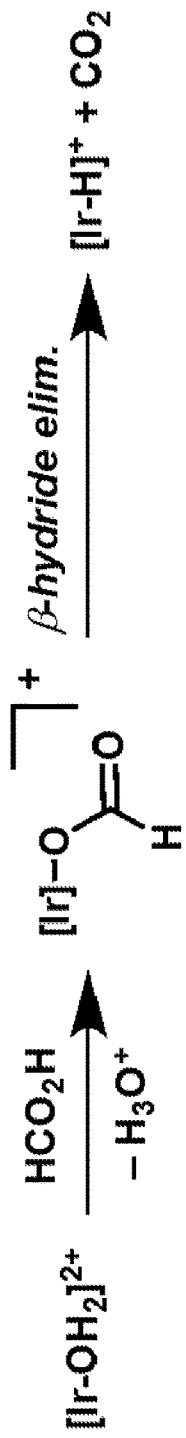
FIG. 39. Proposed mechanism of hydride formation.

While far more mechanistic study will be required to fully elucidate the mechanism of catalytic methanol production, some initial discussion is valuable. FIG. 39 shows the accepted mechanism of hydride formation in transfer hydrogenations with formic acid. Possible pathways for H/D exchange and methanol formation are also shown.

FIG. 39 is a proposed mechanism of hydride formation.

Figure 40:
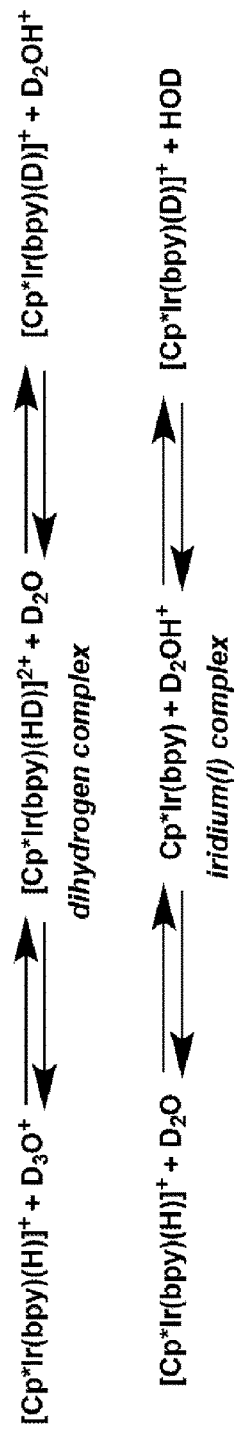
FIG. 40. Possible mechanisms of H/D exchange in $[Cp*Ir(bpy)(H)]+$.

FIG. 40 is a possible mechanisms of H/D exchange in [Cp*Ir(bpy)(H)]$^+$.

Figure 41:
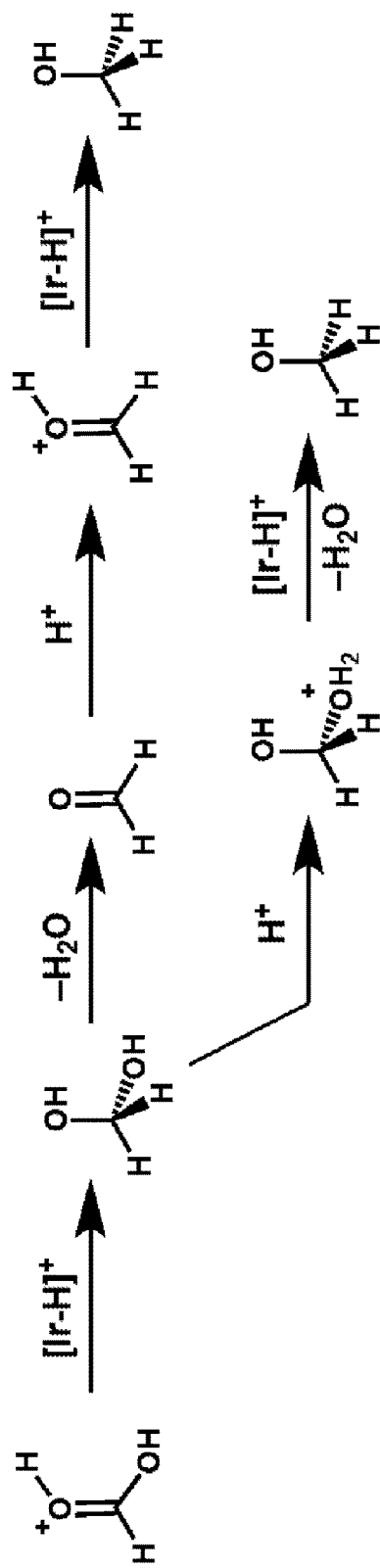
FIG. 41. Reduction of protonated formic acid to methanol.

FIG. 41 illustrates the reduction of protonated formic acid to methanol.

While illustrative embodiments have been illustrated and described, it will be appreciated that various changes can be made therein without departing from the spirit and scope of the invention.

The invention claimed is:

1. A method of hydrogenating a substrate, comprising exposing the substrate and a catalyst to hydrogen gas; wherein the substrate is selected from the group consisting of a carboxylic acid, a carbonate, and an ester; and the catalyst is selected from the group consisting of:

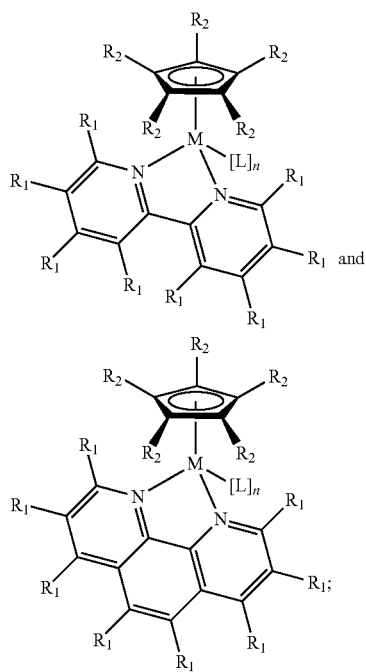

wherein M is selected from the group consisting of Ir and Rh;
wherein n is 0 or 1;
wherein when n is 1 L is selected from the group consisting of an anion and a molecule of a solvent;
wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and
wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

2. A method of hydrogenating a substrate, comprising exposing the substrate and a catalyst to hydrogen gas, wherein the substrate is selected from the group consisting of a carboxylic acid, a carbonate, and an ester; and the catalyst comprises:

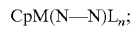

wherein Cp is a substituted or unsubstituted cyclopentadienyl ligand;
wherein M is selected from the group consisting of Ir and Rh;
wherein N—N is a substituted or unsubstituted bidentate ligand selected from the group consisting of a bipyridine ligand and a phenanthroline ligand;
wherein n is 0 or 1; and
wherein when n is 1 L is selected from the group consisting of an anion and a molecule of a solvent.

3. A method of forming methanol, comprising contacting formic acid, wherein the concentration of formic acid is from 0.5 M to 23.4 M, under acidic conditions with a catalyst selected from the group consisting of:

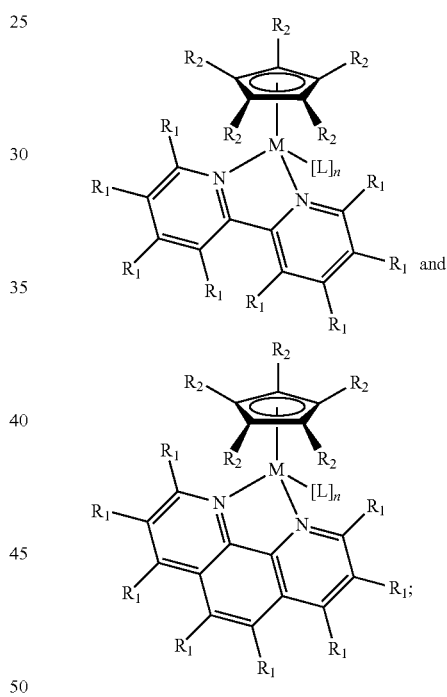

wherein M is selected from the group consisting of Ir and Rh;
wherein n is 0 or 1;
wherein when n is 1 L is selected from the group consisting of an anion and a molecule of a solvent;
wherein $R_1$ at each instance is independently selected from substituted or unsubstituted moieties of the group consisting of hydrogen, hydroxy, alkyl ester, aryl ester, alkyl, aryl, arylalkyl, alkenyl, alkoxy, amino, alkylamino, dialkylamino, and halogen; and
wherein $R_2$ at each instance is independently selected from the group consisting of hydrogen, hydroxy, alkyl ester, aryl ester, alkyl, aryl, arylalkyl, alkenyl, alkoxy, amino, alkylamino, dialkylamino, silyl, and halogen.

4. A method of forming methanol, comprising contacting formic acid, wherein the concentration of formic acid is from 0.5 M to 23.4 M, under acidic conditions with a catalyst comprising:

CpM(N—N)L$_n$;

wherein Cp is a substituted or unsubstituted cyclopentadienyl ligand;

wherein M is selected from the group consisting of Ir and Rh;

wherein N—N is a substituted or unsubstituted bidentate ligand selected from the group consisting of a bipyridine ligand and a phenanthroline ligand;

wherein n is 0 or 1; and wherein when n is 1 L is selected from the group consisting of an anion and a molecule of a solvent.

5. The method of claim 3, wherein the catalyst and the formic acid form a mixture.

6. The method of claim 5, wherein the mixture comprises a solvent that solvates the formic acid and the catalyst.

7. The method of claim 5, wherein the mixture contains no solvent.

8. The method of claim 3, wherein the catalyst is homogeneous.

9. The method of claim 3, wherein the catalyst is heterogeneous.

10. The method of claim 3, wherein the solvent is water.

11. The method of claim 3, wherein L is an anion selected from the group consisting of hydride, chloride, bromide, iodide, trifluoromethanesulfonate, sulfate, hydroxide, perchlorate, acetate, nitrate, trifluoroacetate, phosphate, and hydrogen phosphate.

12. The method of claim 4, wherein the catalyst and the formic acid form a mixture.

13. The method of claim 12, wherein the mixture comprises a solvent that solvates the formic acid and the catalyst.

14. The method of claim 12, wherein the mixture contains no solvent.

15. The method of claim 4, wherein the catalyst is homogeneous.

16. The method of claim 4, wherein the catalyst is heterogeneous.

17. The method of claim 4, wherein the solvent is water.

18. The method of claim 4, wherein L is an anion selected from the group consisting of hydride, chloride, bromide, iodide, trifluoromethanesulfonate, sulfate, hydroxide, perchlorate, acetate, nitrate, trifluoroacetate, phosphate, and hydrogen phosphate.

19. The method of claim 1, wherein the catalyst is a cation with one or more anions associated with the catalyst, wherein the anions are selected from the group consisting of triflate, hexafluorophosphate, chloride, tetrafluoroborate, triflamide, tetraphenylborate, iodide, bromide, tetrafluorophenylborate, tetrakis[3,5-bis(trifluoromethyl)phenyl]borate, hexafluoro antimonate, nitrate, perchlorate, tetrakis(pentafluorophenyl)borate, tosylate, acetate, trifluoroacetate, phosphate, hydrogen phosphate, carbonate, sulfate, nitrite, cyanide, cyanate, thiocyanate, iodate, bromate, chlorate, oxalate, and hydroxide.

20. The method of claim 3, wherein the catalyst is a cation with one or more anions associated with the catalyst, wherein the anions are selected from the group consisting of triflate, hexafluorophosphate, chloride, tetrafluoroborate, triflamide, tetraphenylborate, iodide, bromide, tetrafluorophenylborate, tetrakis[3,5-bis(trifluoromethyl)phenyl]borate, hexafluoro antimonate, nitrate, perchlorate, tetrakis(pentafluorophenyl)borate, tosylate, acetate, trifluoroacetate, phosphate, hydrogen phosphate, carbonate, sulfate, nitrite, cyanide, cyanate, thiocyanate, iodate, bromate, chlorate, oxalate, and hydroxide.

\* \* \* \* \*